(12) United States Patent
Decarolis et al.

(10) Patent No.: US 7,427,656 B2
(45) Date of Patent: Sep. 23, 2008

(54) PEPTIDE TAGS FOR THE EXPRESSION AND PURIFICATION OF BIOACTIVE PEPTIDES

(75) Inventors: Linda Jane Decarolis, Wilmington (DE); Stephen R. Fahnestock, Wilmington (DE); Hong Wang, Kennett Square, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 79 days.

(21) Appl. No.: 11/516,362

(22) Filed: Sep. 5, 2006

(65) Prior Publication Data

US 2008/0206809 A1  Aug. 28, 2008

Related U.S. Application Data

(60) Provisional application No. 60/721,329, filed on Sep. 28, 2005.

(51) Int. Cl.
*C07K 2/00* (2006.01)
*C07K 14/00* (2006.01)
(52) U.S. Cl. .................. 530/300; 530/324; 530/350
(58) Field of Classification Search .................. None
See application file for complete search history.

(56) References Cited

U.S. PATENT DOCUMENTS

| | | | |
|---|---|---|---|
| 4,870,023 | A | 9/1989 | Fraser et al. |
| 5,110,729 | A | 5/1992 | Maeda et al. |
| 5,206,154 | A | 4/1993 | Lai et al. |
| 5,215,896 | A | 6/1993 | Keck et al. |
| 5,223,409 | A | 6/1993 | Ladner et al. |
| 5,302,526 | A | 4/1994 | Keck et al. |
| 5,330,902 | A | 7/1994 | Keck et al. |
| 5,403,484 | A | 4/1995 | Ladner et al. |
| 5,449,754 | A | 9/1995 | Nishioka |
| 5,480,971 | A | 1/1996 | Houghten et al. |
| 5,571,698 | A | 11/1996 | Ladner et al. |
| 5,585,275 | A | 12/1996 | Husdon et al. |
| 5,639,603 | A | 6/1997 | Dower et al. |
| 5,648,244 | A | 7/1997 | Kuliopulos et al. |
| 5,670,340 | A | 9/1997 | Yabuta et al. |
| 5,837,500 | A | 11/1998 | Ladner |
| 6,037,145 | A | 3/2000 | Yabuta et al. |
| 6,242,219 | B1 | 6/2001 | Better et al. |
| 6,613,548 | B1 | 9/2003 | Chu |
| 6,620,419 | B1 | 9/2003 | Lintner |
| 6,699,689 | B1 | 3/2004 | Kim et al. |
| 2003/0152976 | A1 | 8/2003 | Janssen et al. |
| 2003/0185870 | A1 | 10/2003 | Grinstaff et al. |
| 2004/0142492 | A1 | 7/2004 | Kiesewetter et al. |
| 2005/0221444 | A1 | 10/2005 | Williams et al. |

FOREIGN PATENT DOCUMENTS

| WO | WO 94/04688 A2 | 3/1994 |
|---|---|---|
| WO | WO 00/04165 A1 | 1/2000 |
| WO | WO 03/100021 A2 | 12/2003 |

OTHER PUBLICATIONS

Accession No. 049204, Adenylyl-sulfate kinase, chloroplast precursor (EC 2.7.1.25) (APS kinase) (Adenosine-5'-phosphosulfate 3'-phosphotransferase), Jun. 1, 1998. UniProt Consortium.
AC: Q95XH9, Hypothetical protein, Dec. 1, 2001, UniProt Consortium.
U.S. Appl. No. 10/935,642, filed Sep. 7, 2004, Xueying Huang et al.
U.S. Appl. No. 10/935,254, filed Sep. 7, 2004, O'Brien et al.
Kemp et. al., Direct Immunoassay for Detecting *Escherichia coli* Colonies That Contain Polypeptides Encoded by Cloned DNA Segments, Proc. Natl. Acad. Sci., 1981, vol. 78:4520=4524.
Chien et. al., The Two-Hybird System: a Method to Identify and Clone Genes for Proteins That Interact with a Protein of Interest, Proc. Natl. Acad. Sci., 1991, vol. 88:9578-9582.
Dykes et. al., Expression of Atrial Natriuretic Factor as a Cleavable Fusion Protein With Chloramphenicol Acetyltransferase in *Escherichia coli*, Eur. J. Biochem., 1988 vol. 174:411-416.
Schellenberger et. al., Peptide Production by a Combination of Gene Expression, Chemical Synthesis, and Protease-Catalyzed Conversion, Int. J. Peptide Proteins Res., 1993, vol. 41:326-332.
Shen, Multiple Joined Genes Prevent Product Degradation in *Escherichia coli*, Proc. Natl. Acad. Sci., 1984, vol. 81:4627-4631.
Kullopulus et. al., Production, Purification, and Cleavage of Tandem Repeats of Recombinant Peptides, J. Am. Chem. Soc., 1994, vol. 116:4599-4607.
A. Pilon et. al., Ubiquitin Fusion Technology: Bioprocessing of Peptides, Biotechnol. Prog., 1997, vol. 13:374-379.
Haught et. al., Recombinant Production and Purification of Novel Antisense Antimicrobial Peptide in *Escherichia coli*, Biotechnology and Bioengineering, 1988, vol. 57:55-61.
Kempe et. al., Multiple-Copy Genes: Production and Modification of Monomeric Peptides From Large Multimeric Fusion Proteins, Gene, 1985, vol. 39:239-245.
Ray et. al., Production of Recombinant Salmon Calcitonin by in Vitro Amidation of an *Escherichia coli* Produced Precursor Peptide, Bio/Technology, 1993, vol. 11:64-70.
Callaway et. al., Modification of the C Terminus of Cecropin is Essential for Broad-Spectrum Antimicrobial Agents and Chemotherapy, 1993, vol. 37: 1614-1619.
Gram et. al., A Novel Approach for High Level Production of a Recombinant Human Parathyroid Hormone Fragment in *Escherichia coli*, Bio/Technology, 1994, vol. 12:1017-1023.
Elegans, Genome Sequence of the Nematode C. Elegans: a Platform for Investigating Biology, Science, 1998, vol. 282: 2012-2018.

*Primary Examiner*—Maryam Monshipouri
*Assistant Examiner*—Marsha M Tsay

(57) ABSTRACT

Peptide tags, referred to here as inclusion body tags, are disclosed and are useful for the generation of insoluble fusion peptides. The fusion peptides comprise at least one inclusion body tag operably linked to a peptide of interest. Expression of the fusion peptide in a host cell results in a product that is insoluble and contained within inclusion bodies in the cell and/or cell lysate. The inclusion bodies may then be purified and the protein of interest may be isolated after cleavage from the inclusion body tag.

10 Claims, No Drawings

SEQUENCE LISTING

<160> NUMBER OF SEQ ID NOS: 332

<210> SEQ ID NO 1
<211> LENGTH: 195
<212> TYPE: DNA
<213> ORGANISM: artificial sequence
<220> FEATURE:
<223> OTHER INFORMATION: Chemically synthesized

<400> SEQUENCE: 1

```
ggtcgtttcc acgaaaactg gccgtctggt ggcggtacct ctacttccaa agcttccacc      60
actacgactt ctagcaaaac caccactaca tcctctaaga ctaccacgac tacctccaaa     120
acctctacta cctctagctc ctctacgggc ggtggcactc acaagacctc tactcagcgt     180
ctgctggctg cataa                                                      195
```

<210> SEQ ID NO 2
<211> LENGTH: 68
<212> TYPE: PRT
<213> ORGANISM: artificial sequence
<220> FEATURE:
<223> OTHER INFORMATION: chemically synthesized

<400> SEQUENCE: 2

Gly Ser Ile Glu Gly Arg Phe His Glu Asn Trp Pro Ser Ala Gly Gly
 1               5                  10                  15

Thr Ser Thr Ser Lys Ala Ser Thr Thr Thr Thr Ser Ser Lys Thr Thr
            20                  25                  30

Thr Thr Ser Ser Lys Thr Thr Thr Thr Thr Ser Lys Thr Ser Thr Thr
        35                  40                  45

Ser Ser Ser Ser Thr Gly Gly Ala Thr His Lys Thr Ser Thr Gln Arg
    50                  55                  60

Leu Leu Ala Ala
65

<210> SEQ ID NO 3
<211> LENGTH: 103
<212> TYPE: DNA
<213> ORGANISM: artificial sequence
<220> FEATURE:
<223> OTHER INFORMATION: Oligo used to prepare TBP1

<400> SEQUENCE: 3

```
ggatccatcg aaggtcgttt ccacgaaaac tggccgtctg gtggcggtac ctctacttcc      60
aaagcttcca ccactacgac ttctagcaaa accaccacta cat                      103
```

<210> SEQ ID NO 4
<211> LENGTH: 104
<212> TYPE: DNA
<213> ORGANISM: artificial sequence
<220> FEATURE:
<223> OTHER INFORMATION: Oligo used to prepare TBP1

<400> SEQUENCE: 4

```
cctctaagac taccacgact acctccaaaa cctctactac ctctagctcc tctacgggcg      60
gtggcactca caagacctct actcagcgtc tgctggctgc ataa                     104
```

<210> SEQ ID NO 5
<211> LENGTH: 69
<212> TYPE: DNA
<213> ORGANISM: artificial sequence
<220> FEATURE:
<223> OTHER INFORMATION: Oligo used to prepare TBP1

<400> SEQUENCE: 5

```
ttatgcagcc agcagacgct gagtagaggt cttgtgagtg ccaccgcccg tagaggagct      60
agaggtagt                                                             69
```

<210> SEQ ID NO 6
<211> LENGTH: 69
<212> TYPE: DNA
<213> ORGANISM: artificial sequence
<220> FEATURE:
<223> OTHER INFORMATION: Oligo used to prepare TBP1

<400> SEQUENCE: 6

```
agaggttttg gaggtagtcg tggtagtctt agaggatgta gtggtggttt tgctagaagt      60
cgtagtggt                                                             69
```

<210> SEQ ID NO 7
<211> LENGTH: 69
<212> TYPE: DNA
<213> ORGANISM: artificial sequence
<220> FEATURE:
<223> OTHER INFORMATION: Oligo used to prepare TBP1

<400> SEQUENCE: 7

```
ggaagctttg gaagtagagg taccgccacc agacggccag ttttcgtgga aacgaccttc      60
gatggatcc                                                             69
```

<210> SEQ ID NO 8
<211> LENGTH: 22
<212> TYPE: DNA
<213> ORGANISM: artificial sequence
<220> FEATURE:
<223> OTHER INFORMATION: Primer

<400> SEQUENCE: 8

-continued

| caccggatcc atcgaaggtc gt | 22 |

<210> SEQ ID NO 9
<211> LENGTH: 21
<212> TYPE: DNA
<213> ORGANISM: artificial sequence
<220> FEATURE:
<223> OTHER INFORMATION: Primer

<400> SEQUENCE: 9

| tcattatgca gccagcagcg c | 21 |

<210> SEQ ID NO 10
<211> LENGTH: 2580
<212> TYPE: DNA
<213> ORGANISM: artificial sequence
<220> FEATURE:
<223> OTHER INFORMATION: plasmid

<400> SEQUENCE: 10

| ctttcctgcg ttatcccctg attctgtgga taaccgtatt accgcctttg agtgagctga | 60 |
| taccgctcgc cgcagccgaa cgaccgagcg cagcgagtca gtgagcgagg aagcggaaga | 120 |
| gcgcccaata cgcaaaccgc ctctccccgc gcgttggccg attcattaat gcagctggca | 180 |
| cgacaggttt cccgactgga aagcgggcag tgagcgcaac gcaattaata cgcgtaccgc | 240 |
| tagccaggaa gagtttgtag aaacgcaaaa aggccatccg tcaggatggc cttctgctta | 300 |
| gtttgatgcc tggcagttta tggcgggcgt cctgcccgcc accctccggg ccgttgcttc | 360 |
| acaacgttca atccgctccc ggcggatttg tcctactcag ggagagcgtt caccgacaaa | 420 |
| caacagataa acgaaaggcc cagtcttccg actgagcctt tcgttttatt tgatgcctg | 480 |
| gcagttccct actctcgcgt taacgctagc atggatgttt tcccagtcac gacgttgtaa | 540 |
| aacgacggcc agtcttaagc tcgggcccca ataatgatt ttattttgac tgatagtgac | 600 |
| ctgttcgttg caacaaattg atgagcaatg cttttttata atgccaactt tgtacaaaaa | 660 |
| agcaggctcc gcggccgccc cttcaccaa gggtgggcgc gccgacccag ctttcttgta | 720 |
| caaagttggc attataagaa agcattgctt atcaatttgt tgcaacgaac aggtcactat | 780 |
| cagtcaaaat aaaatcatta tttgccatcc agctgatatc ccctatagtg agtcgtatta | 840 |
| catggtcata gctgtttcct ggcagctctg gcccgtgtct caaaatctct gatgttacat | 900 |
| tgcacaagat aaaaatatat catcatgaac aataaaactg tctgcttaca taaacagtaa | 960 |
| tacaaggggt gttatgagcc atattcaacg ggaaacgtcg aggccgcgat taaattccaa | 1020 |
| catggatgct gatttatatg ggtataaatg ggctcgcgat aatgtcgggc aatcaggtgc | 1080 |
| gacaatctat cgcttgtatg ggaagcccga tgcgccagag ttgtttctga acatggcaa | 1140 |
| aggtagcgtt gccaatgatg ttacagatga gatggtcaga ctaaactggc tgacggaatt | 1200 |
| tatgcctctt ccgaccatca agcattttat ccgtactcct gatgatgcat ggttactcac | 1260 |
| cactgcgatc cccggaaaaa cagcattcca ggtattagaa gaatatcctg attcaggtga | 1320 |
| aaatattgtt gatgcgctgg cagtgttcct gcgccggttg cattcgattc ctgtttgtaa | 1380 |
| ttgtcctttt aacagcgatc gcgtatttcg tctcgctcag gcgcaatcac gaatgaataa | 1440 |
| cggtttggtt gatgcgagtg attttgatga cgagcgtaat ggctggcctg ttgaacaagt | 1500 |
| ctggaaagaa atgcataaac ttttgccatt ctcaccggat tcagtcgtca ctcatggtga | 1560 |
| tttctcactt gataaccttat ttttgacga ggggaaatta ataggttgta ttgatgttgg | 1620 |
| acgagtcgga atcgcagacc gataccagga tcttgccatc ctatggaact gcctcggtga | 1680 |

```
gtttctcct tcattacaga aacggctttt tcaaaaatat ggtattgata atcctgatat    1740
gaataaattg cagtttcatt tgatgctcga tgagttttc taatcagaat tggttaattg    1800
gttgtaacac tggcagagca ttacgctgac ttgacgggac ggcgcaagct catgaccaaa    1860
atcccttaac gtgagttacg cgtcgttcca ctgagcgtca gaccccgtag aaaagatcaa    1920
aggatcttct tgagatcctt ttttctgcg cgtaatctgc tgcttgcaaa caaaaaaacc    1980
accgctacca gcggtggttt gtttgccgga tcaagagcta ccaactcttt tccgaaggt    2040 aactggcttc agcagagcgc agataccaaa tactgtcctt ctagtgtagc cgtagttagg    2100
ccaccacttc aagaactctg tagcaccgcc tacatacctc gctctgctaa tcctgttacc    2160
agtggctgct gccagtggcg ataagtcgtg tcttaccggg ttggactcaa gacgatagtt    2220
accggataag cgcagcggt cgggctgaac ggggggttcg tgcacacagc ccagcttgga    2280
gcgaacgacc tacaccgaac tgagatacct acagcgtgag cattgagaaa gcgccacgct    2340
tcccgaaggg agaaaggcgg acaggtatcc ggtaagcggc agggtcggaa caggagagcg    2400
cacgagggag cttccagggg gaaacgcctg gtatctttat agtcctgtcg ggtttcgcca    2460
cctctgactt gagcgtcgat ttttgtgatg ctcgtcaggg gggcggagcc tatggaaaaa    2520
cgccagcaac gcggcctttt tacggttcct ggccttttgc tggccttttg ctcacatgtt    2580
```

<210> SEQ ID NO 11
<211> LENGTH: 6354
<212> TYPE: DNA
<213> ORGANISM: artificial sequence
<220> FEATURE:
<223> OTHER INFORMATION: Plasmid

<400> SEQUENCE: 11

```
agatctcgat cccgcgaaat taatacgact cactataggg agaccacaac ggtttccctc      60
tagaaataat tttgtttaac tttaagaagg agatatacat atgtcgtact accatcacca     120
tcaccatcac ctcgaatcaa caagtttgta caaaaaagct gaacgagaaa cgtaaaatga     180
tataaatatc aatatattaa attagatttt gcataaaaaa cagactacat aatactgtaa     240
aacacaacat atccagtcac tatggcggcc gcattaggca ccccaggctt tacactttat     300
gcttccggct cgtataatgt gtggattttg agttaggatc cgtcgagatt tcaggagct     360 aaggaagcta aaatggagaa aaaaatcact ggatatacca ccgttgatat atcccaatgg     420
catcgtaaag aacattttga ggcatttcag tcagttgctc aatgtaccta taaccagacc     480
gttcagctgg atattacggc cttttaaag accgtaaaga aaataagca caagttttat      540 ccggccttta ttcacattct tgcccgcctg atgaatgctc atccggaatt ccgtatggca     600
atgaaagacg gtgagctggt gatatgggat agtgttcacc cttgttacac cgttttccat     660
gagcaaactg aaacgttttc atcgctctgg agtgaatacc acgacgattt ccggcagttt     720
ctacacatat attcgcaaga tgtggcgtgt tacggtgaaa acctggccta tttccctaaa     780
gggtttattg agaatatgtt tttcgtctca gccaatccct gggtgagttt caccagtttt     840
gatttaaacg tggccaatat ggacaacttc ttcgccccg ttttcaccat gggcaaatat     900
tatacgcaag cgacaaggt gctgatgccg ctggcgattc aggttcatca tgccgtctgt     960
gatggcttcc atgtcggcag aatgcttaat gaattacaac agtactgcga tgagtggcag    1020
ggcggggcgt aaagatctgg atccggctta ctaaaagcca gataacagta tgcgtatttg    1080
cgcgctgatt tttgcggtat aagaatatat actgatatgt atacccgaag tatgtcaaaa    1140
```

```
agaggtgtgc tatgaagcag cgtattacag tgacagttga cagcgacagc tatcagttgc   1200
tcaaggcata tatgatgtca atatctccgg tctggtaagc acaaccatgc agaatgaagc   1260
ccgtcgtctg cgtgccgaac gctggaaagc ggaaaatcag gaagggatgg ctgaggtcgc   1320
ccggtttatt gaaatgaacg gctcttttgc tgacgagaac agggactggt gaaatgcagt   1380
ttaaggttta cacctataaa agagagagcc gttatcgtct gtttgtggat gtacagagtg   1440
atattattga cacgcccggg cgacggatgg tgatccccct ggccagtgca cgtctgctgt   1500
cagataaagt ctcccgtgaa ctttacccgg tggtgcatat cggggatgaa agctggcgca   1560
tgatgaccac cgatatggcc agtgtgccgg tctccgttat cggggaagaa gtggctgatc   1620
tcagccaccg cgaaaatgac atcaaaaacg ccattaacct gatgttctgg ggaatataaa   1680
tgtcaggctc cctatacac agccagtctg caggtcgacc atagtgactg gatatgttgt   1740
gttttacagt attatgtagt ctgttttta tgcaaaatct aatttaatat attgatattt   1800
atatcatttt acgtttctcg ttcagctttc ttgtacaaag tggttgattc gaggctgcta   1860
acaaagcccg aaaggaagct gagttggctg ctgccaccgc tgagcaataa ctagcataac   1920
cccttggggc ctctaaacgg gtcttgaggg gttttttgct gaaaggagga actatatccg   1980
gatatccaca ggacgggtgt ggtcgccatg atcgcgtagt cgatagtggc tccaagtagc   2040
gaagcgagca ggactgggcg gcggccaaag cggtcggaca gtgctccgag aacgggtgcg   2100
catagaaatt gcatcaacgc atatagcgct agcagcacgc catagtgact ggcgatgctg   2160
tcggaatgga cgtatcccg caagaggccc ggcagtaccg gcataaccaa gcctatgcct   2220
acagcatcca gggtgacggt gccgaggatg acgatgagcg cattgttaga tttcatacac   2280
ggtgcctgac tgcgttagca atttaactgt gataaactac cgcattaaag cttatcgatg   2340
ataagctgtc aaacatgaga attcttgaag acgaaagggc ctcgtgatac gcctatttt   2400 ataggttaat gtcatgataa taatggtttc ttagacgtca ggtggcactt ttcggggaaa   2460
tgtgcgcgga accctatttt gtttatttt ctaaatacat tcaaatatgt atccgctcat   2520
gagacaataa ccctgataaa tgcttcaata atattgaaaa aggaagagta tgagtattca   2580
acatttccgt gtcgccctta ttccctttt tgcggcattt tgccttcctg tttttgctca   2640
cccagaaacg ctggtgaaag taaaagatgc tgaagatcag ttgggtgcac gagtgggtta   2700
catcgaactg gatctcaaca gcggtaagat ccttgagagt tttcgccccg aagaacgttt   2760
tccaatgatg agcacttta aagttctgct atgtggcgcg gtattatccc gtgttgacgc   2820
cgggcaagag caactcggtc gccgcataca ctattctcag aatgacttgg ttgagtactc   2880
accagtcaca gaaaagcatc ttacggatgg catgacagta agagaattat gcagtgctgc   2940
cataaccatg agtgataaca ctgcggccaa cttacttctg acaacgatcg gaggaccgaa   3000
ggagctaacc gcttttttgc acaacatggg ggatcatgta actcgccttg atcgttggga   3060
accggagctg aatgaagcca taccaaacga cgagcgtgac accacgatgc ctgcagcaat   3120
ggcaacaacg ttgcgcaaac tattaactgg cgaactactt actctagctt cccggcaaca   3180
attaatagac tggatggagg cggataaagt tgcaggacca cttctgcgct cggcccttcc   3240
ggctggctgg tttattgctg ataaatctgg agccggtgag cgtgggtctc gcggtatcat   3300
tgcagcactg gggccagatg gtaagccctc ccgtatcgta gttatctaca cgacggggag   3360
tcaggcaact atggatgaac gaaatagaca gatcgctgag ataggtgcct cactgattaa   3420
gcattggtaa ctgtcagacc aagtttactc atatatactt tagattgatt taaaacttca   3480
tttttaattt aaaaggatct aggtgaagat ccttttgat aatctcatga ccaaaatccc   3540
```

```
ttaacgtgag ttttcgttcc actgagcgtc agaccccgta gaaaagatca aaggatcttc   3600
ttgagatcct ttttttctgc gcgtaatctg ctgcttgcaa acaaaaaaac caccgctacc   3660
agcggtggtt tgtttgccgg atcaagagct accaactctt tttccgaagg taactggctt   3720
cagcagagcg cagataccaa atactgtcct tctagtgtag ccgtagttag gccaccactt   3780
caagaactct gtagcaccgc ctacatacct cgctctgcta atcctgttac cagtggctgc   3840
tgccagtggc gataagtcgt gtcttaccgg gttggactca agacgatagt taccggataa   3900
ggcgcagcgg tcgggctgaa cggggggttc gtgcacacag cccagcttgg agcgaacgac   3960
ctacaccgaa ctgagatacc tacagcgtga gctatgagaa agcgccacgc ttcccgaagg   4020
gagaaaggcg gacaggtatc cggtaagcgg cagggtcgga acaggagagc gcacgaggga   4080
gcttccaggg ggaaacgcct ggtatcttta tagtcctgtc gggtttcgcc acctctgact   4140
tgagcgtcga ttttgtgat gctcgtcagg ggggcgagc ctatggaaaa acgccagcaa   4200
cgcggccttt ttacggttcc tggccttttg ctggcctttt gctcacatgt tctttcctgc   4260
gttatcccct gattctgtgg ataaccgtat taccgccttt gagtgagctg ataccgctcg   4320
ccgcagccga acgaccgagc gcagcgagtc agtgagcgag gaagcggaag agcgcctgat   4380
gcggtatttt ctccttacgc atctgtgcgg tatttcacac cgcatatatg gtgcactctc   4440
agtacaatct gctctgatgc cgcatagtta agccagtata cactccgcta tcgctacgtg   4500
actgggtcat ggctgcgccc cgacacccgc caacacccgc tgacgcgccc tgacgggctt   4560
gtctgctccc ggcatccgct tacagacaag ctgtgaccgt ctccgggagc tgcatgtgtc   4620
agaggttttc accgtcatca ccgaaacgcg cgaggcagct gcggtaaagc tcatcagcgt   4680
ggtcgtgaag cgattcacag atgtctgcct gttcatccgc gtccagctcg ttgagtttct   4740
ccagaagcgt taatgtctgg cttctgataa agcgggccat gttaagggcg gttttttcct   4800
gtttggtcac tgatgcctcc gtgtaagggg gatttctgtt catggggta atgataccga   4860
tgaaacgaga gaggatgctc acgatacggg ttactgatga tgaacatgcc cggttactgg   4920
aacgttgtga gggtaaacaa ctggcggtat ggatgcggcg gaccagaga aaaatcactc   4980
agggtcaatg ccagcgcttc gttaatacag atgtaggtgt tccacagggt agccagcagc   5040
atcctgcgat gcagatccgg aacataatgg tgcaggcgc tgacttccgc gtttccagac   5100
tttacgaaac acggaaaccg aagaccattc atgttgttgc tcaggtcgca gacgttttgc   5160
agcagcagtc gcttcacgtt cgctcgcgta tcggtgattc attctgctaa ccagtaaggc   5220
aaccccgcca gcctagccgg gtcctcaacg acaggagcac gatcatgcgc acccgtggcc   5280
aggacccaac gctgcccgag atgcgccgcg tgcggctgct ggagatggcg gacgcgatgg   5340
atatgttctg ccaagggttg gtttgcgcat tcacagttct ccgcaagaat tgattggctc   5400
caattcttgg agtggtgaat ccgttagcga ggtgccgccg gcttccattc aggtcgaggt   5460
ggcccggctc catgcaccgc gacgcaacgc ggggaggcag acaaggtata gggcggcgcc   5520
tacaatccat gccaacccgt tccatgtgct cgccgaggcg gcataaatcg ccgtgacgat   5580
cagcggtcca gtgatcgaag ttaggctggt aagagccgcg agcgatcctt gaagctgtcc   5640
ctgatggtcg tcatctacct gcctggacag catggcctgc aacgcgggca tcccgatgcc   5700
gccggaagcg agaagaatca taatgggga ggccatccag cctcgcgtcg cgaacgccag   5760
caagacgtag cccagcgcgt cggccgccat gccggcgata atggcctgct tctcgccgaa   5820
acgtttggtg gcgggaccag tgacgaaggc ttgagcgagg gcgtgcaaga ttccgaatac   5880
```

```
cgcaagcgac aggccgatca tcgtcgcgct ccagcgaaag cggtcctcgc cgaaaatgac    5940
ccagagcgct gccggcacct gtcctacgag ttgcatgata agaagacag tcataagtgc     6000 ggcgacgata gtcatgcccc gcgcccaccg gaaggagctg actgggttga aggctctcaa    6060
gggcatcggt cgatcgacgc tctcccttat gcgactcctg cattaggaag cagcccagta    6120
gtaggttgag gccgttgagc accgccgccg caaggaatgg tgcatgcaag gagatggcgc    6180
ccaacagtcc cccggccacg gggcctgcca ccatacccac gccgaaacaa gcgctcatga    6240
gcccgaagtg gcgagcccga tcttccccat cggtgatgtc ggcgatatag gcgccagcaa    6300
ccgcacctgt ggcgccggtg atgccggcca cgatgcgtcc ggcgtagagg atcg          6354
```

```
<210> SEQ ID NO 12
<211> LENGTH: 294
<212> TYPE: DNA
<213> ORGANISM: artificial sequence
<220> FEATURE:
<223> OTHER INFORMATION: Chemically synthesized

<400> SEQUENCE: 12
```

```
atgtcgtact accatcacca tcaccatcac ctcgaatcaa caagtttgta caaaaaagca      60
ggctccgcgg ccgccccctt caccggatcc atcgaaggtc gtttccacga aaactggccg    120
tctgccggcg gtacctctac ttccaaagct tccaccacta cgacttctag caaaaccacc    180
actacatcct ctaagactac cacgactacc tccaaaacct ctactacctc tagctcctct    240
acgggcggcg ccactcacaa gacctctact cagcgtctgc tggctgcata atga          294
```

```
<210> SEQ ID NO 13
<211> LENGTH: 96
<212> TYPE: PRT
<213> ORGANISM: artificial sequence
<220> FEATURE:
<223> OTHER INFORMATION: Chemically synthesized

<400> SEQUENCE: 13
```

```
Met Ser Tyr Tyr His His His His His His Leu Glu Ser Thr Ser Leu
1               5                   10                  15

Tyr Lys Lys Ala Gly Ser Ala Ala Ala Pro Phe Thr Gly Ser Ile Glu
            20                  25                  30

Gly Arg Phe His Glu Asn Trp Pro Ser Ala Gly Gly Thr Ser Thr Ser
        35                  40                  45

Lys Ala Ser Thr Thr Thr Thr Ser Ser Lys Thr Thr Thr Thr Ser Ser
    50                  55                  60

Lys Thr Thr Thr Thr Thr Ser Lys Thr Ser Thr Ser Ser Ser Ser
65                  70                  75                  80

Thr Gly Gly Ala Thr His Lys Thr Ser Thr Gln Arg Leu Leu Ala Ala
                85                  90                  95
```

```
<210> SEQ ID NO 14
<211> LENGTH: 4945
<212> TYPE: DNA
<213> ORGANISM: artificial sequence
<220> FEATURE:
<223> OTHER INFORMATION: Plasmid

<400> SEQUENCE: 14
```

```
agatctcgat cccgcgaaat taatacgact cactataggg agaccacaac ggtttccctc      60
tagaaataat tttgtttaac tttaagaagg agatatacat atgtcgtact accatcacca    120
tcaccatcac ctcgaatcaa caagtttgta caaaaaagca ggctccgcgg ccgccccctt    180
```

-continued

```
caccggatcc atcgatccac gtttccacga aaactggccg tctgccggcg gtacctctac    240
ttccaaagct tccaccacta cgacttctag caaaaccacc actacatcct ctaagactac    300
cacgactacc tccaaaacct ctactacctc tagctcctct acgggcggcg ccactcacaa    360
gacctctact cagcgtctgc tggctgcata atgaaagggt gggcgcgccg acccagcttt    420
cttgtacaaa gtggttgatt cgaggctgct aacaaagccc gaaaggaagc tgagttggct    480
gctgccaccg ctgagcaata actagcataa cccttgggg cctctaaacg ggtcttgagg     540
ggttttttgc tgaaaggagg aactatatcc ggatatccac aggacgggtg tggtcgccat    600
gatcgcgtag tcgatagtgg ctccaagtag cgaagcgagc aggactgggc ggcggccaaa    660
gcggtcggac agtgctccga gaacgggtgc gcatagaaat tgcatcaacg catatagcgc    720
tagcagcacg ccatagtgac tggcgatgct gtcggaatgg acgatatccc gcaagaggcc    780
cggcagtacc ggcataacca agcctatgcc tacagcatcc agggtgacgg tgccgaggat    840
gacgatgagc gcattgttag atttcataca cggtgcctga ctgcgttagc aatttaactg    900
tgataaacta ccgcattaaa gcttatcgat gataagctgt caaacatgag aattcttgaa    960
gacgaaaggg cctcgtgata cgcctatttt tataggttaa tgtcatgata ataatggttt   1020
cttagacgtc aggtggcact tttcggggaa atgtgcgcgg aaccccatt tgtttatttt    1080 tctaaataca ttcaaatatg tatccgctca tgagacaata accctgataa atgcttcaat   1140
aatattgaaa aaggaagagt atgagtattc aacatttccg tgtcgccctt attccctttt   1200
ttgcggcatt ttgccttcct gttttttgctc acccagaaac gctggtgaaa gtaaaagatg   1260
ctgaagatca gttgggtgca cgagtgggtt acatcgaact ggatctcaac agcggtaaga   1320
tccttgagag ttttcgcccc gaagaacgtt ttccaatgat gagcactttt aaagttctgc   1380
tatgtggcgc ggtattatcc cgtgttgacg ccgggcaaga gcaactcggt cgccgcatac   1440
actattctca gaatgacttg gttgagtact caccagtcac agaaaagcat cttacggatg   1500
gcatgacagt aagagaatta tgcagtgctg ccataaccat gagtgataac actgcggcca   1560
acttacttct gacaacgatc ggaggaccga aggagctaac cgcttttttg cacaacatgg   1620
gggatcatgt aactcgcctt gatcgttggg aaccggagct gaatgaagcc ataccaaacg   1680
acgagcgtga caccacgatg cctgcagcaa tggcaacaac gttgcgcaaa ctattaactg   1740
gcgaactact tactctagct tcccggcaac aattaataga ctggatggag gcggataaag   1800
ttgcaggacc acttctgcgc tcggcccttc cggctggctg gtttattgct gataaatctg   1860
gagccggtga gcgtgggtct cgcggtatca ttgcagcact ggggccagat ggtaagccct   1920
cccgtatcgt agttatctac acgacgggga gtcaggcaac tatggatgaa cgaaatagac   1980
agatcgctga gataggtgcc tcactgatta agcattggta actgtcagac caagtttact   2040
catatatact ttagattgat ttaaaacttc atttttaatt taaaaggatc taggtgaaga   2100
tcctttttga taatctcatg accaaaatcc cttaacgtga gttttcgttc cactgagcgt   2160 cagacccgt agaaaagatc aaaggatctt cttgagatcc ttttttttctg cgcgtaatct    2220 gctgcttgca acaaaaaaa ccaccgctac cagcggtggt ttgtttgccg gatcaagagc    2280
taccaactct ttttccgaag gtaactggct tcagcagagc gcagatacca atactgtcc    2340 ttctagtgta gccgtagtta ggccaccact tcaagaactc tgtagcaccg cctacatacc   2400
tcgctctgct aatcctgtta ccagtggctg ctgccagtgg cgataagtcg tgtcttaccg   2460
ggttggactc aagacgatag ttaccggata aggcgcagcg gtcgggctga acggggggtt   2520
```

```
cgtgcacaca gcccagcttg gagcgaacga cctacaccga actgagatac ctacagcgtg    2580
agctatgaga aagcgccacg cttcccgaag ggagaaaggc ggacaggtat ccggtaagcg    2640
gcagggtcgg aacaggagag cgcacgaggg agcttccagg gggaaacgcc tggtatcttt    2700
atagtcctgt cgggtttcgc cacctctgac ttgagcgtcg attttttgtga tgctcgtcag   2760 gggggcggag cctatggaaa aacgccagca acgcggcctt tttacggttc ctggcctttt    2820
gctggccttt tgctcacatg ttctttcctg cgttatcccc tgattctgtg gataaccgta    2880
ttaccgcctt tgagtgagct gataccgctc gccgcagccg aacgaccgag cgcagcgagt    2940
cagtgagcga ggaagcggaa gagcgcctga tgcggtattt tctccttacg catctgtgcg    3000
gtatttcaca ccgcatatat ggtgcactct cagtacaatc tgctctgatg ccgcatagtt    3060
aagccagtat acactccgct atcgctacgt gactgggtca tggctgcgcc ccgacacccg    3120
ccaacacccg ctgacgcgcc ctgacgggct tgtctgctcc cggcatccgc ttacagacaa    3180
gctgtgaccg tctccgggag ctgcatgtgt cagaggtttt caccgtcatc accgaaacgc    3240
gcgaggcagc tgcggtaaag ctcatcagcg tggtcgtgaa gcgattcaca gatgtctgcc    3300
tgttcatccg cgtccagctc gttgagtttc tccagaagcg ttaatgtctg gcttctgata    3360
aagcgggcca tgttaagggc ggttttttcc tgtttggtca ctgatgcctc cgtgtaaggg    3420
ggatttctgt tcatgggggt aatgataccg atgaaacgag agaggatgct cacgatacgg    3480
gttactgatg atgaacatgc ccggttactg gaacgttgtg agggtaaaca actggcggta    3540
tggatgcggc gggaccagag aaaaatcact cagggtcaat gccagcgctt cgttaataca    3600
gatgtaggtg ttccacaggg tagccagcag catcctgcga tgcagatccg gaacataatg    3660
gtgcagggcg ctgacttccg cgtttccaga ctttacgaaa cacggaaacc gaagaccatt    3720
catgttgttg ctcaggtcgc agacgttttg cagcagcagt cgcttcacgt tcgctcgcgt    3780
atcggtgatt cattctgcta accagtaagg caaccccgcc agcctagccg ggtcctcaac    3840
gacaggagca cgatcatgcg cacccgtggc caggacccaa cgctgcccga tgcgccgc     3900 gtgcggctgc tggagatggc ggacgcgatg gatatgttct gccaagggtt ggtttgcgca    3960
ttcacagttc tccgcaagaa ttgattggct ccaattcttg gagtggtgaa tccgttagcg    4020
aggtgccgcc ggcttccatt caggtcgagg tggcccggct ccatgcaccg cgacgcaacg    4080
cggggaggca gacaaggtat agggcggcgc ctacaatcca tgccaacccg ttccatgtgc    4140
tcgccgaggc ggcataaatc gccgtgacga tcagcggtcc agtgatcgaa gttaggctgg    4200
taagagccgc gagcgatcct tgaagctgtc cctgatggtc gtcatctacc tgcctggaca    4260
gcatggcctg caacgcgggc atcccgatgc cgccggaagc gagaagaatc ataatgggga    4320
aggccatcca gcctcgcgtc gcgaacgcca gcaagacgta gcccagcgcg tcggccgcca    4380
tgccggcgat aatggcctgc ttctcgccga aacgtttggt ggcgggacca gtgacgaagg    4440
cttgagcgag ggcgtgcaag attccgaata ccgcaagcga caggccgatc atcgtcgcgc    4500
tccagcgaaa gcggtcctcg ccgaaaatga cccagagcgc tgccggcacc tgtcctacga    4560
gttgcatgat aaagaagaca gtcataagtg cggcgacgat agtcatgccc cgcgcccacc    4620
ggaaggagct gactgggttg aaggctctca agggcatcgg tcgatcgacg ctctccctta    4680
tgcgactcct gcattaggaa gcagcccagt agtaggttga ggccgttgag caccgccgcc    4740
gcaaggaatg gtgcatgcaa ggagatggcg cccaacagtc ccccggccac ggggcctgcc    4800
accatcccca cgccgaaaca gcgctcatg agcccgaagt ggcgagcccg atcttcccca    4860
tcggtgatgt cggcgatata ggcgccagca accgcacctg tggcgccggt gatgccggcc    4920
```

```
acgatgcgtc cggcgtagag gatcg                                              4945
```

<210> SEQ ID NO 15
<211> LENGTH: 45
<212> TYPE: DNA
<213> ORGANISM: artificial sequence
<220> FEATURE:
<223> OTHER INFORMATION: Primer

<400> SEQUENCE: 15

```
cccccttcacc ggatccatcg atccacgttt ccacgaaaac tggcc                       45
```

<210> SEQ ID NO 16
<211> LENGTH: 45
<212> TYPE: DNA
<213> ORGANISM: artificial sequence
<220> FEATURE:
<223> OTHER INFORMATION: Primer

<400> SEQUENCE: 16

```
ggccagtttt cgtggaaacg tggatcgatg gatccggtga agggg                        45
```

<210> SEQ ID NO 17
<211> LENGTH: 294
<212> TYPE: DNA
<213> ORGANISM: artificial sequence
<220> FEATURE:
<223> OTHER INFORMATION: Chemically synthesized

<400> SEQUENCE: 17

```
atgtcgtact accatcacca tcaccatcac ctcgaatcaa caagtttgta caaaaaagca        60
ggctccgcgg ccgccccctt caccggatcc atcgatccca gtttccacga aaactggccg       120
tctgccggcg gtacctctac ttccaaagct tccaccacta cgacttctag caaaaccacc       180
actacatcct ctaagactac cacgactacc tccaaaacct ctactacctc tagctcctct       240
acgggcggcg ccactcacaa gacctctact cagcgtctgc tggctgcata atga             294
```

<210> SEQ ID NO 18
<211> LENGTH: 96
<212> TYPE: PRT
<213> ORGANISM: artificial sequence
<220> FEATURE:
<223> OTHER INFORMATION: Chemically synthesized

<400> SEQUENCE: 18

```
Met Ser Tyr Tyr His His His His His His Leu Glu Ser Thr Ser Leu
  1               5                  10                  15

Tyr Lys Lys Ala Gly Ser Ala Ala Ala Pro Phe Thr Gly Ser Ile Asp
             20                  25                  30

Pro Arg Phe His Glu Asn Trp Pro Ser Ala Gly Gly Thr Ser Thr Ser
         35                  40                  45

Lys Ala Ser Thr Thr Thr Thr Ser Ser Lys Thr Thr Thr Thr Ser Ser
     50                  55                  60

Lys Thr Thr Thr Thr Thr Ser Lys Thr Ser Thr Ser Ser Ser Ser
 65                  70                  75                  80

Thr Gly Gly Ala Thr His Lys Thr Ser Thr Gln Arg Leu Leu Ala Ala
                 85                  90                  95
```

<210> SEQ ID NO 19
<211> LENGTH: 71
<212> TYPE: DNA

```
<213> ORGANISM: artificial sequence
<220> FEATURE:
<223> OTHER INFORMATION: Oligonucleotide used to prepare inclusion body
      tag

<400> SEQUENCE: 19
tatgagccgt cgtccgcgtc agttgcagca gcgtcagagc cgtcgtccgc gtcagttgca      60
gcagcgtcag g                                                          71

<210> SEQ ID NO 20
<211> LENGTH: 73
<212> TYPE: DNA
<213> ORGANISM: artificial sequence
<220> FEATURE:
<223> OTHER INFORMATION: Oligonucleotide used to prepare inclusion body
      tag

<400> SEQUENCE: 20
gatccctgac gctgctgcaa ctgacgcgga cgacggctct gacgctgctg caactgacgc      60
ggacgacggc tca                                                        73

<210> SEQ ID NO 21
<211> LENGTH: 59
<212> TYPE: DNA
<213> ORGANISM: artificial sequence
<220> FEATURE:
<223> OTHER INFORMATION: Oligonucleotide used to prepare inclusion body
      tag

<400> SEQUENCE: 21
tatgagccgt cgtccgcgtc agttgcagca gcgtcagcac caccagcagc agcaggaag      59

<210> SEQ ID NO 22
<211> LENGTH: 61
<212> TYPE: DNA
<213> ORGANISM: artificial sequence
<220> FEATURE:
<223> OTHER INFORMATION: Oligonucleotide used to prepare inclusion body
      tag

<400> SEQUENCE: 22
gatccttcct gctgctgctg gtggtgctga cgctgctgca actgacgcgg acgacggctc      60
a                                                                     61

<210> SEQ ID NO 23
<211> LENGTH: 104
<212> TYPE: DNA
<213> ORGANISM: artificial sequence
<220> FEATURE:
<223> OTHER INFORMATION: Oligonucleotide used to prepare inclusion body
      tag

<400> SEQUENCE: 23
tatgagccgt cgtccgcgtc agctgcagca gcgtcagagc cgtcgtccgc gtcagctgca      60
gcagcgtcag agccgtcgtc cgcgtcagct gcagcagcgt cagg                      104

<210> SEQ ID NO 24
<211> LENGTH: 106
<212> TYPE: DNA
<213> ORGANISM: artificial sequence
<220> FEATURE:
<223> OTHER INFORMATION: Oligonucleotide used to prepare inclusion body
      tag

<400> SEQUENCE: 24
```

```
gatccctgac gctgctgcag ctgacgcgga cgacggctct gacgctgctg cagctgacgc       60
ggacgacggc tctgacgctg ctgcagctga cgcggacgac ggctca                    106

<210> SEQ ID NO 25
<211> LENGTH: 40
<212> TYPE: DNA
<213> ORGANISM: artificial sequence
<220> FEATURE:
<223> OTHER INFORMATION: Oligonucleotide used to prepare inclusion body
      tag

<400> SEQUENCE: 25
gatccctgac gctgttgcag ctgacgcgga cgacggctca                            40

<210> SEQ ID NO 26
<211> LENGTH: 40
<212> TYPE: DNA
<213> ORGANISM: artificial sequence
<220> FEATURE:
<223> OTHER INFORMATION: Oligonucleotide used to prepare inclusion body
      tag

<400> SEQUENCE: 26
gatccctgac gctgttgcag ctgacgcgga cgacggctca                            40

<210> SEQ ID NO 27
<211> LENGTH: 116
<212> TYPE: DNA
<213> ORGANISM: artificial sequence
<220> FEATURE:
<223> OTHER INFORMATION: Oligonucleotide used to prepare inclusion body
      tag

<400> SEQUENCE: 27
tatgagccgt cgtccgcgtc agctgcaaca gcgtcaggac ccgagccgtc gtccgcgtca       60
gctgcaacag cgtcaggacc cgagccgtcg tccgcgtcag ctgcaacagc gtcagg         116

<210> SEQ ID NO 28
<211> LENGTH: 118
<212> TYPE: DNA
<213> ORGANISM: artificial sequence
<220> FEATURE:
<223> OTHER INFORMATION: Oligonucleotide used to prepare inclusion body
      tag

<400> SEQUENCE: 28
gatccctgac gctgttgcag ctgacgcgga cgacggctcg ggtcctgacg ctgttgcagc       60
tgacgcggac gacggctcgg gtcctgacgc tgttgcagct gacgcggacg acggctca       118

<210> SEQ ID NO 29
<211> LENGTH: 71
<212> TYPE: DNA
<213> ORGANISM: artificial sequence
<220> FEATURE:
<223> OTHER INFORMATION: Oligonucleotide used to prepare inclusion body
      tag

<400> SEQUENCE: 29
tatgagccgt cgtccggaac agctgcaaca gcgtcagagc cgtcgtccgg aacagctgca       60
acagcgtcag g                                                           71

<210> SEQ ID NO 30
<211> LENGTH: 73
```

```
<212> TYPE: DNA
<213> ORGANISM: artificial sequence
<220> FEATURE:
<223> OTHER INFORMATION: Oligonucleotide used to prepare inclusion body
      tag

<400> SEQUENCE: 30
gatccctgac gctgttgcag ctgttccgga cgacggctct gacgctgttg cagctgttcc    60
ggacgacggc tca                                                      73

<210> SEQ ID NO 31
<211> LENGTH: 71
<212> TYPE: DNA
<213> ORGANISM: artificial sequence
<220> FEATURE:
<223> OTHER INFORMATION: Oligonucleotide used to prepare inclusion body
      tag

<400> SEQUENCE: 31
tatgagccgt gaaccggaac agctgcaaca gcgtcagagc cgtcgtccgg aacagctgca    60
acagcgtcag g                                                        71

<210> SEQ ID NO 32
<211> LENGTH: 73
<212> TYPE: DNA
<213> ORGANISM: artificial sequence
<220> FEATURE:
<223> OTHER INFORMATION: Oligonucleotide used to prepare inclusion body
      tag

<400> SEQUENCE: 32
gatccctgac gctgttgcag ctgttccgga cgacggctct gacgctgttg cagctgttcc    60
ggttcacggc tca                                                      73

<210> SEQ ID NO 33
<211> LENGTH: 71
<212> TYPE: DNA
<213> ORGANISM: artificial sequence
<220> FEATURE:
<223> OTHER INFORMATION: Oligonucleotide used to prepare inclusion body
      tag

<400> SEQUENCE: 33
tatgagccgt gaaccggaac agctgcaaca gcgtcagagc cgtgaaccgg aacagctgca    60
acagcgtcag g                                                        71

<210> SEQ ID NO 34
<211> LENGTH: 73
<212> TYPE: DNA
<213> ORGANISM: artificial sequence
<220> FEATURE:
<223> OTHER INFORMATION: Oligonucleotide used to prepare inclusion body
      tag

<400> SEQUENCE: 34
gatccctgac gctgttgcag ctgttccggt tcacggctct gacgctgttg cagctgttcc    60
ggttcacggc tca                                                      73

<210> SEQ ID NO 35
<211> LENGTH: 71
<212> TYPE: DNA
<213> ORGANISM: artificial sequence
<220> FEATURE:
<223> OTHER INFORMATION: Oligonucleotide used to prepare inclusion body
``` tag

<400> SEQUENCE: 35
tatgagccgt gaaccggaac agctgcaaca gcgtcagagc cgtcgtccgg aacagctgca    60
acagcgtcag g                                                        71

<210> SEQ ID NO 36
<211> LENGTH: 73
<212> TYPE: DNA
<213> ORGANISM: artificial sequence
<220> FEATURE:
<223> OTHER INFORMATION: Oligonucleotide used to prepare inclusion body
      tag

<400> SEQUENCE: 36
gatccctgac gctgttgcag ctgttccgga cgacggctct gacgctgttg cagctgttcc    60
ggttcacggc tca                                                      73

<210> SEQ ID NO 37
<211> LENGTH: 71
<212> TYPE: DNA
<213> ORGANISM: artificial sequence
<220> FEATURE:
<223> OTHER INFORMATION: Oligonucleotide used to prepare inclusion body
      tag

<400> SEQUENCE: 37
tatgagccgt gaaccggaac agctgcaaca ggaacagagc cgtgaaccgg aacagctgca    60
acagcgtcag g                                                        71

<210> SEQ ID NO 38
<211> LENGTH: 73
<212> TYPE: DNA
<213> ORGANISM: artificial sequence
<220> FEATURE:
<223> OTHER INFORMATION: Oligonucleotide used to prepare inclusion body
      tag

<400> SEQUENCE: 38
gatccctgac gctgttgcag ctgttccggt tcacggctct gttcctgttg cagctgttcc    60
ggttcacggc tca                                                      73

<210> SEQ ID NO 39
<211> LENGTH: 71
<212> TYPE: DNA
<213> ORGANISM: artificial sequence
<220> FEATURE:
<223> OTHER INFORMATION: Oligonucleotide used to prepare inclusion body
      tag

<400> SEQUENCE: 39
tatgagccgt gaaccggaac agctgcaaca ggaacagagc cgtgaaccgg aacagctgca    60
acaggaacag g                                                        71

<210> SEQ ID NO 40
<211> LENGTH: 73
<212> TYPE: DNA
<213> ORGANISM: artificial sequence
<220> FEATURE:
<223> OTHER INFORMATION: Oligonucleotide used to prepare inclusion body
      tag

<400> SEQUENCE: 40

-continued

```
gatccctgtt cctgttgcag ctgttccggt tcacggctct gttcctgttg cagctgttcc    60
ggttcacggc tca                                                       73
```

<210> SEQ ID NO 41
<211> LENGTH: 71
<212> TYPE: DNA
<213> ORGANISM: artificial sequence
<220> FEATURE:
<223> OTHER INFORMATION: Oligonucleotide used to prepare inclusion body
      tag

<400> SEQUENCE: 41

```
tatgagccgt gaaccggaac agctgcaaca ggaacagagc gaagaaccgg aacagctgca    60
acaggaacag g                                                         71
```

<210> SEQ ID NO 42
<211> LENGTH: 73
<212> TYPE: DNA
<213> ORGANISM: artificial sequence
<220> FEATURE:
<223> OTHER INFORMATION: Oligonucleotide used to prepare inclusion body
      tag

<400> SEQUENCE: 42

```
gatccctgtt cctgttgcag ctgttccggt tcttcgctct gttcctgttg cagctgttcc    60
ggttcacggc tca                                                       73
```

<210> SEQ ID NO 43
<211> LENGTH: 71
<212> TYPE: DNA
<213> ORGANISM: artificial sequence
<220> FEATURE:
<223> OTHER INFORMATION: Oligonucleotide used to prepare inclusion body
      tag

<400> SEQUENCE: 43

```
tatgagcgaa gaaccggaac agctgcaaca ggaacagagc gaagaaccgg aacagctgca    60
acaggaacag g                                                         71
```

<210> SEQ ID NO 44
<211> LENGTH: 73
<212> TYPE: DNA
<213> ORGANISM: artificial sequence
<220> FEATURE:
<223> OTHER INFORMATION: Oligonucleotide used to prepare inclusion body
      tag

<400> SEQUENCE: 44

```
gatccctgtt cctgttgcag ctgttccggt tcttcgctct gttcctgttg cagctgttcc    60
ggttcttcgc tca                                                       73
```

<210> SEQ ID NO 45
<211> LENGTH: 74
<212> TYPE: DNA
<213> ORGANISM: artificial sequence
<220> FEATURE:
<223> OTHER INFORMATION: Oligonucleotide used to prepare inclusion body
      tag

<400> SEQUENCE: 45

```
tatgagccgt cgtccgcgtc agttgcagca gcgtcagagc gtcgtccgc gtcagttgca     60 gcagcgtcag gaag                                                      74
```

<210> SEQ ID NO 46
<211> LENGTH: 76
<212> TYPE: DNA
<213> ORGANISM: artificial sequence
<220> FEATURE:
<223> OTHER INFORMATION: Oligonucleotide used to prepare inclusion body
    tag

<400> SEQUENCE: 46
gatccttcct gacgctgctg caactgacgc ggacgacggc tctgacgctg ctgcaactga     60
cgcggacgac ggctca                                                    76

<210> SEQ ID NO 47
<211> LENGTH: 77
<212> TYPE: DNA
<213> ORGANISM: artificial sequence
<220> FEATURE:
<223> OTHER INFORMATION: Oligonucleotide used to prepare inclusion body
    tag

<400> SEQUENCE: 47
tatgagccgt cgtccgcgtc agttgcagca gcgtcagagc cgtcgtccgc gtcagttgca     60
gcagcgtcag gaagaag                                                   77

<210> SEQ ID NO 48
<211> LENGTH: 79
<212> TYPE: DNA
<213> ORGANISM: artificial sequence
<220> FEATURE:
<223> OTHER INFORMATION: Oligonucleotide used to prepare inclusion body
    tag

<400> SEQUENCE: 48
gatccttctt cctgacgctg ctgcaactga cgcggacgac ggctctgacg ctgctgcaac     60
tgacgcggac gacggctca                                                 79

<210> SEQ ID NO 49
<211> LENGTH: 80
<212> TYPE: DNA
<213> ORGANISM: artificial sequence
<220> FEATURE:
<223> OTHER INFORMATION: Oligonucleotide used to prepare inclusion body
    tag

<400> SEQUENCE: 49
tatgagccgt cgtccgcgtc agttgcagca gcgtcagagc cgtcgtccgc gtcagttgca     60
gcagcgtcag gaagaagaag                                                80

<210> SEQ ID NO 50
<211> LENGTH: 85
<212> TYPE: DNA
<213> ORGANISM: artificial sequence
<220> FEATURE:
<223> OTHER INFORMATION: Oligonucleotide used to prepare inclusion body
    tag

<400> SEQUENCE: 50
gatccttctt cttcttcctg acgctgctgc aactgacgcg gacgacggct ctgacgctgc     60
tgcaactgac gcggacgacg gctca                                          85

<210> SEQ ID NO 51
<211> LENGTH: 83
<212> TYPE: DNA

<210> SEQ ID NO 51
<211> LENGTH: (not shown here; inferred 83)
<212> TYPE: DNA
<213> ORGANISM: artificial sequence
<220> FEATURE:
<223> OTHER INFORMATION: Oligonucleotide used to prepare inclusion body tag

<400> SEQUENCE: 51

```
tatgagccgt cgtccgcgtc agttgcagca gcgtcagagc cgtcgtccgc gtcagttgca    60
gcagcgtcag gaagaagaag aag                                            83
```

<210> SEQ ID NO 52
<211> LENGTH: 85
<212> TYPE: DNA
<213> ORGANISM: artificial sequence
<220> FEATURE:
<223> OTHER INFORMATION: Oligonucleotide used to prepare inclusion body tag

<400> SEQUENCE: 52

```
gatccttctt cttcttcctg acgctgctgc aactgacgcg gacgacggct ctgacgctgc    60
tgcaactgac gcggacgacg gctca                                          85
```

<210> SEQ ID NO 53
<211> LENGTH: 89
<212> TYPE: DNA
<213> ORGANISM: artificial sequence
<220> FEATURE:
<223> OTHER INFORMATION: Oligonucleotide used to prepare inclusion body tag

<400> SEQUENCE: 53

```
tatgagccgt cgtccgcgtc agttgcagca gcgtcagagc cgtcgtccgc gtcagttgca    60
gcagcgtcag gaagaagaag aagaagaag                                      89
```

<210> SEQ ID NO 54
<211> LENGTH: 91
<212> TYPE: DNA
<213> ORGANISM: artificial sequence
<220> FEATURE:
<223> OTHER INFORMATION: Oligonucleotide used to prepare inclusion body tag

<400> SEQUENCE: 54

```
gatccttctt cttcttcttc ttcctgacgc tgctgcaact gacgcggacg acggctctga    60
cgctgctgca actgacgcgg acgacggctc a                                   91
```

<210> SEQ ID NO 55
<211> LENGTH: 95
<212> TYPE: DNA
<213> ORGANISM: artificial sequence
<220> FEATURE:
<223> OTHER INFORMATION: Oligonucleotide used to prepare inclusion body tag

<400> SEQUENCE: 55

```
tatgagccgt cgtccgcgtc agttgcagca gcgtcagagc cgtcgtccgc gtcagttgca    60
gcagcgtcag gaagaagaag aagaagaaga agaag                               95
```

<210> SEQ ID NO 56
<211> LENGTH: 97
<212> TYPE: DNA
<213> ORGANISM: artificial sequence
<220> FEATURE:
<223> OTHER INFORMATION: Oligonucleotide used to prepare inclusion body tag -continued

```
<400> SEQUENCE: 56
gatccttctt cttcttcttc ttcttcttcc tgacgctgct gcaactgacg cggacgacgg      60
ctctgacgct gctgcaactg acgcggacga cggctca                              97

<210> SEQ ID NO 57
<211> LENGTH: 98
<212> TYPE: DNA
<213> ORGANISM: artificial sequence
<220> FEATURE:
<223> OTHER INFORMATION: Oligonucleotide used to prepare inclusion body
      tag

<400> SEQUENCE: 57
tatgagccgt cgtccgcgtc agttgcagca gcgtcagagc cgtcgtccgc gtcagttgca      60
gcagcgtcag gaagaagaag aagaagaaga agaagaag                              98

<210> SEQ ID NO 58
<211> LENGTH: 100
<212> TYPE: DNA
<213> ORGANISM: artificial sequence
<220> FEATURE:
<223> OTHER INFORMATION: Oligonucleotide used to prepare inclusion body
      tag

<400> SEQUENCE: 58
gatccttctt cttcttcttc ttcttcttct tcctgacgct gctgcaactg acgcggacga      60
cggctctgac gctgctgcaa ctgacgcgga cgacggctca                           100

<210> SEQ ID NO 59
<211> LENGTH: 41
<212> TYPE: DNA
<213> ORGANISM: artificial sequence
<220> FEATURE:
<223> OTHER INFORMATION: Oligonucleotide used to prepare inclusion body
      tag

<400> SEQUENCE: 59
tatgagccgt cgtgatccgc gtcagctgca acagcgtcag g                          41

<210> SEQ ID NO 60
<211> LENGTH: 43
<212> TYPE: DNA
<213> ORGANISM: artificial sequence
<220> FEATURE:
<223> OTHER INFORMATION: Oligonucleotide used to prepare inclusion body
      tag

<400> SEQUENCE: 60
gatccctgac gctgttgcag ctgacgcgga tcacgacggc tca                        43

<210> SEQ ID NO 61
<211> LENGTH: 83
<212> TYPE: DNA
<213> ORGANISM: artificial sequence
<220> FEATURE:
<223> OTHER INFORMATION: Oligonucleotide used to prepare inclusion body
      tag

<400> SEQUENCE: 61
tatgagccgt cgtccgcgtc aggacccgct gcagcagcgt caggacccga gccgtcgtcc      60
gcgtcagctg cagcagcgtc agg                                              83
```

<210> SEQ ID NO 62
<211> LENGTH: 85
<212> TYPE: DNA
<213> ORGANISM: artificial sequence
<220> FEATURE:
<223> OTHER INFORMATION: Oligonucleotide used to prepare inclusion body tag

<400> SEQUENCE: 62
gatccctgac gctgctgcag ctgacgcgga cgacggctcg ggtcctgacg ctgctgcagc    60
gggtcctgac gcggacgacg gctca                                         85

<210> SEQ ID NO 63
<211> LENGTH: 89
<212> TYPE: DNA
<213> ORGANISM: artificial sequence
<220> FEATURE:
<223> OTHER INFORMATION: Oligonucleotide used to prepare inclusion body tag

<400> SEQUENCE: 63
tatgagccgt cgtccgcgtc aggacccgct gcagcagcgt caggacccga gccgtcgtcc    60
gcgtcaggac cgctgcagc agcgtcagg                                      89

<210> SEQ ID NO 64
<211> LENGTH: 91
<212> TYPE: DNA
<213> ORGANISM: artificial sequence
<220> FEATURE:
<223> OTHER INFORMATION: Oligonucleotide used to prepare inclusion body tag

<400> SEQUENCE: 64
gatccctgac gctgctgcag cgggtcctga cgcggacgac ggctcgggtc ctgacgctgc    60
tgcagcgggt cctgacgcgg acgacggctc a                                  91

<210> SEQ ID NO 65
<211> LENGTH: 68
<212> TYPE: DNA
<213> ORGANISM: artificial sequence
<220> FEATURE:
<223> OTHER INFORMATION: Oligonucleotide used to prepare inclusion body tag

<400> SEQUENCE: 65
tatgagccgt cgtccgcgtc agctgcagca gcgtcagagc ctgggttacg gtggtctgta    60
cggttacg                                                            68

<210> SEQ ID NO 66
<211> LENGTH: 70
<212> TYPE: DNA
<213> ORGANISM: artificial sequence
<220> FEATURE:
<223> OTHER INFORMATION: Oligonucleotide used to prepare inclusion body tag

<400> SEQUENCE: 66
gatccgtaac cgtacagacc accgtaaccc aggctctgac gctgctgcag ctgacgcgga    60
cgacggctca                                                          70

<210> SEQ ID NO 67
<211> LENGTH: 22
<212> TYPE: PRT
<213> ORGANISM: artificial sequence -continued

```
<220> FEATURE:
<223> OTHER INFORMATION: Inclusion body tag IBT-3

<400> SEQUENCE: 67

Ser Arg Arg Pro Arg Gln Leu Gln Gln Arg Gln Ser Arg Arg Pro Arg
1               5                   10                  15
Gln Leu Gln Gln Arg Gln
            20

<210> SEQ ID NO 68
<211> LENGTH: 18
<212> TYPE: PRT
<213> ORGANISM: artificial sequence
<220> FEATURE:
<223> OTHER INFORMATION: Inclusion body tag IBT-4

<400> SEQUENCE: 68

Ser Arg Arg Pro Arg Gln Leu Gln Gln Arg Gln His His Gln Gln Gln
1               5                   10                  15
Gln Glu

<210> SEQ ID NO 69
<211> LENGTH: 33
<212> TYPE: PRT
<213> ORGANISM: artificial sequence
<220> FEATURE:
<223> OTHER INFORMATION: Inclusion body tag IBT-23

<400> SEQUENCE: 69

Ser Arg Arg Pro Arg Gln Leu Gln Gln Arg Gln Ser Arg Arg Pro Arg
1               5                   10                  15
Gln Leu Gln Gln Arg Gln Ser Arg Arg Pro Arg Gln Leu Gln Gln Arg
            20                  25                  30
Gln

<210> SEQ ID NO 70
<211> LENGTH: 11
<212> TYPE: PRT
<213> ORGANISM: artificial sequence
<220> FEATURE:
<223> OTHER INFORMATION: Inclusion body tag IBT-24

<400> SEQUENCE: 70

Ser Arg Arg Pro Arg Gln Leu Gln Gln Arg Gln
1               5                   10

<210> SEQ ID NO 71
<211> LENGTH: 37
<212> TYPE: PRT
<213> ORGANISM: artificial sequence
<220> FEATURE:
<223> OTHER INFORMATION: Inclusion body tag IBT-25

<400> SEQUENCE: 71

Ser Arg Arg Pro Arg Gln Leu Gln Gln Arg Gln Asp Pro Ser Arg Arg
1               5                   10                  15
Pro Arg Gln Leu Gln Gln Arg Gln Asp Pro Ser Arg Arg Pro Arg Gln
            20                  25                  30
Leu Gln Gln Arg Gln
            35

<210> SEQ ID NO 72
<211> LENGTH: 22
```

<212> TYPE: PRT
<213> ORGANISM: artificial sequence
<220> FEATURE:
<223> OTHER INFORMATION: Inclusion body tag IBT-26

<400> SEQUENCE: 72

Ser Arg Arg Pro Glu Gln Leu Gln Gln Arg Gln Ser Arg Arg Pro Glu
1               5                   10                  15

Gln Leu Gln Gln Arg Gln
            20

<210> SEQ ID NO 73
<211> LENGTH: 22
<212> TYPE: PRT
<213> ORGANISM: artificial sequence
<220> FEATURE:
<223> OTHER INFORMATION: Inclusion body tag IBT-27

<400> SEQUENCE: 73

Ser Arg Glu Pro Glu Gln Leu Gln Gln Arg Gln Ser Arg Arg Pro Glu
1               5                   10                  15

Gln Leu Gln Gln Arg Gln
            20

<210> SEQ ID NO 74
<211> LENGTH: 22
<212> TYPE: PRT
<213> ORGANISM: artificial sequence
<220> FEATURE:
<223> OTHER INFORMATION: Inclusion body tag IBT-28

<400> SEQUENCE: 74

Ser Arg Glu Pro Glu Gln Leu Gln Gln Arg Gln Ser Arg Glu Pro Glu
1               5                   10                  15

Gln Leu Gln Gln Arg Gln
            20

<210> SEQ ID NO 75
<211> LENGTH: 22
<212> TYPE: PRT
<213> ORGANISM: artificial sequence
<220> FEATURE:
<223> OTHER INFORMATION: Inclusion body tag IBT-29

<400> SEQUENCE: 75

Ser Glu Glu Pro Glu Gln Leu Gln Gln Glu Gln Ser Arg Arg Pro Arg
1               5                   10                  15

Gln Leu Gln Gln Arg Gln
            20

<210> SEQ ID NO 76
<211> LENGTH: 22
<212> TYPE: PRT
<213> ORGANISM: artificial sequence
<220> FEATURE:
<223> OTHER INFORMATION: Inclusion body tag IBT-30

<400> SEQUENCE: 76

Ser Arg Glu Pro Glu Gln Leu Gln Gln Glu Gln Ser Arg Glu Pro Glu
1               5                   10                  15

Gln Leu Gln Gln Arg Gln
            20

<210> SEQ ID NO 77

```
<211> LENGTH: 22
<212> TYPE: PRT
<213> ORGANISM: artificial sequence
<220> FEATURE:
<223> OTHER INFORMATION: Inclusion body tag IBT-31

<400> SEQUENCE: 77

Ser Arg Glu Pro Glu Gln Leu Gln Gln Glu Gln Ser Arg Glu Pro Glu
1               5                   10                  15

Gln Leu Gln Gln Glu Gln
            20

<210> SEQ ID NO 78
<211> LENGTH: 22
<212> TYPE: PRT
<213> ORGANISM: artificial sequence
<220> FEATURE:
<223> OTHER INFORMATION: Inclusion body tag IBT-32

<400> SEQUENCE: 78

Ser Arg Glu Pro Glu Gln Leu Gln Gln Glu Gln Ser Glu Glu Pro Glu
1               5                   10                  15

Gln Leu Gln Gln Glu Gln
            20

<210> SEQ ID NO 79
<211> LENGTH: 22
<212> TYPE: PRT
<213> ORGANISM: artificial sequence
<220> FEATURE:
<223> OTHER INFORMATION: Inclusion body tag IBT-33

<400> SEQUENCE: 79

Ser Glu Glu Pro Glu Gln Leu Gln Gln Glu Gln Ser Glu Glu Pro Glu
1               5                   10                  15

Gln Leu Gln Gln Glu Gln
            20

<210> SEQ ID NO 80
<211> LENGTH: 23
<212> TYPE: PRT
<213> ORGANISM: artificial sequence
<220> FEATURE:
<223> OTHER INFORMATION: Inclusion body tag IBT-34

<400> SEQUENCE: 80

Ser Arg Arg Pro Arg Gln Leu Gln Gln Arg Gln Ser Arg Arg Pro Arg
1               5                   10                  15

Gln Leu Gln Gln Arg Gln Glu
            20

<210> SEQ ID NO 81
<211> LENGTH: 24
<212> TYPE: PRT
<213> ORGANISM: artificial sequence
<220> FEATURE:
<223> OTHER INFORMATION: Inclusion body tag IBT-35

<400> SEQUENCE: 81

Ser Arg Arg Pro Arg Gln Leu Gln Gln Arg Gln Ser Arg Arg Pro Arg
1               5                   10                  15

Gln Leu Gln Gln Arg Gln Glu Glu
            20
```

```
<210> SEQ ID NO 82
<211> LENGTH: 25
<212> TYPE: PRT
<213> ORGANISM: artificial sequence
<220> FEATURE:
<223> OTHER INFORMATION: Inclusion body tag IBT-36

<400> SEQUENCE: 82

Ser Arg Arg Pro Arg Gln Leu Gln Gln Arg Gln Ser Arg Arg Pro Arg
1               5                   10                  15

Gln Leu Gln Gln Arg Gln Glu Glu Glu
            20                  25

<210> SEQ ID NO 83
<211> LENGTH: 26
<212> TYPE: PRT
<213> ORGANISM: artificial sequence
<220> FEATURE:
<223> OTHER INFORMATION: Inclusion body tag IBT-37

<400> SEQUENCE: 83

Ser Arg Arg Pro Arg Gln Leu Gln Gln Arg Gln Ser Arg Arg Pro Arg
1               5                   10                  15

Gln Leu Gln Gln Arg Gln Glu Glu Glu Glu
            20                  25

<210> SEQ ID NO 84
<211> LENGTH: 28
<212> TYPE: PRT
<213> ORGANISM: artificial sequence
<220> FEATURE:
<223> OTHER INFORMATION: Inclusion body tag IBT-38

<400> SEQUENCE: 84

Ser Arg Arg Pro Arg Gln Leu Gln Gln Arg Gln Ser Arg Arg Pro Arg
1               5                   10                  15

Gln Leu Gln Gln Arg Gln Glu Glu Glu Glu Glu Glu
            20                  25

<210> SEQ ID NO 85
<211> LENGTH: 30
<212> TYPE: PRT
<213> ORGANISM: artificial sequence
<220> FEATURE:
<223> OTHER INFORMATION: Inclusion body tag IBT-39

<400> SEQUENCE: 85

Ser Arg Arg Pro Arg Gln Leu Gln Gln Arg Gln Ser Arg Arg Pro Arg
1               5                   10                  15

Gln Leu Gln Gln Arg Gln Glu Glu Glu Glu Glu Glu Glu Glu
            20                  25                  30

<210> SEQ ID NO 86
<211> LENGTH: 32
<212> TYPE: PRT
<213> ORGANISM: artificial sequence
<220> FEATURE:
<223> OTHER INFORMATION: Inclusion body tag IBT-40

<400> SEQUENCE: 86

Ser Arg Arg Pro Arg Gln Leu Gln Gln Arg Gln Ser Arg Arg Pro Arg
1               5                   10                  15

Gln Leu Gln Gln Arg Gln Glu Glu Glu Glu Glu Glu Glu Glu Glu Glu
            20                  25                  30
```

```
<210> SEQ ID NO 87
<211> LENGTH: 12
<212> TYPE: PRT
<213> ORGANISM: artificial sequence
<220> FEATURE:
<223> OTHER INFORMATION: Inclusion body tag IBT-54

<400> SEQUENCE: 87

Ser Arg Arg Asp Pro Arg Gln Leu Gln Gln Arg Gln
1               5                   10

<210> SEQ ID NO 88
<211> LENGTH: 26
<212> TYPE: PRT
<213> ORGANISM: artificial sequence
<220> FEATURE:
<223> OTHER INFORMATION: Inclusion body tag IBT-89

<400> SEQUENCE: 88

Ser Arg Arg Pro Arg Gln Asp Pro Leu Gln Gln Arg Gln Asp Pro Ser
1               5                   10                  15

Arg Arg Pro Arg Gln Leu Gln Gln Arg Gln
            20                  25

<210> SEQ ID NO 89
<211> LENGTH: 28
<212> TYPE: PRT
<213> ORGANISM: artificial sequence
<220> FEATURE:
<223> OTHER INFORMATION: Inclusion body tag IBT-90

<400> SEQUENCE: 89

Ser Arg Arg Pro Arg Gln Asp Pro Leu Gln Gln Arg Gln Asp Pro Ser
1               5                   10                  15

Arg Arg Pro Arg Gln Asp Pro Leu Gln Gln Arg Gln
            20                  25

<210> SEQ ID NO 90
<211> LENGTH: 21
<212> TYPE: PRT
<213> ORGANISM: artificial sequence
<220> FEATURE:
<223> OTHER INFORMATION: Inclusion body tag IBT-95

<400> SEQUENCE: 90

Ser Arg Arg Pro Arg Gln Leu Gln Gln Arg Gln Ser Leu Gly Tyr Gly
1               5                   10                  15

Gly Leu Tyr Gly Tyr
            20

<210> SEQ ID NO 91
<211> LENGTH: 246
<212> TYPE: DNA
<213> ORGANISM: artificial sequence
<220> FEATURE:
<223> OTHER INFORMATION: Chemically synthesized
<220> FEATURE:
<221> NAME/KEY: CDS
<222> LOCATION: (1)..(246)

<400> SEQUENCE: 91 atg agc cgt cgt ccg cgt cag ctg caa cag cgt cag gga tcc atc gat        48
Met Ser Arg Arg Pro Arg Gln Leu Gln Gln Arg Gln Gly Ser Ile Asp
1               5                   10                  15 cca cgt ttc cac gaa aac tgg ccg tct gcc ggc ggt acc tct act tcc        96
```

```
Pro Arg Phe His Glu Asn Trp Pro Ser Ala Gly Gly Thr Ser Thr Ser
         20                  25                  30 aaa gct tcc acc act acg act tct agc aaa acc acc act aca tcc tct      144
Lys Ala Ser Thr Thr Thr Thr Ser Ser Lys Thr Thr Thr Thr Ser Ser
         35                  40                  45 aag act acc acg act acc tcc aaa acc tct act acc tct agc tcc tct      192
Lys Thr Thr Thr Thr Thr Ser Lys Thr Ser Thr Thr Ser Ser Ser Ser
 50                  55                  60 acg ggc ggc gcc act cac aag acc tct act cag cgt ctg ctg gct gca      240
Thr Gly Gly Ala Thr His Lys Thr Ser Thr Gln Arg Leu Leu Ala Ala
 65                  70                  75                  80 taa tga                                                              246
```

<210> SEQ ID NO 92
<211> LENGTH: 80
<212> TYPE: PRT
<213> ORGANISM: artificial sequence
<220> FEATURE:
<223> OTHER INFORMATION: Synthetic Construct

<400> SEQUENCE: 92

```
Met Ser Arg Arg Pro Arg Gln Leu Gln Gln Arg Gln Gly Ser Ile Asp
 1               5                  10                  15

Pro Arg Phe His Glu Asn Trp Pro Ser Ala Gly Gly Thr Ser Thr Ser
                 20                  25                  30

Lys Ala Ser Thr Thr Thr Thr Ser Ser Lys Thr Thr Thr Thr Ser Ser
             35                  40                  45

Lys Thr Thr Thr Thr Thr Ser Lys Thr Ser Thr Thr Ser Ser Ser Ser
 50                  55                  60

Thr Gly Gly Ala Thr His Lys Thr Ser Thr Gln Arg Leu Leu Ala Ala
 65                  70                  75                  80
```

<210> SEQ ID NO 93
<211> LENGTH: 249
<212> TYPE: DNA
<213> ORGANISM: artificial sequence
<220> FEATURE:
<223> OTHER INFORMATION: Chemically synthesized
<220> FEATURE:
<221> NAME/KEY: CDS
<222> LOCATION: (1)..(249)

<400> SEQUENCE: 93

```
atg agc cgt cgt gat ccg cgt cag ctg caa cag cgt cag gga tcc atc       48
Met Ser Arg Arg Asp Pro Arg Gln Leu Gln Gln Arg Gln Gly Ser Ile
 1               5                  10                  15 gat cca cgt ttc cac gaa aac tgg ccg tct gcc ggc ggt acc tct act       96
Asp Pro Arg Phe His Glu Asn Trp Pro Ser Ala Gly Gly Thr Ser Thr
                 20                  25                  30 tcc aaa gct tcc acc act acg act tct agc aaa acc act aca tcc           144
Ser Lys Ala Ser Thr Thr Thr Thr Ser Ser Lys Thr Thr Thr Thr Ser
             35                  40                  45 tct aag act acc acg act acc tcc aaa acc tct act acc tct agc tcc       192
Ser Lys Thr Thr Thr Thr Thr Ser Lys Thr Ser Thr Thr Ser Ser Ser
 50                  55                  60 tct acg ggc ggc gcc act cac aag acc tct act cag cgt ctg ctg gct       240
Ser Thr Gly Gly Ala Thr His Lys Thr Ser Thr Gln Arg Leu Leu Ala
 65                  70                  75                  80 gca taa tga                                                            249
Ala
```

<210> SEQ ID NO 94
<211> LENGTH: 81
<212> TYPE: PRT
<213> ORGANISM: artificial sequence
<220> FEATURE:
<223> OTHER INFORMATION: Synthetic Construct

<400> SEQUENCE: 94

Met Ser Arg Arg Asp Pro Arg Gln Leu Gln Gln Arg Gln Gly Ser Ile
1               5                   10                  15

Asp Pro Arg Phe His Glu Asn Trp Pro Ser Ala Gly Gly Thr Ser Thr
            20                  25                  30

Ser Lys Ala Ser Thr Thr Thr Thr Ser Ser Lys Thr Thr Thr Thr Ser
        35                  40                  45

Ser Lys Thr Thr Thr Thr Thr Ser Lys Thr Ser Thr Thr Ser Ser Ser
    50                  55                  60

Ser Thr Gly Gly Ala Thr His Lys Thr Ser Thr Gln Arg Leu Leu Ala
65                  70                  75                  80

Ala

<210> SEQ ID NO 95
<211> LENGTH: 324
<212> TYPE: DNA
<213> ORGANISM: artificial sequence
<220> FEATURE:
<223> OTHER INFORMATION: Chemically synthesized
<220> FEATURE:
<221> NAME/KEY: CDS
<222> LOCATION: (1)..(324)

<400> SEQUENCE: 95 atg agc cgt cgt ccg cgt cag ctg caa cag cgt cag gac ccg agc cgt        48
Met Ser Arg Arg Pro Arg Gln Leu Gln Gln Arg Gln Asp Pro Ser Arg
1               5                   10                  15 cgt ccg cgt cag ctg caa cag cgt cag gac ccg agc cgt cgt ccg cgt        96
Arg Pro Arg Gln Leu Gln Gln Arg Gln Asp Pro Ser Arg Arg Pro Arg
            20                  25                  30 cag ctg caa cag cgt cag gga tcc atc gat cca cgt ttc cac gaa aac       144
Gln Leu Gln Gln Arg Gln Gly Ser Ile Asp Pro Arg Phe His Glu Asn
        35                  40                  45 tgg ccg tct gcc ggc ggt acc tct act tcc aaa gct tcc acc act acg       192
Trp Pro Ser Ala Gly Gly Thr Ser Thr Ser Lys Ala Ser Thr Thr Thr
    50                  55                  60 act tct agc aaa acc acc act aca tcc tct aag act acc acg act acc       240
Thr Ser Ser Lys Thr Thr Thr Thr Ser Ser Lys Thr Thr Thr Thr Thr
65                  70                  75                  80 tcc aaa acc tct act acc tct agc tcc tct acg ggc ggc gcc act cac       288
Ser Lys Thr Ser Thr Thr Ser Ser Ser Thr Gly Gly Ala Thr His
                85                  90                  95 aag acc tct act cag cgt ctg ctg gct gca taa tga                       324
Lys Thr Ser Thr Gln Arg Leu Leu Ala Ala
            100                 105

<210> SEQ ID NO 96
<211> LENGTH: 106
<212> TYPE: PRT
<213> ORGANISM: artificial sequence
<220> FEATURE:
<223> OTHER INFORMATION: Synthetic Construct

<400> SEQUENCE: 96

Met Ser Arg Arg Pro Arg Gln Leu Gln Gln Arg Gln Asp Pro Ser Arg
1               5                   10                  15

```
Arg Pro Arg Gln Leu Gln Gln Arg Gln Asp Pro Ser Arg Arg Pro Arg
            20                  25                  30

Gln Leu Gln Gln Arg Gln Gly Ser Ile Asp Pro Arg Phe His Glu Asn
        35                  40                  45

Trp Pro Ser Ala Gly Gly Thr Ser Thr Ser Lys Ala Ser Thr Thr Thr
    50                  55                  60

Thr Ser Ser Lys Thr Thr Thr Thr Ser Ser Lys Thr Thr Thr Thr Thr
65                  70                  75                  80

Ser Lys Thr Ser Thr Thr Ser Ser Ser Thr Gly Gly Ala Thr His
                85                  90                  95

Lys Thr Ser Thr Gln Arg Leu Leu Ala Ala
            100                 105
```

```
<210> SEQ ID NO 97
<211> LENGTH: 279
<212> TYPE: DNA
<213> ORGANISM: artificial sequence
<220> FEATURE:
<223> OTHER INFORMATION: Chemically synthesized
<220> FEATURE:
<221> NAME/KEY: CDS
<222> LOCATION: (1)..(279)

<400> SEQUENCE: 97 atg agc gaa gaa ccg gaa cag ctg caa cag gaa cag agc cgt cgt ccg    48
Met Ser Glu Glu Pro Glu Gln Leu Gln Gln Glu Gln Ser Arg Arg Pro
1               5                   10                  15 cgt cag ctg caa cag cgt cag gga tcc atc gat cca cgt ttc cac gaa    96
Arg Gln Leu Gln Gln Arg Gln Gly Ser Ile Asp Pro Arg Phe His Glu
            20                  25                  30 aac tgg ccg tct gcc ggc ggt acc tct act tcc aaa gct tcc acc act    144
Asn Trp Pro Ser Ala Gly Gly Thr Ser Thr Ser Lys Ala Ser Thr Thr
        35                  40                  45 acg act tct agc aaa acc acc act aca tcc tct aag act acc acg act    192
Thr Thr Ser Ser Lys Thr Thr Thr Thr Ser Ser Lys Thr Thr Thr Thr
    50                  55                  60 acc tcc aaa acc tct act acc tct agc tcc tct acg ggc ggc gcc act    240
Thr Ser Lys Thr Ser Thr Thr Ser Ser Ser Thr Gly Gly Ala Thr
65                  70                  75                  80 cac aag acc tct act cag cgt ctg ctg gct gca taa tga                279
His Lys Thr Ser Thr Gln Arg Leu Leu Ala Ala
                85                  90
```

```
<210> SEQ ID NO 98
<211> LENGTH: 91
<212> TYPE: PRT
<213> ORGANISM: artificial sequence
<220> FEATURE:
<223> OTHER INFORMATION: Synthetic Construct

<400> SEQUENCE: 98

Met Ser Glu Glu Pro Glu Gln Leu Gln Gln Glu Gln Ser Arg Arg Pro
1               5                   10                  15

Arg Gln Leu Gln Gln Arg Gln Gly Ser Ile Asp Pro Arg Phe His Glu
            20                  25                  30

Asn Trp Pro Ser Ala Gly Gly Thr Ser Thr Ser Lys Ala Ser Thr Thr
        35                  40                  45

Thr Thr Ser Ser Lys Thr Thr Thr Thr Ser Ser Lys Thr Thr Thr Thr
    50                  55                  60

Thr Ser Lys Thr Ser Thr Thr Ser Ser Ser Thr Gly Gly Ala Thr
65                  70                  75                  80
```

His Lys Thr Ser Thr Gln Arg Leu Leu Ala Ala
            85                  90

<210> SEQ ID NO 99
<211> LENGTH: 276
<212> TYPE: DNA
<213> ORGANISM: artificial sequence
<220> FEATURE:
<223> OTHER INFORMATION: Chemically synthesized
<220> FEATURE:
<221> NAME/KEY: CDS
<222> LOCATION: (1)..(276)

<400> SEQUENCE: 99

| atg agc cgt cgt ccg cgt cag ctg cag cag cgt cag agc ctg ggt tac | 48 |
| Met Ser Arg Arg Pro Arg Gln Leu Gln Gln Arg Gln Ser Leu Gly Tyr | |
| 1               5                   10                  15     | |

| ggt ggt ctg tac ggt tac gga tcc atc gat cca cgt ttc cac gaa aac | 96 |
| Gly Gly Leu Tyr Gly Tyr Gly Ser Ile Asp Pro Arg Phe His Glu Asn | |
|             20                  25                  30         | |

| tgg ccg tct gcc ggc ggt acc tct act tcc aaa gct tcc acc act acg | 144 |
| Trp Pro Ser Ala Gly Gly Thr Ser Thr Ser Lys Ala Ser Thr Thr Thr | |
|         35                  40                  45             | |

| act tct agc aaa acc acc act aca tcc tct aag act acc acg act acc | 192 |
| Thr Ser Ser Lys Thr Thr Thr Thr Ser Ser Lys Thr Thr Thr Thr Thr | |
| 50                  55                  60                     | |

| tcc aaa acc tct act acc tct agc tcc tct acg ggc ggc gcc act cac | 240 |
| Ser Lys Thr Ser Thr Thr Ser Ser Ser Ser Thr Gly Gly Ala Thr His | |
| 65                  70                  75                  80 | |

| aag acc tct act cag cgt ctg ctg gct gca taa tga                | 276 |
| Lys Thr Ser Thr Gln Arg Leu Leu Ala Ala                        | |
|             85                  90                             | |

<210> SEQ ID NO 100
<211> LENGTH: 90
<212> TYPE: PRT
<213> ORGANISM: artificial sequence
<220> FEATURE:
<223> OTHER INFORMATION: Synthetic Construct

<400> SEQUENCE: 100

Met Ser Arg Arg Pro Arg Gln Leu Gln Gln Arg Gln Ser Leu Gly Tyr
1               5                   10                  15

Gly Gly Leu Tyr Gly Tyr Gly Ser Ile Asp Pro Arg Phe His Glu Asn
            20                  25                  30

Trp Pro Ser Ala Gly Gly Thr Ser Thr Ser Lys Ala Ser Thr Thr Thr
        35                  40                  45

Thr Ser Ser Lys Thr Thr Thr Thr Ser Ser Lys Thr Thr Thr Thr Thr
    50                  55                  60

Ser Lys Thr Ser Thr Thr Ser Ser Ser Ser Thr Gly Gly Ala Thr His
65                  70                  75                  80

Lys Thr Ser Thr Gln Arg Leu Leu Ala Ala
            85                  90

<210> SEQ ID NO 101
<211> LENGTH: 279
<212> TYPE: DNA
<213> ORGANISM: artificial sequence
<220> FEATURE:
<223> OTHER INFORMATION: Chemically synthesized
<220> FEATURE:
<221> NAME/KEY: CDS

<222> LOCATION: (1)..(279)

<400> SEQUENCE: 101

| | | | | | | | | | | | | | | | | |
|---|---|---|---|---|---|---|---|---|---|---|---|---|---|---|---|---|
| atg | agc | cgt | cgt | ccg | cgt | cag | ttg | cag | cag | cgt | cag | agc | cgt | ccg | | 48 |
| Met | Ser | Arg | Arg | Pro | Arg | Gln | Leu | Gln | Gln | Arg | Gln | Ser | Arg | Pro | | |
| 1 | | | | 5 | | | | | 10 | | | | | 15 | | |

| cgt | cag | ttg | cag | cag | cgt | cag | gga | tcc | atc | gat | cca | cgt | ttc | cac | gaa | 96 |
|---|---|---|---|---|---|---|---|---|---|---|---|---|---|---|---|---|
| Arg | Gln | Leu | Gln | Gln | Arg | Gln | Gly | Ser | Ile | Asp | Pro | Arg | Phe | His | Glu | |
| | | 20 | | | | | 25 | | | | | 30 | | | | |

| aac | tgg | ccg | tct | gcc | ggc | ggt | acc | tct | act | tcc | aaa | gct | tcc | acc | act | 144 |
|---|---|---|---|---|---|---|---|---|---|---|---|---|---|---|---|---|
| Asn | Trp | Pro | Ser | Ala | Gly | Gly | Thr | Ser | Thr | Ser | Lys | Ala | Ser | Thr | Thr | |
| | 35 | | | | | 40 | | | | | 45 | | | | | |

| acg | act | tct | agc | aaa | acc | act | aca | tcc | tct | aag | act | acc | acg | act | | 192 |
|---|---|---|---|---|---|---|---|---|---|---|---|---|---|---|---|---|
| Thr | Thr | Ser | Ser | Lys | Thr | Thr | Thr | Ser | Ser | Lys | Thr | Thr | Thr | Thr | | |
| 50 | | | | | 55 | | | | | 60 | | | | | | |

| acc | tcc | aaa | acc | tct | act | acc | tct | agc | tcc | tct | acg | ggc | ggc | gcc | act | 240 |
|---|---|---|---|---|---|---|---|---|---|---|---|---|---|---|---|---|
| Thr | Ser | Lys | Thr | Ser | Thr | Thr | Ser | Ser | Ser | Ser | Thr | Gly | Gly | Ala | Thr | |
| 65 | | | | | 70 | | | | | 75 | | | | | 80 | |

| cac | aag | acc | tct | act | cag | cgt | ctg | ctg | gct | gca | taa | tga | | | | 279 |
|---|---|---|---|---|---|---|---|---|---|---|---|---|---|---|---|---|
| His | Lys | Thr | Ser | Thr | Gln | Arg | Leu | Leu | Ala | Ala | | | | | | |
| | | | | 85 | | | | | 90 | | | | | | | |

<210> SEQ ID NO 102
<211> LENGTH: 91
<212> TYPE: PRT
<213> ORGANISM: artificial sequence
<220> FEATURE:
<223> OTHER INFORMATION: Synthetic Construct

<400> SEQUENCE: 102

Met Ser Arg Arg Pro Arg Gln Leu Gln Gln Arg Gln Ser Arg Pro
1               5                   10                  15

Arg Gln Leu Gln Gln Arg Gln Gly Ser Ile Asp Pro Arg Phe His Glu
            20                  25                  30

Asn Trp Pro Ser Ala Gly Gly Thr Ser Thr Ser Lys Ala Ser Thr Thr
        35                  40                  45

Thr Thr Ser Ser Lys Thr Thr Thr Ser Ser Lys Thr Thr Thr Thr
    50                  55                  60

Thr Ser Lys Thr Ser Thr Thr Ser Ser Ser Ser Thr Gly Gly Ala Thr
65                  70                  75                  80

His Lys Thr Ser Thr Gln Arg Leu Leu Ala Ala
                85                  90

<210> SEQ ID NO 103
<211> LENGTH: 267
<212> TYPE: DNA
<213> ORGANISM: artificial sequence
<220> FEATURE:
<223> OTHER INFORMATION: Chemically synthesized
<220> FEATURE:
<221> NAME/KEY: CDS
<222> LOCATION: (1)..(267)

<400> SEQUENCE: 103

| atg | agc | cgt | cgt | ccg | cgt | cag | ttg | cag | cag | cgt | cag | cac | cac | cag | cag | 48 |
|---|---|---|---|---|---|---|---|---|---|---|---|---|---|---|---|---|
| Met | Ser | Arg | Arg | Pro | Arg | Gln | Leu | Gln | Gln | Arg | Gln | His | His | Gln | Gln | |
| 1 | | | | 5 | | | | | 10 | | | | | 15 | | |

| cag | cag | gaa | gga | tcc | atc | gat | cca | cgt | ttc | cac | gaa | aac | tgg | ccg | tct | 96 |
|---|---|---|---|---|---|---|---|---|---|---|---|---|---|---|---|---|
| Gln | Gln | Glu | Gly | Ser | Ile | Asp | Pro | Arg | Phe | His | Glu | Asn | Trp | Pro | Ser | |
| | | | 20 | | | | | 25 | | | | | 30 | | | |

| gcc | ggc | ggt | acc | tct | act | tcc | aaa | gct | tcc | acc | act | acg | act | tct | agc | 144 |
|---|---|---|---|---|---|---|---|---|---|---|---|---|---|---|---|---|
| Ala | Gly | Gly | Thr | Ser | Thr | Ser | Lys | Ala | Ser | Thr | Thr | Thr | Thr | Ser | Ser | |

```
aaa acc acc act aca tcc tct aag act acc acg act acc tcc aaa acc      192
Lys Thr Thr Thr Ser Ser Lys Thr Thr Thr Thr Ser Lys Thr
 50                  55                  60 tct act acc tct agc tcc tct acg ggc ggc gcc act cac aag acc tct      240
Ser Thr Thr Ser Ser Ser Ser Thr Gly Gly Ala Thr His Lys Thr Ser
 65                  70                  75                  80 act cag cgt ctg ctg gct gca taa tga                                  267
Thr Gln Arg Leu Leu Ala Ala
                85
```

<210> SEQ ID NO 104
<211> LENGTH: 87
<212> TYPE: PRT
<213> ORGANISM: artificial sequence
<220> FEATURE:
<223> OTHER INFORMATION: Synthetic Construct

<400> SEQUENCE: 104

```
Met Ser Arg Arg Pro Arg Gln Leu Gln Gln Arg Gln His His Gln Gln
 1               5                  10                  15

Gln Gln Glu Gly Ser Ile Asp Pro Arg Phe His Glu Asn Trp Pro Ser
            20                  25                  30

Ala Gly Gly Thr Ser Thr Ser Lys Ala Ser Thr Thr Thr Ser Ser
        35                  40                  45

Lys Thr Thr Thr Thr Ser Ser Lys Thr Thr Thr Thr Ser Lys Thr
 50                  55                  60

Ser Thr Thr Ser Ser Ser Ser Thr Gly Gly Ala Thr His Lys Thr Ser
 65                  70                  75                  80

Thr Gln Arg Leu Leu Ala Ala
                85
```

<210> SEQ ID NO 105
<211> LENGTH: 312
<212> TYPE: DNA
<213> ORGANISM: artificial sequence
<220> FEATURE:
<223> OTHER INFORMATION: Chemically synthesized
<220> FEATURE:
<221> NAME/KEY: CDS
<222> LOCATION: (1)..(312)

<400> SEQUENCE: 105

```
atg agc cgt cgt ccg cgt cag ctg cag cag cgt cag agc cgt cgt ccg       48
Met Ser Arg Arg Pro Arg Gln Leu Gln Gln Arg Gln Ser Arg Arg Pro
 1               5                  10                  15 cgt cag ctg cag cag cgt cag agc cgt cgt ccg cgt cag ctg cag cag       96
Arg Gln Leu Gln Gln Arg Gln Ser Arg Arg Pro Arg Gln Leu Gln Gln
            20                  25                  30 cgt cag gga tcc atc gat cca cgt ttc cac gaa aac tgg ccg tct gcc      144
Arg Gln Gly Ser Ile Asp Pro Arg Phe His Glu Asn Trp Pro Ser Ala
        35                  40                  45 ggc ggt acc tct act tcc aaa gct tcc acc act acg act tct agc aaa      192
Gly Gly Thr Ser Thr Ser Lys Ala Ser Thr Thr Thr Ser Ser Lys
 50                  55                  60 acc acc act aca tcc tct aag act acc acg act acc tcc aaa acc tct      240
Thr Thr Thr Thr Ser Ser Lys Thr Thr Thr Thr Ser Lys Thr Ser
 65                  70                  75                  80 act acc tct agc tcc tct acg ggc ggc gcc act cac aag acc tct act      288
Thr Thr Ser Ser Ser Ser Thr Gly Gly Ala Thr His Lys Thr Ser Thr
                85                  90                  95
```

```
                                                            -continued
cag cgt ctg ctg gct gca taa tga                                    312
Gln Arg Leu Leu Ala Ala
        100

<210> SEQ ID NO 106
<211> LENGTH: 102
<212> TYPE: PRT
<213> ORGANISM: artificial sequence
<220> FEATURE:
<223> OTHER INFORMATION: Synthetic Construct

<400> SEQUENCE: 106

Met Ser Arg Arg Pro Arg Gln Leu Gln Gln Arg Gln Ser Arg Arg Pro
1               5                   10                  15

Arg Gln Leu Gln Gln Arg Gln Ser Arg Arg Pro Arg Gln Leu Gln Gln
            20                  25                  30

Arg Gln Gly Ser Ile Asp Pro Arg Phe His Glu Asn Trp Pro Ser Ala
        35                  40                  45

Gly Gly Thr Ser Thr Ser Lys Ala Ser Thr Thr Thr Ser Ser Lys
    50                  55                  60

Thr Thr Thr Thr Ser Ser Lys Thr Thr Thr Thr Thr Ser Lys Thr Ser
65                  70                  75                  80

Thr Thr Ser Ser Ser Ser Thr Gly Gly Ala Thr His Lys Thr Ser Thr
                85                  90                  95

Gln Arg Leu Leu Ala Ala
        100

<210> SEQ ID NO 107
<211> LENGTH: 279
<212> TYPE: DNA
<213> ORGANISM: artificial sequence
<220> FEATURE:
<223> OTHER INFORMATION: Chemically synthesized
<220> FEATURE:
<221> NAME/KEY: CDS
<222> LOCATION: (1)..(279)

<400> SEQUENCE: 107 atg agc cgt gaa ccg gaa cag ctg caa cag cgt cag agc cgt cgt ccg     48
Met Ser Arg Glu Pro Glu Gln Leu Gln Gln Arg Gln Ser Arg Arg Pro
1               5                   10                  15 gaa cag ctg caa cag cgt cag gga tcc atc gat cca cgt ttc cac gaa     96
Glu Gln Leu Gln Gln Arg Gln Gly Ser Ile Asp Pro Arg Phe His Glu
            20                  25                  30 aac tgg ccg tct gcc ggc ggt acc tct act tcc aaa gct tcc acc act    144
Asn Trp Pro Ser Ala Gly Gly Thr Ser Thr Ser Lys Ala Ser Thr Thr
        35                  40                  45 acg act tct agc aaa acc acc act aca tcc tct aag act acc acg act    192
Thr Thr Ser Ser Lys Thr Thr Thr Thr Ser Ser Lys Thr Thr Thr Thr
    50                  55                  60 acc tcc aaa acc tct act acc tct agc tcc tct acg ggc ggc gcc act    240
Thr Ser Lys Thr Ser Thr Thr Ser Ser Ser Ser Thr Gly Gly Ala Thr
65                  70                  75                  80 cac aag acc tct act cag cgt ctg ctg gct gca taa tga                279
His Lys Thr Ser Thr Gln Arg Leu Leu Ala Ala
                85                  90

<210> SEQ ID NO 108
<211> LENGTH: 91
<212> TYPE: PRT
<213> ORGANISM: artificial sequence
<220> FEATURE:
<223> OTHER INFORMATION: Synthetic Construct
```

<400> SEQUENCE: 108

| Met | Ser | Arg | Glu | Pro | Glu | Gln | Leu | Gln | Gln | Arg | Gln | Ser | Arg | Arg | Pro |
|---|---|---|---|---|---|---|---|---|---|---|---|---|---|---|---|
| 1 | | | | 5 | | | | | 10 | | | | | 15 | |

| Glu | Gln | Leu | Gln | Gln | Arg | Gln | Gly | Ser | Ile | Asp | Pro | Arg | Phe | His | Glu |
|---|---|---|---|---|---|---|---|---|---|---|---|---|---|---|---|
| | | | 20 | | | | | 25 | | | | | 30 | | |

| Asn | Trp | Pro | Ser | Ala | Gly | Gly | Thr | Ser | Thr | Ser | Lys | Ala | Ser | Thr | Thr |
|---|---|---|---|---|---|---|---|---|---|---|---|---|---|---|---|
| | | 35 | | | | | 40 | | | | | 45 | | | |

| Thr | Thr | Ser | Ser | Lys | Thr | Thr | Thr | Thr | Ser | Ser | Lys | Thr | Thr | Thr | Thr |
|---|---|---|---|---|---|---|---|---|---|---|---|---|---|---|---|
| 50 | | | | | 55 | | | | | 60 | | | | | |

| Thr | Ser | Lys | Thr | Ser | Thr | Thr | Ser | Ser | Ser | Ser | Thr | Gly | Gly | Ala | Thr |
|---|---|---|---|---|---|---|---|---|---|---|---|---|---|---|---|
| 65 | | | | | 70 | | | | | 75 | | | | | 80 |

| His | Lys | Thr | Ser | Thr | Gln | Arg | Leu | Leu | Ala | Ala |
|---|---|---|---|---|---|---|---|---|---|---|
| | | | | 85 | | | | | 90 | |

<210> SEQ ID NO 109
<211> LENGTH: 279
<212> TYPE: DNA
<213> ORGANISM: artificial sequence
<220> FEATURE:
<223> OTHER INFORMATION: Chemically synthesized
<220> FEATURE:
<221> NAME/KEY: CDS
<222> LOCATION: (1)..(279)

<400> SEQUENCE: 109

| atg | agc | cgt | gaa | ccg | gaa | cag | ctg | caa | cag | cgt | cag | agc | cgt | gaa | ccg | 48 |
|---|---|---|---|---|---|---|---|---|---|---|---|---|---|---|---|---|
| Met | Ser | Arg | Glu | Pro | Glu | Gln | Leu | Gln | Gln | Arg | Gln | Ser | Arg | Glu | Pro | |
| 1 | | | | 5 | | | | | 10 | | | | | 15 | | |

| gaa | cag | ctg | caa | cag | cgt | cag | gga | tcc | atc | gat | cca | cgt | ttc | cac | gaa | 96 |
|---|---|---|---|---|---|---|---|---|---|---|---|---|---|---|---|---|
| Glu | Gln | Leu | Gln | Gln | Arg | Gln | Gly | Ser | Ile | Asp | Pro | Arg | Phe | His | Glu | |
| | | | 20 | | | | | 25 | | | | | 30 | | | |

| aac | tgg | ccg | tct | gcc | ggc | ggt | acc | tct | act | tcc | aaa | gct | tcc | acc | act | 144 |
|---|---|---|---|---|---|---|---|---|---|---|---|---|---|---|---|---|
| Asn | Trp | Pro | Ser | Ala | Gly | Gly | Thr | Ser | Thr | Ser | Lys | Ala | Ser | Thr | Thr | |
| | | 35 | | | | | 40 | | | | | 45 | | | | |

| acg | act | tct | agc | aaa | acc | act | aca | tcc | tct | aag | act | acc | acg | act | 192 |
|---|---|---|---|---|---|---|---|---|---|---|---|---|---|---|---|
| Thr | Thr | Ser | Ser | Lys | Thr | Thr | Thr | Thr | Ser | Ser | Lys | Thr | Thr | Thr | Thr |
| 50 | | | | | 55 | | | | | 60 | | | | | |

| acc | tcc | aaa | acc | tct | act | acc | tct | agc | tcc | tct | acg | ggc | ggc | gcc | act | 240 |
|---|---|---|---|---|---|---|---|---|---|---|---|---|---|---|---|---|
| Thr | Ser | Lys | Thr | Ser | Thr | Thr | Ser | Ser | Ser | Ser | Thr | Gly | Gly | Ala | Thr | |
| 65 | | | | | 70 | | | | | 75 | | | | | 80 | |

| cac | aag | acc | tct | act | cag | cgt | ctg | ctg | gct | gca | taa | tga | 279 |
|---|---|---|---|---|---|---|---|---|---|---|---|---|---|
| His | Lys | Thr | Ser | Thr | Gln | Arg | Leu | Leu | Ala | Ala | | | |
| | | | | 85 | | | | | 90 | | | | |

<210> SEQ ID NO 110
<211> LENGTH: 91
<212> TYPE: PRT
<213> ORGANISM: artificial sequence
<220> FEATURE:
<223> OTHER INFORMATION: Synthetic Construct

<400> SEQUENCE: 110

| Met | Ser | Arg | Glu | Pro | Glu | Gln | Leu | Gln | Gln | Arg | Gln | Ser | Arg | Glu | Pro |
|---|---|---|---|---|---|---|---|---|---|---|---|---|---|---|---|
| 1 | | | | 5 | | | | | 10 | | | | | 15 | |

| Glu | Gln | Leu | Gln | Gln | Arg | Gln | Gly | Ser | Ile | Asp | Pro | Arg | Phe | His | Glu |
|---|---|---|---|---|---|---|---|---|---|---|---|---|---|---|---|
| | | | 20 | | | | | 25 | | | | | 30 | | |

| Asn | Trp | Pro | Ser | Ala | Gly | Gly | Thr | Ser | Thr | Ser | Lys | Ala | Ser | Thr | Thr |
|---|---|---|---|---|---|---|---|---|---|---|---|---|---|---|---|
| | | 35 | | | | | 40 | | | | | 45 | | | |

| Thr | Thr | Ser | Ser | Lys | Thr | Thr | Thr | Thr | Ser | Ser | Lys | Thr | Thr | Thr | Thr |
|---|---|---|---|---|---|---|---|---|---|---|---|---|---|---|---|
| 50 | | | | | 55 | | | | | 60 | | | | | |

```
Thr Ser Lys Thr Ser Thr Thr Ser Ser Ser Thr Gly Gly Ala Thr
 65                 70                  75                  80

His Lys Thr Ser Thr Gln Arg Leu Leu Ala Ala
                 85                  90

<210> SEQ ID NO 111
<211> LENGTH: 291
<212> TYPE: DNA
<213> ORGANISM: artificial sequence
<220> FEATURE:
<223> OTHER INFORMATION: Chemically synthesized
<220> FEATURE:
<221> NAME/KEY: CDS
<222> LOCATION: (1)..(291)

<400> SEQUENCE: 111 atg agc cgt cgt ccg cgt cag ttg cag cag cgt cag agc cgt cgt ccg      48
Met Ser Arg Arg Pro Arg Gln Leu Gln Gln Arg Gln Ser Arg Arg Pro
 1               5                  10                  15 cgt cag ttg cag cag cgt cag gaa gaa gaa gaa gga tcc atc gat cca      96
Arg Gln Leu Gln Gln Arg Gln Glu Glu Glu Glu Gly Ser Ile Asp Pro
             20                  25                  30 cgt ttc cac gaa aac tgg ccg tct gcc ggc ggt acc tct act tcc aaa     144
Arg Phe His Glu Asn Trp Pro Ser Ala Gly Gly Thr Ser Thr Ser Lys
         35                  40                  45 gct tcc acc act acg act tct agc aaa acc acc act aca tcc tct aag     192
Ala Ser Thr Thr Thr Thr Ser Ser Lys Thr Thr Thr Thr Ser Ser Lys
     50                  55                  60 act acc acg act acc tcc aaa acc tct act acc tct agc tcc tct acg     240
Thr Thr Thr Thr Ser Lys Thr Ser Thr Thr Ser Ser Ser Thr
 65                 70                  75                  80 ggc ggc gcc act cac aag acc tct act cag cgt ctg ctg gct gca taa     288
Gly Gly Ala Thr His Lys Thr Ser Thr Gln Arg Leu Leu Ala Ala
                 85                  90                  95 tga                                                                  291

<210> SEQ ID NO 112
<211> LENGTH: 95
<212> TYPE: PRT
<213> ORGANISM: artificial sequence
<220> FEATURE:
<223> OTHER INFORMATION: Synthetic Construct

<400> SEQUENCE: 112

Met Ser Arg Arg Pro Arg Gln Leu Gln Gln Arg Gln Ser Arg Arg Pro
 1               5                  10                  15

Arg Gln Leu Gln Gln Arg Gln Glu Glu Glu Glu Gly Ser Ile Asp Pro
             20                  25                  30

Arg Phe His Glu Asn Trp Pro Ser Ala Gly Gly Thr Ser Thr Ser Lys
         35                  40                  45

Ala Ser Thr Thr Thr Thr Ser Ser Lys Thr Thr Thr Thr Ser Ser Lys
     50                  55                  60

Thr Thr Thr Thr Thr Ser Lys Thr Ser Thr Thr Ser Ser Ser Thr
 65                 70                  75                  80

Gly Gly Ala Thr His Lys Thr Ser Thr Gln Arg Leu Leu Ala Ala
                 85                  90                  95

<210> SEQ ID NO 113
<211> LENGTH: 279
<212> TYPE: DNA
<213> ORGANISM: artificial sequence
```

```
<220> FEATURE:
<223> OTHER INFORMATION: Chemically synthesized
<220> FEATURE:
<221> NAME/KEY: CDS
<222> LOCATION: (1)..(279)

<400> SEQUENCE: 113 atg agc cgt cgt ccg gaa cag ctg caa cag cgt cag agc cgt cgt ccg      48
Met Ser Arg Arg Pro Glu Gln Leu Gln Gln Arg Gln Ser Arg Arg Pro
1               5                  10                  15 gaa cag ctg caa cag cgt cag gga tcc atc gat cca cgt ttc cac gaa      96
Glu Gln Leu Gln Gln Arg Gln Gly Ser Ile Asp Pro Arg Phe His Glu
                20                  25                  30 aac tgg ccg tct gcc ggc ggt acc tct act tcc aaa gct tcc acc act     144
Asn Trp Pro Ser Ala Gly Gly Thr Ser Thr Ser Lys Ala Ser Thr Thr
            35                  40                  45 acg act tct agc aaa acc acc act aca tcc tct aag act acc acg act     192
Thr Thr Ser Ser Lys Thr Thr Thr Thr Ser Ser Lys Thr Thr Thr Thr
    50                  55                  60 acc tcc aaa acc tct act acc tct agc tcc tct acg ggc ggc gcc act     240
Thr Ser Lys Thr Ser Thr Thr Ser Ser Ser Thr Gly Gly Ala Thr
65                  70                  75                  80 cac aag acc tct act cag cgt ctg ctg gct gca taa tga                 279
His Lys Thr Ser Thr Gln Arg Leu Leu Ala Ala
                85                  90

<210> SEQ ID NO 114
<211> LENGTH: 91
<212> TYPE: PRT
<213> ORGANISM: artificial sequence
<220> FEATURE:
<223> OTHER INFORMATION: Synthetic Construct

<400> SEQUENCE: 114

Met Ser Arg Arg Pro Glu Gln Leu Gln Gln Arg Gln Ser Arg Arg Pro
1               5                  10                  15

Glu Gln Leu Gln Gln Arg Gln Gly Ser Ile Asp Pro Arg Phe His Glu
                20                  25                  30

Asn Trp Pro Ser Ala Gly Gly Thr Ser Thr Ser Lys Ala Ser Thr Thr
            35                  40                  45

Thr Thr Ser Ser Lys Thr Thr Thr Thr Ser Ser Lys Thr Thr Thr Thr
    50                  55                  60

Thr Ser Lys Thr Ser Thr Thr Ser Ser Ser Thr Gly Gly Ala Thr
65                  70                  75                  80

His Lys Thr Ser Thr Gln Arg Leu Leu Ala Ala
                85                  90

<210> SEQ ID NO 115
<211> LENGTH: 279
<212> TYPE: DNA
<213> ORGANISM: artificial sequence
<220> FEATURE:
<223> OTHER INFORMATION: Chemically synthesized
<220> FEATURE:
<221> NAME/KEY: CDS
<222> LOCATION: (1)..(279)

<400> SEQUENCE: 115 atg agc cgt gaa ccg gaa cag ctg caa cag gaa cag agc cgt gaa ccg      48
Met Ser Arg Glu Pro Glu Gln Leu Gln Gln Glu Gln Ser Arg Glu Pro
1               5                  10                  15 gaa cag ctg caa cag cgt cag gga tcc atc gat cca cgt ttc cac gaa      96
Glu Gln Leu Gln Gln Arg Gln Gly Ser Ile Asp Pro Arg Phe His Glu
```

```
                    20                  25                  30
aac tgg ccg tct gcc ggc ggt acc tct act tcc aaa gct tcc acc act        144
Asn Trp Pro Ser Ala Gly Gly Thr Ser Thr Ser Lys Ala Ser Thr Thr
        35                  40                  45 acg act tct agc aaa acc acc act aca tcc tct aag act acc acg act        192
Thr Thr Ser Ser Lys Thr Thr Thr Thr Ser Ser Lys Thr Thr Thr Thr
50                  55                  60 acc tcc aaa acc tct act acc tct agc tcc tct acg ggc ggc gcc act        240
Thr Ser Lys Thr Ser Thr Thr Ser Ser Ser Ser Thr Gly Gly Ala Thr
65                  70                  75                  80 cac aag acc tct act cag cgt ctg ctg gct gca taa tga                    279
His Lys Thr Ser Thr Gln Arg Leu Leu Ala Ala
                85                  90

<210> SEQ ID NO 116
<211> LENGTH: 91
<212> TYPE: PRT
<213> ORGANISM: artificial sequence
<220> FEATURE:
<223> OTHER INFORMATION: Synthetic Construct

<400> SEQUENCE: 116

Met Ser Arg Glu Pro Glu Gln Leu Gln Gln Glu Gln Ser Arg Glu Pro
1               5                   10                  15

Glu Gln Leu Gln Gln Arg Gln Gly Ser Ile Asp Pro Arg Phe His Glu
            20                  25                  30

Asn Trp Pro Ser Ala Gly Gly Thr Ser Thr Ser Lys Ala Ser Thr Thr
        35                  40                  45

Thr Thr Ser Ser Lys Thr Thr Thr Thr Ser Ser Lys Thr Thr Thr Thr
    50                  55                  60

Thr Ser Lys Thr Ser Thr Thr Ser Ser Ser Ser Thr Gly Gly Ala Thr
65                  70                  75                  80

His Lys Thr Ser Thr Gln Arg Leu Leu Ala Ala
                85                  90

<210> SEQ ID NO 117
<211> LENGTH: 279
<212> TYPE: DNA
<213> ORGANISM: artificial sequence
<220> FEATURE:
<223> OTHER INFORMATION: Chemically synthesized
<220> FEATURE:
<221> NAME/KEY: CDS
<222> LOCATION: (1)..(279)

<400> SEQUENCE: 117 atg agc cgt gaa ccg gaa cag ctg caa cag gaa cag agc cgt gaa ccg        48
Met Ser Arg Glu Pro Glu Gln Leu Gln Gln Glu Gln Ser Arg Glu Pro
1               5                   10                  15 gaa cag ctg caa cag gaa cag gga tcc atc gat cca cgt ttc cac gaa        96
Glu Gln Leu Gln Gln Glu Gln Gly Ser Ile Asp Pro Arg Phe His Glu
            20                  25                  30 aac tgg ccg tct gcc ggc ggt acc tct act tcc aaa gct tcc acc act        144
Asn Trp Pro Ser Ala Gly Gly Thr Ser Thr Ser Lys Ala Ser Thr Thr
        35                  40                  45 acg act tct agc aaa acc acc act aca tcc tct aag act acc acg act        192
Thr Thr Ser Ser Lys Thr Thr Thr Thr Ser Ser Lys Thr Thr Thr Thr
    50                  55                  60 acc tcc aaa acc tct act acc tct agc tcc tct acg ggc ggc gcc act        240
Thr Ser Lys Thr Ser Thr Thr Ser Ser Ser Ser Thr Gly Gly Ala Thr
65                  70                  75                  80
```

```
cac aag acc tct act cag cgt ctg ctg gct gca taa tga            279
His Lys Thr Ser Thr Gln Arg Leu Leu Ala Ala
             85                  90
```

<210> SEQ ID NO 118
<211> LENGTH: 91
<212> TYPE: PRT
<213> ORGANISM: artificial sequence
<220> FEATURE:
<223> OTHER INFORMATION: Synthetic Construct

<400> SEQUENCE: 118

```
Met Ser Arg Glu Pro Glu Gln Leu Gln Gln Glu Gln Ser Arg Glu Pro
1               5                   10                  15

Glu Gln Leu Gln Gln Glu Gln Gly Ser Ile Asp Pro Arg Phe His Glu
            20                  25                  30

Asn Trp Pro Ser Ala Gly Gly Thr Ser Thr Ser Lys Ala Ser Thr Thr
        35                  40                  45

Thr Thr Ser Ser Lys Thr Thr Thr Ser Ser Lys Thr Thr Thr Thr
    50                  55                  60

Thr Ser Lys Thr Ser Thr Thr Ser Ser Ser Thr Gly Gly Ala Thr
65                  70                  75                  80

His Lys Thr Ser Thr Gln Arg Leu Leu Ala Ala
            85                  90
```

<210> SEQ ID NO 119
<211> LENGTH: 285
<212> TYPE: DNA
<213> ORGANISM: artificial sequence
<220> FEATURE:
<223> OTHER INFORMATION: Chemically synthesized
<220> FEATURE:
<221> NAME/KEY: CDS
<222> LOCATION: (1)..(285)

<400> SEQUENCE: 119

```
atg agc cgt cgt ccg cgt cag ttg cag cag cgt cag agc cgt cgt ccg      48
Met Ser Arg Arg Pro Arg Gln Leu Gln Gln Arg Gln Ser Arg Arg Pro
1               5                   10                  15 cgt cag ttg cag cag cgt cag gaa gaa gga tcc atc gat cca cgt ttc      96
Arg Gln Leu Gln Gln Arg Gln Glu Glu Gly Ser Ile Asp Pro Arg Phe
            20                  25                  30 cac gaa aac tgg ccg tct gcc ggc ggt acc tct act tcc aaa gct tcc     144
His Glu Asn Trp Pro Ser Ala Gly Gly Thr Ser Thr Ser Lys Ala Ser
        35                  40                  45 acc act acg act tct agc aaa acc acc act aca tcc tct aag act acc     192
Thr Thr Thr Thr Ser Ser Lys Thr Thr Thr Thr Ser Ser Lys Thr Thr
    50                  55                  60 acg act acc tcc aaa acc tct act acc tct agc tcc tct acg ggc ggc     240
Thr Thr Thr Ser Lys Thr Ser Thr Thr Ser Ser Ser Ser Thr Gly Gly
65                  70                  75                  80 gcc act cac aag acc tct act cag cgt ctg ctg gct gca taa tga         285
Ala Thr His Lys Thr Ser Thr Gln Arg Leu Leu Ala Ala
                85                  90
```

<210> SEQ ID NO 120
<211> LENGTH: 93
<212> TYPE: PRT
<213> ORGANISM: artificial sequence
<220> FEATURE:
<223> OTHER INFORMATION: Synthetic Construct

<400> SEQUENCE: 120

Met Ser Arg Arg Pro Arg Gln Leu Gln Gln Arg Gln Ser Arg Arg Pro
1               5                   10                  15

Arg Gln Leu Gln Gln Arg Gln Glu Glu Glu Gly Ser Ile Asp Pro Arg Phe
            20                  25                  30

His Glu Asn Trp Pro Ser Ala Gly Gly Thr Ser Thr Ser Lys Ala Ser
        35                  40                  45

Thr Thr Thr Thr Ser Ser Lys Thr Thr Thr Thr Ser Ser Lys Thr Thr
    50                  55                  60

Thr Thr Thr Ser Lys Thr Ser Thr Thr Ser Ser Ser Thr Gly Gly
65                  70                  75                  80

Ala Thr His Lys Thr Ser Thr Gln Arg Leu Leu Ala Ala
                85                  90

<210> SEQ ID NO 121
<211> LENGTH: 288
<212> TYPE: DNA
<213> ORGANISM: artificial sequence
<220> FEATURE:
<223> OTHER INFORMATION: Chemically synthesized
<220> FEATURE:
<221> NAME/KEY: CDS
<222> LOCATION: (1)..(288)

<400> SEQUENCE: 121 atg agc cgt cgt ccg cgt cag ttg cag cag cgt cag agc cgt cgt ccg        48
Met Ser Arg Arg Pro Arg Gln Leu Gln Gln Arg Gln Ser Arg Arg Pro
1               5                   10                  15 cgt cag ttg cag cag cgt cag gaa gaa gaa gga tcc atc gat cca cgt        96
Arg Gln Leu Gln Gln Arg Gln Glu Glu Glu Gly Ser Ile Asp Pro Arg
            20                  25                  30 ttc cac gaa aac tgg ccg tct gcc ggc ggt acc tct act tcc aaa gct       144
Phe His Glu Asn Trp Pro Ser Ala Gly Gly Thr Ser Thr Ser Lys Ala
        35                  40                  45 tcc acc act acg act tct agc aaa acc acc act aca tcc tct aag act       192
Ser Thr Thr Thr Thr Ser Ser Lys Thr Thr Thr Thr Ser Ser Lys Thr
    50                  55                  60 acc acg act acc tcc aaa acc tct act acc tct agc tcc tct acg ggc       240
Thr Thr Thr Thr Ser Lys Thr Ser Thr Thr Ser Ser Ser Thr Gly
65                  70                  75                  80 ggc gcc act cac aag acc tct act cag cgt ctg ctg gct gca taa tga       288
Gly Ala Thr His Lys Thr Ser Thr Gln Arg Leu Leu Ala Ala
                85                  90

<210> SEQ ID NO 122
<211> LENGTH: 94
<212> TYPE: PRT
<213> ORGANISM: artificial sequence
<220> FEATURE:
<223> OTHER INFORMATION: Synthetic Construct

<400> SEQUENCE: 122

Met Ser Arg Arg Pro Arg Gln Leu Gln Gln Arg Gln Ser Arg Arg Pro
1               5                   10                  15

Arg Gln Leu Gln Gln Arg Gln Glu Glu Glu Gly Ser Ile Asp Pro Arg
            20                  25                  30

Phe His Glu Asn Trp Pro Ser Ala Gly Gly Thr Ser Thr Ser Lys Ala
        35                  40                  45

Ser Thr Thr Thr Thr Ser Ser Lys Thr Thr Thr Thr Ser Ser Lys Thr
    50                  55                  60

Thr Thr Thr Thr Ser Lys Thr Ser Thr Thr Ser Ser Ser Thr Gly
65                  70                  75                  80

Gly Ala Thr His Lys Thr Ser Thr Gln Arg Leu Leu Ala Ala
                85                  90

<210> SEQ ID NO 123
<211> LENGTH: 297
<212> TYPE: DNA
<213> ORGANISM: artificial sequence
<220> FEATURE:
<223> OTHER INFORMATION: Chemically synthesized
<220> FEATURE:
<221> NAME/KEY: CDS
<222> LOCATION: (1)..(297)

<400> SEQUENCE: 123

```
atg agc cgt cgt ccg cgt cag ttg cag cag cgt cag agc cgt cgt ccg      48
Met Ser Arg Arg Pro Arg Gln Leu Gln Gln Arg Gln Ser Arg Arg Pro
1               5                   10                  15 cgt cag ttg cag cag cgt cag gaa gaa gaa gaa gaa gaa gga tcc atc      96
Arg Gln Leu Gln Gln Arg Gln Glu Glu Glu Glu Glu Glu Gly Ser Ile
            20                  25                  30 gat cca cgt ttc cac gaa aac tgg ccg tct gcc ggc ggt acc tct act     144
Asp Pro Arg Phe His Glu Asn Trp Pro Ser Ala Gly Gly Thr Ser Thr
        35                  40                  45 tcc aaa gct tcc acc act acg act tct agc aaa acc acc act aca tcc     192
Ser Lys Ala Ser Thr Thr Thr Thr Ser Ser Lys Thr Thr Thr Thr Ser
    50                  55                  60 tct aag act acc acg act acc tcc aaa acc tct act acc tct agc tcc     240
Ser Lys Thr Thr Thr Thr Thr Ser Lys Thr Ser Thr Thr Ser Ser Ser
65                  70                  75                  80 tct acg ggc ggc gcc act cac aag acc tct act cag cgt ctg ctg gct     288
Ser Thr Gly Gly Ala Thr His Lys Thr Ser Thr Gln Arg Leu Leu Ala
                85                  90                  95 gca taa tga                                                          297
Ala
```

<210> SEQ ID NO 124
<211> LENGTH: 97
<212> TYPE: PRT
<213> ORGANISM: artificial sequence
<220> FEATURE:
<223> OTHER INFORMATION: Synthetic Construct

<400> SEQUENCE: 124

Met Ser Arg Arg Pro Arg Gln Leu Gln Gln Arg Gln Ser Arg Arg Pro
1               5                   10                  15

Arg Gln Leu Gln Gln Arg Gln Glu Glu Glu Glu Glu Glu Gly Ser Ile
            20                  25                  30

Asp Pro Arg Phe His Glu Asn Trp Pro Ser Ala Gly Gly Thr Ser Thr
        35                  40                  45

Ser Lys Ala Ser Thr Thr Thr Thr Ser Ser Lys Thr Thr Thr Thr Ser
    50                  55                  60

Ser Lys Thr Thr Thr Thr Thr Ser Lys Thr Ser Thr Thr Ser Ser Ser
65                  70                  75                  80

Ser Thr Gly Gly Ala Thr His Lys Thr Ser Thr Gln Arg Leu Leu Ala
                85                  90                  95

Ala

<210> SEQ ID NO 125
<211> LENGTH: 291
<212> TYPE: DNA
<213> ORGANISM: artificial sequence

```
<220> FEATURE:
<223> OTHER INFORMATION: Chemically synthesized
<220> FEATURE:
<221> NAME/KEY: CDS
<222> LOCATION: (1)..(291)

<400> SEQUENCE: 125 atg agc cgt cgt ccg cgt cag gac ccg ctg cag cag cgt cag gac ccg      48
Met Ser Arg Arg Pro Arg Gln Asp Pro Leu Gln Gln Arg Gln Asp Pro
1               5                   10                  15 agc cgt cgt ccg cgt cag ctg cag cag cgt cag gga tcc atc gat cca      96
Ser Arg Arg Pro Arg Gln Leu Gln Gln Arg Gln Gly Ser Ile Asp Pro
            20                  25                  30 cgt ttc cac gaa aac tgg ccg tct gcc ggc ggt acc tct act tcc aaa     144
Arg Phe His Glu Asn Trp Pro Ser Ala Gly Gly Thr Ser Thr Ser Lys
        35                  40                  45 gct tcc acc act acg act tct agc aaa acc acc act aca tcc tct aag     192
Ala Ser Thr Thr Thr Thr Ser Ser Lys Thr Thr Thr Thr Ser Ser Lys
50                  55                  60 act acc acg act acc tcc aaa acc tct act acc tct agc tcc tct acg     240
Thr Thr Thr Thr Thr Ser Lys Thr Ser Thr Thr Ser Ser Ser Ser Thr
65                  70                  75                  80 ggc ggc gcc act cac aag acc tct act cag cgt ctg ctg gct gca taa     288
Gly Gly Ala Thr His Lys Thr Ser Thr Gln Arg Leu Leu Ala Ala
                85                  90                  95 tga                                                                  291

<210> SEQ ID NO 126
<211> LENGTH: 95
<212> TYPE: PRT
<213> ORGANISM: artificial sequence
<220> FEATURE:
<223> OTHER INFORMATION: Synthetic Construct

<400> SEQUENCE: 126

Met Ser Arg Arg Pro Arg Gln Asp Pro Leu Gln Gln Arg Gln Asp Pro
1               5                   10                  15

Ser Arg Arg Pro Arg Gln Leu Gln Gln Arg Gln Gly Ser Ile Asp Pro
            20                  25                  30

Arg Phe His Glu Asn Trp Pro Ser Ala Gly Gly Thr Ser Thr Ser Lys
        35                  40                  45

Ala Ser Thr Thr Thr Thr Ser Ser Lys Thr Thr Thr Thr Ser Ser Lys
50                  55                  60

Thr Thr Thr Thr Thr Ser Lys Thr Ser Thr Thr Ser Ser Ser Ser Thr
65                  70                  75                  80

Gly Gly Ala Thr His Lys Thr Ser Thr Gln Arg Leu Leu Ala Ala
                85                  90                  95

<210> SEQ ID NO 127
<211> LENGTH: 297
<212> TYPE: DNA
<213> ORGANISM: artificial sequence
<220> FEATURE:
<223> OTHER INFORMATION: Chemically synthesized
<220> FEATURE:
<221> NAME/KEY: CDS
<222> LOCATION: (1)..(297)

<400> SEQUENCE: 127 atg agc cgt cgt ccg cgt cag gac ccg ctg cag cag cgt cag gac ccg      48
Met Ser Arg Arg Pro Arg Gln Asp Pro Leu Gln Gln Arg Gln Asp Pro
1               5                   10                  15
```

```
agc cgt cgt ccg cgt cag gac ccg ctg cag cag cgt cag gga tcc atc      96
Ser Arg Arg Pro Arg Gln Asp Pro Leu Gln Gln Arg Gln Gly Ser Ile
                20                  25                  30 gat cca cgt ttc cac gaa aac tgg ccg tct gcc ggc ggt acc tct act     144
Asp Pro Arg Phe His Glu Asn Trp Pro Ser Ala Gly Gly Thr Ser Thr
            35                  40                  45 tcc aaa gct tcc acc act acg act tct agc aaa acc acc act aca tcc     192
Ser Lys Ala Ser Thr Thr Thr Thr Ser Ser Lys Thr Thr Thr Thr Ser
50                  55                  60 tct aag act acc acg act acc tcc aaa acc tct act acc tct agc tcc     240
Ser Lys Thr Thr Thr Thr Thr Ser Lys Thr Ser Thr Thr Ser Ser Ser
65                  70                  75                  80 tct acg ggc ggc gcc act cac aag acc tct act cag cgt ctg ctg gct     288
Ser Thr Gly Gly Ala Thr His Lys Thr Ser Thr Gln Arg Leu Leu Ala
                85                  90                  95 gca taa tga                                                         297
Ala

<210> SEQ ID NO 128
<211> LENGTH: 97
<212> TYPE: PRT
<213> ORGANISM: artificial sequence
<220> FEATURE:
<223> OTHER INFORMATION: Synthetic Construct

<400> SEQUENCE: 128

Met Ser Arg Arg Pro Arg Gln Asp Pro Leu Gln Gln Arg Gln Asp Pro
1               5                   10                  15

Ser Arg Arg Pro Arg Gln Asp Pro Leu Gln Gln Arg Gln Gly Ser Ile
                20                  25                  30

Asp Pro Arg Phe His Glu Asn Trp Pro Ser Ala Gly Gly Thr Ser Thr
            35                  40                  45

Ser Lys Ala Ser Thr Thr Thr Thr Ser Ser Lys Thr Thr Thr Thr Ser
50                  55                  60

Ser Lys Thr Thr Thr Thr Thr Ser Lys Thr Ser Thr Thr Ser Ser Ser
65                  70                  75                  80

Ser Thr Gly Gly Ala Thr His Lys Thr Ser Thr Gln Arg Leu Leu Ala
                85                  90                  95

Ala

<210> SEQ ID NO 129
<211> LENGTH: 279
<212> TYPE: DNA
<213> ORGANISM: artificial sequence
<220> FEATURE:
<223> OTHER INFORMATION: Chemically synthesized
<220> FEATURE:
<221> NAME/KEY: CDS
<222> LOCATION: (1)..(279)

<400> SEQUENCE: 129 atg agc cgt gaa ccg gaa cag ctg caa cag gaa cag agc gaa gaa ccg      48
Met Ser Arg Glu Pro Glu Gln Leu Gln Gln Glu Gln Ser Glu Glu Pro
1               5                   10                  15 gaa cag ctg caa cag gaa cag gga tcc atc gat cca cgt ttc cac gaa      96
Glu Gln Leu Gln Gln Glu Gln Gly Ser Ile Asp Pro Arg Phe His Glu
                20                  25                  30 aac tgg ccg tct gcc ggc ggt acc tct act tcc aaa gct tcc acc act     144
Asn Trp Pro Ser Ala Gly Gly Thr Ser Thr Ser Lys Ala Ser Thr Thr
            35                  40                  45 acg act tct agc aaa acc acc act aca tcc tct aag act acc acg act     192
```

```
Thr Thr Ser Ser Lys Thr Thr Thr Ser Ser Lys Thr Thr Thr
    50                  55                  60 acc tcc aaa acc tct act acc tct agc tcc tct acg ggc ggc gcc act        240
Thr Ser Lys Thr Ser Thr Thr Ser Ser Ser Thr Gly Gly Ala Thr
65                  70                  75                  80 cac aag acc tct act cag cgt ctg ctg gct gca taa tga                    279
His Lys Thr Ser Thr Gln Arg Leu Leu Ala Ala
                85                  90

<210> SEQ ID NO 130
<211> LENGTH: 91
<212> TYPE: PRT
<213> ORGANISM: artificial sequence
<220> FEATURE:
<223> OTHER INFORMATION: Synthetic Construct

<400> SEQUENCE: 130

Met Ser Arg Glu Pro Glu Gln Leu Gln Gln Glu Gln Ser Glu Glu Pro
1               5                   10                  15

Glu Gln Leu Gln Gln Glu Gln Gly Ser Ile Asp Pro Arg Phe His Glu
            20                  25                  30

Asn Trp Pro Ser Ala Gly Gly Thr Ser Thr Ser Lys Ala Ser Thr Thr
        35                  40                  45

Thr Thr Ser Ser Lys Thr Thr Thr Ser Ser Lys Thr Thr Thr Thr
    50                  55                  60

Thr Ser Lys Thr Ser Thr Thr Ser Ser Ser Thr Gly Gly Ala Thr
65                  70                  75                  80

His Lys Thr Ser Thr Gln Arg Leu Leu Ala Ala
                85                  90

<210> SEQ ID NO 131
<211> LENGTH: 279
<212> TYPE: DNA
<213> ORGANISM: artificial sequence
<220> FEATURE:
<223> OTHER INFORMATION: Chemically synthesized
<220> FEATURE:
<221> NAME/KEY: CDS
<222> LOCATION: (1)..(279)

<400> SEQUENCE: 131 atg agc gaa gaa ccg gaa cag ctg caa cag gaa cag agc gaa gaa ccg        48
Met Ser Glu Glu Pro Glu Gln Leu Gln Gln Glu Gln Ser Glu Glu Pro
1               5                   10                  15 gaa cag ctg caa cag gaa cag gga tcc atc gat cca cgt ttc cac gaa        96
Glu Gln Leu Gln Gln Glu Gln Gly Ser Ile Asp Pro Arg Phe His Glu
            20                  25                  30 aac tgg ccg tct gcc ggc ggt acc tct act tcc aaa gct tcc acc act        144
Asn Trp Pro Ser Ala Gly Gly Thr Ser Thr Ser Lys Ala Ser Thr Thr
        35                  40                  45 acg act tct agc aaa acc acc act aca tcc tct aag act acc acg act        192
Thr Thr Ser Ser Lys Thr Thr Thr Ser Ser Lys Thr Thr Thr Thr
    50                  55                  60 acc tcc aaa acc tct act acc tct agc tcc tct acg ggc ggc gcc act        240
Thr Ser Lys Thr Ser Thr Thr Ser Ser Ser Thr Gly Gly Ala Thr
65                  70                  75                  80 cac aag acc tct act cag cgt ctg ctg gct gca taa tga                    279
His Lys Thr Ser Thr Gln Arg Leu Leu Ala Ala
                85                  90

<210> SEQ ID NO 132
<211> LENGTH: 91
```

```
<212> TYPE: PRT
<213> ORGANISM: artificial sequence
<220> FEATURE:
<223> OTHER INFORMATION: Synthetic Construct

<400> SEQUENCE: 132

Met Ser Glu Glu Pro Glu Gln Leu Gln Gln Glu Gln Ser Glu Glu Pro
1               5                   10                  15

Glu Gln Leu Gln Gln Gln Gln Gly Ser Ile Asp Pro Arg Phe His Glu
                20                  25                  30

Asn Trp Pro Ser Ala Gly Gly Thr Ser Thr Ser Lys Ala Ser Thr Thr
            35                  40                  45

Thr Thr Ser Ser Lys Thr Thr Thr Thr Ser Ser Lys Thr Thr Thr Thr
        50                  55                  60

Thr Ser Lys Thr Ser Thr Thr Ser Ser Ser Thr Gly Gly Ala Thr
65                  70                  75                  80

His Lys Thr Ser Thr Gln Arg Leu Leu Ala Ala
                85                  90

<210> SEQ ID NO 133
<211> LENGTH: 282
<212> TYPE: DNA
<213> ORGANISM: artificial sequence
<220> FEATURE:
<223> OTHER INFORMATION: Chemically synthesized
<220> FEATURE:
<221> NAME/KEY: CDS
<222> LOCATION: (1)..(282)

<400> SEQUENCE: 133 atg agc cgt cgt ccg cgt cag ttg cag cag cgt cag agc cgt cgt ccg      48
Met Ser Arg Arg Pro Arg Gln Leu Gln Gln Arg Gln Ser Arg Arg Pro
1               5                   10                  15 cgt cag ttg cag cag cgt cag gaa gga tcc atc gat cca cgt ttc cac      96
Arg Gln Leu Gln Gln Arg Gln Glu Gly Ser Ile Asp Pro Arg Phe His
                20                  25                  30 gaa aac tgg ccg tct gcc ggc ggt acc tct act tcc aaa gct tcc acc     144
Glu Asn Trp Pro Ser Ala Gly Gly Thr Ser Thr Ser Lys Ala Ser Thr
            35                  40                  45 act acg act tct agc aaa acc acc act aca tcc tct aag act acc acg     192
Thr Thr Thr Ser Ser Lys Thr Thr Thr Thr Ser Ser Lys Thr Thr Thr
        50                  55                  60 act acc tcc aaa acc tct act acc tct agc tcc tct acg ggc ggc gcc     240
Thr Thr Ser Lys Thr Ser Thr Thr Ser Ser Ser Thr Gly Gly Ala
65                  70                  75                  80 act cac aag acc tct act cag cgt ctg ctg gct gca taa tga             282
Thr His Lys Thr Ser Thr Gln Arg Leu Leu Ala Ala
                85                  90

<210> SEQ ID NO 134
<211> LENGTH: 92
<212> TYPE: PRT
<213> ORGANISM: artificial sequence
<220> FEATURE:
<223> OTHER INFORMATION: Synthetic Construct

<400> SEQUENCE: 134

Met Ser Arg Arg Pro Arg Gln Leu Gln Gln Arg Gln Ser Arg Arg Pro
1               5                   10                  15

Arg Gln Leu Gln Gln Arg Gln Glu Gly Ser Ile Asp Pro Arg Phe His
                20                  25                  30

Glu Asn Trp Pro Ser Ala Gly Gly Thr Ser Thr Ser Lys Ala Ser Thr
```

-continued

```
                35                  40                  45
Thr Thr Thr Ser Ser Lys Thr Thr Thr Ser Ser Lys Thr Thr Thr
    50                  55                  60

Thr Thr Ser Lys Thr Ser Thr Thr Ser Ser Ser Thr Gly Gly Ala
65                  70                  75                  80

Thr His Lys Thr Ser Thr Gln Arg Leu Leu Ala Ala
                85                  90

<210> SEQ ID NO 135
<211> LENGTH: 306
<212> TYPE: DNA
<213> ORGANISM: artificial sequence
<220> FEATURE:
<223> OTHER INFORMATION: Chemically synthesized
<220> FEATURE:
<221> NAME/KEY: CDS
<222> LOCATION: (1)..(306)

<400> SEQUENCE: 135 atg agc cgt cgt ccg cgt cag ttg cag cag cgt cag agc cgt cgt ccg      48
Met Ser Arg Arg Pro Arg Gln Leu Gln Gln Arg Gln Ser Arg Arg Pro
1               5                   10                  15 cgt cag ttg cag cag cgt cag gaa gaa gaa gaa gaa gaa gaa gaa           96
Arg Gln Leu Gln Gln Arg Gln Glu Glu Glu Glu Glu Glu Glu Glu
            20                  25                  30 gga tcc atc gat cca cgt ttc cac gaa aac tgg ccg tct gcc ggc ggt      144
Gly Ser Ile Asp Pro Arg Phe His Glu Asn Trp Pro Ser Ala Gly Gly
        35                  40                  45 acc tct act tcc aaa gct tcc acc act acg act tct agc aaa acc acc     192
Thr Ser Thr Ser Lys Ala Ser Thr Thr Thr Thr Ser Ser Lys Thr Thr
50                  55                  60 act aca tcc tct aag act acc acg act acc tcc aaa acc tct act acc    240
Thr Thr Ser Ser Lys Thr Thr Thr Thr Thr Ser Lys Thr Ser Thr Thr
65                  70                  75                  80 tct agc tcc tct acg ggc ggc gcc act cac aag acc tct act cag cgt    288
Ser Ser Ser Ser Thr Gly Gly Ala Thr His Lys Thr Ser Thr Gln Arg
                85                  90                  95 ctg ctg gct gca taa tga                                             306
Leu Leu Ala Ala
            100

<210> SEQ ID NO 136
<211> LENGTH: 100
<212> TYPE: PRT
<213> ORGANISM: artificial sequence
<220> FEATURE:
<223> OTHER INFORMATION: Synthetic Construct

<400> SEQUENCE: 136

Met Ser Arg Arg Pro Arg Gln Leu Gln Gln Arg Gln Ser Arg Arg Pro
1               5                   10                  15

Arg Gln Leu Gln Gln Arg Gln Glu Glu Glu Glu Glu Glu Glu Glu
            20                  25                  30

Gly Ser Ile Asp Pro Arg Phe His Glu Asn Trp Pro Ser Ala Gly Gly
        35                  40                  45

Thr Ser Thr Ser Lys Ala Ser Thr Thr Thr Ser Ser Lys Thr Thr
    50                  55                  60

Thr Thr Ser Ser Lys Thr Thr Thr Thr Ser Lys Thr Ser Thr Thr
65                  70                  75                  80

Ser Ser Ser Ser Thr Gly Gly Ala Thr His Lys Thr Ser Thr Gln Arg
                85                  90                  95
```

Leu Leu Ala Ala
          100

<210> SEQ ID NO 137
<211> LENGTH: 11
<212> TYPE: PRT
<213> ORGANISM: artificial sequence
<220> FEATURE:
<223> OTHER INFORMATION: Core sequence derived from Caenorhabditis
      elegans
<220> FEATURE:
<221> NAME/KEY: MISC_FEATURE
<222> LOCATION: (2)..(2)
<223> OTHER INFORMATION: Xaa = Arg or Glu
<220> FEATURE:
<221> NAME/KEY: MISC_FEATURE
<222> LOCATION: (3)..(3)
<223> OTHER INFORMATION: Xaa = Arg or Glu
<220> FEATURE:
<221> NAME/KEY: MISC_FEATURE
<222> LOCATION: (4)..(4)
<223> OTHER INFORMATION: Xaa = Pro or Gln
<220> FEATURE:
<221> NAME/KEY: MISC_FEATURE
<222> LOCATION: (5)..(5)
<223> OTHER INFORMATION: Xaa = Arg, Gln, or Asp
<220> FEATURE:
<221> NAME/KEY: MISC_FEATURE
<222> LOCATION: (6)..(6)
<223> OTHER INFORMATION: Xaa = Gln or Pro
<220> FEATURE:
<221> NAME/KEY: MISC_FEATURE
<222> LOCATION: (10)..(10)
<223> OTHER INFORMATION: Xaa = Arg or Glu

<400> SEQUENCE: 137

Ser Xaa Xaa Xaa Xaa Xaa Leu Gln Gln Xaa Gln
1               5                   10

<210> SEQ ID NO 138
<211> LENGTH: 573
<212> TYPE: DNA
<213> ORGANISM: Caenorhabditis elegans
<220> FEATURE:
<221> NAME/KEY: CDS
<222> LOCATION: (1)..(573)

<400> SEQUENCE: 138

```
atg aag cgc gac cag agg ttg gca att cga atc aac tca gaa caa ctg      48
Met Lys Arg Asp Gln Arg Leu Ala Ile Arg Ile Asn Ser Glu Gln Leu
1               5                   10                  15 cag cat cta gga agg att ttg agc aga cgt cca cgt cag ctc cag caa      96
Gln His Leu Gly Arg Ile Leu Ser Arg Arg Pro Arg Gln Leu Gln Gln
            20                  25                  30 cgt caa cat cat caa cag cag gaa tca ttg gag gag ttg ctg ctt tgg    144
Arg Gln His His Gln Gln Gln Glu Ser Leu Glu Glu Leu Leu Leu Trp
        35                  40                  45 tgg tgg tat gtg ctc ttg cag tgc tct tct tct tct gct gga gaa atc    192
Trp Trp Tyr Val Leu Leu Gln Cys Ser Ser Ser Ser Ala Gly Glu Ile
50                  55                  60 cat cca tct gaa aag agt gaa aag ggc ggg gca aca tct gca cct cca    240
His Pro Ser Glu Lys Ser Glu Lys Gly Gly Ala Thr Ser Ala Pro Pro
65                  70                  75                  80 aag aac aca gaa atg agg gag aag ctt ctg gag act caa gcc aac ctt    288
Lys Asn Thr Glu Met Arg Glu Lys Leu Leu Glu Thr Gln Ala Asn Leu
                85                  90                  95 cag aag atc cgg gcc cac atg aag aag aac gct cta cgg cac aaa tcg    336
Gln Lys Ile Arg Ala His Met Lys Lys Asn Ala Leu Arg His Lys Ser
```

```
                       100                 105                 110
gac act aga aca tcg aag ttc aaa aag atg gga gca atc ttc att ctc      384
Asp Thr Arg Thr Ser Lys Phe Lys Lys Met Gly Ala Ile Phe Ile Leu
        115                 120                 125 atg gag cct gat att ctc acg ccg ccg gta ctt ccc aac gtt gcc ctc      432
Met Glu Pro Asp Ile Leu Thr Pro Pro Val Leu Pro Asn Val Ala Leu
130                 135                 140 gac aaa gtg ttt tat gat ccg aca tac aac gag atg tac gat att gga      480
Asp Lys Val Phe Tyr Asp Pro Thr Tyr Asn Glu Met Tyr Asp Ile Gly
145                 150                 155                 160 acc gat gtt gat gac atc gag ctg gat gcg tcc ttt atg gtg gat cca      528
Thr Asp Val Asp Asp Ile Glu Leu Asp Ala Ser Phe Met Val Asp Pro
                165                 170                 175 agc aca atc acg gag gac gag gca acg aag aac aca cca tcg taa          573
Ser Thr Ile Thr Glu Asp Glu Ala Thr Lys Asn Thr Pro Ser
                180                 185                 190
```

<210> SEQ ID NO 139
<211> LENGTH: 190
<212> TYPE: PRT
<213> ORGANISM: Caenorhabditis elegans

<400> SEQUENCE: 139

```
Met Lys Arg Asp Gln Arg Leu Ala Ile Arg Ile Asn Ser Glu Gln Leu
1               5                   10                  15

Gln His Leu Gly Arg Ile Leu Ser Arg Arg Pro Arg Gln Leu Gln Gln
            20                  25                  30

Arg Gln His Gln Gln Gln Glu Ser Leu Glu Glu Leu Leu Leu Trp
        35                  40                  45

Trp Trp Tyr Val Leu Leu Gln Cys Ser Ser Ser Ala Gly Glu Ile
50                  55                  60

His Pro Ser Glu Lys Ser Glu Lys Gly Gly Ala Thr Ser Ala Pro Pro
65                  70                  75                  80

Lys Asn Thr Glu Met Arg Glu Lys Leu Leu Glu Thr Gln Ala Asn Leu
                85                  90                  95

Gln Lys Ile Arg Ala His Met Lys Lys Asn Ala Leu Arg His Lys Ser
            100                 105                 110

Asp Thr Arg Thr Ser Lys Phe Lys Lys Met Gly Ala Ile Phe Ile Leu
        115                 120                 125

Met Glu Pro Asp Ile Leu Thr Pro Pro Val Leu Pro Asn Val Ala Leu
130                 135                 140

Asp Lys Val Phe Tyr Asp Pro Thr Tyr Asn Glu Met Tyr Asp Ile Gly
145                 150                 155                 160

Thr Asp Val Asp Asp Ile Glu Leu Asp Ala Ser Phe Met Val Asp Pro
                165                 170                 175

Ser Thr Ile Thr Glu Asp Glu Ala Thr Lys Asn Thr Pro Ser
            180                 185                 190
```

<210> SEQ ID NO 140
<211> LENGTH: 7
<212> TYPE: PRT
<213> ORGANISM: artificial sequence
<220> FEATURE:
<223> OTHER INFORMATION: Skin binding peptide

<400> SEQUENCE: 140

```
Phe Thr Gln Ser Leu Pro Arg
1               5
```

```
<210> SEQ ID NO 141
<211> LENGTH: 12
<212> TYPE: PRT
<213> ORGANISM: artificial sequence
<220> FEATURE:
<223> OTHER INFORMATION: Skin binding peptide

<400> SEQUENCE: 141

Thr Pro Phe His Ser Pro Glu Asn Ala Pro Gly Ser
1               5                   10

<210> SEQ ID NO 142
<211> LENGTH: 12
<212> TYPE: PRT
<213> ORGANISM: artificial sequence
<220> FEATURE:
<223> OTHER INFORMATION: Skin binding peptide

<400> SEQUENCE: 142

Lys Gln Ala Thr Phe Pro Pro Asn Pro Thr Ala Tyr
1               5                   10

<210> SEQ ID NO 143
<211> LENGTH: 12
<212> TYPE: PRT
<213> ORGANISM: artificial sequence
<220> FEATURE:
<223> OTHER INFORMATION: Skin binding peptide

<400> SEQUENCE: 143

His Gly His Met Val Ser Thr Ser Gln Leu Ser Ile
1               5                   10

<210> SEQ ID NO 144
<211> LENGTH: 7
<212> TYPE: PRT
<213> ORGANISM: artificial sequence
<220> FEATURE:
<223> OTHER INFORMATION: Skin binding peptide

<400> SEQUENCE: 144

Leu Ser Pro Ser Arg Met Lys
1               5

<210> SEQ ID NO 145
<211> LENGTH: 7
<212> TYPE: PRT
<213> ORGANISM: artificial sequence
<220> FEATURE:
<223> OTHER INFORMATION: Skin binding peptide

<400> SEQUENCE: 145

Leu Pro Ile Pro Arg Met Lys
1               5

<210> SEQ ID NO 146
<211> LENGTH: 7
<212> TYPE: PRT
<213> ORGANISM: artificial sequence
<220> FEATURE:
<223> OTHER INFORMATION: Skin binding peptide

<400> SEQUENCE: 146

His Gln Arg Pro Tyr Leu Thr
1               5
```

```
<210> SEQ ID NO 147
<211> LENGTH: 7
<212> TYPE: PRT
<213> ORGANISM: artificial sequence
<220> FEATURE:
<223> OTHER INFORMATION: Skin binding peptide

<400> SEQUENCE: 147

Phe Pro Pro Leu Leu Arg Leu
1               5

<210> SEQ ID NO 148
<211> LENGTH: 12
<212> TYPE: PRT
<213> ORGANISM: artificial sequence
<220> FEATURE:
<223> OTHER INFORMATION: Hair binding peptide

<400> SEQUENCE: 148

Ser Val Ser Val Gly Met Lys Pro Ser Pro Arg Pro
1               5                   10

<210> SEQ ID NO 149
<211> LENGTH: 12
<212> TYPE: PRT
<213> ORGANISM: artificial sequence
<220> FEATURE:
<223> OTHER INFORMATION: Hair binding peptide

<400> SEQUENCE: 149

Leu Asp Val Glu Ser Tyr Lys Gly Thr Ser Met Pro
1               5                   10

<210> SEQ ID NO 150
<211> LENGTH: 12
<212> TYPE: PRT
<213> ORGANISM: artificial sequence
<220> FEATURE:
<223> OTHER INFORMATION: Hair binding peptide

<400> SEQUENCE: 150

Arg Val Pro Asn Lys Thr Val Thr Val Asp Gly Ala
1               5                   10

<210> SEQ ID NO 151
<211> LENGTH: 12
<212> TYPE: PRT
<213> ORGANISM: artificial sequence
<220> FEATURE:
<223> OTHER INFORMATION: Hair binding peptide

<400> SEQUENCE: 151

Asp Arg His Lys Ser Lys Tyr Ser Ser Thr Lys Ser
1               5                   10

<210> SEQ ID NO 152
<211> LENGTH: 12
<212> TYPE: PRT
<213> ORGANISM: artificial sequence
<220> FEATURE:
<223> OTHER INFORMATION: Hair binding peptide

<400> SEQUENCE: 152

Lys Asn Phe Pro Gln Gln Lys Glu Phe Pro Leu Ser
1               5                   10

<210> SEQ ID NO 153
```

```
<211> LENGTH: 12
<212> TYPE: PRT
<213> ORGANISM: artificial sequence
<220> FEATURE:
<223> OTHER INFORMATION: Hair binding peptide

<400> SEQUENCE: 153

Gln Arg Asn Ser Pro Pro Ala Met Ser Arg Arg Asp
1               5                   10

<210> SEQ ID NO 154
<211> LENGTH: 12
<212> TYPE: PRT
<213> ORGANISM: artificial sequence
<220> FEATURE:
<223> OTHER INFORMATION: Hair binding peptide

<400> SEQUENCE: 154

Thr Arg Lys Pro Asn Met Pro His Gly Gln Tyr Leu
1               5                   10

<210> SEQ ID NO 155
<211> LENGTH: 12
<212> TYPE: PRT
<213> ORGANISM: artificial sequence
<220> FEATURE:
<223> OTHER INFORMATION: Hair binding peptide

<400> SEQUENCE: 155

Lys Pro Pro His Leu Ala Lys Leu Pro Phe Thr Thr
1               5                   10

<210> SEQ ID NO 156
<211> LENGTH: 12
<212> TYPE: PRT
<213> ORGANISM: artificial sequence
<220> FEATURE:
<223> OTHER INFORMATION: Hair binding peptide

<400> SEQUENCE: 156

Asn Lys Arg Pro Pro Thr Ser His Arg Ile His Ala
1               5                   10

<210> SEQ ID NO 157
<211> LENGTH: 12
<212> TYPE: PRT
<213> ORGANISM: artificial sequence
<220> FEATURE:
<223> OTHER INFORMATION: Hair binding peptide

<400> SEQUENCE: 157

Asn Leu Pro Arg Tyr Gln Pro Pro Cys Lys Pro Leu
1               5                   10

<210> SEQ ID NO 158
<211> LENGTH: 12
<212> TYPE: PRT
<213> ORGANISM: artificial sequence
<220> FEATURE:
<223> OTHER INFORMATION: Hair binding peptide

<400> SEQUENCE: 158

Arg Pro Pro Trp Lys Lys Pro Ile Pro Pro Ser Glu
1               5                   10

<210> SEQ ID NO 159
<211> LENGTH: 12
```

<212> TYPE: PRT
<213> ORGANISM: artificial sequence
<220> FEATURE:
<223> OTHER INFORMATION: Hair binding peptide

<400> SEQUENCE: 159

Arg Gln Arg Pro Lys Asp His Phe Phe Ser Arg Pro
1               5                   10

<210> SEQ ID NO 160
<211> LENGTH: 12
<212> TYPE: PRT
<213> ORGANISM: artificial sequence
<220> FEATURE:
<223> OTHER INFORMATION: Hair binding peptide
<220> FEATURE:
<221> NAME/KEY: MISC_FEATURE
<222> LOCATION: (6)..(6)
<223> OTHER INFORMATION: Xaa = Thr or Pro
<220> FEATURE:
<221> NAME/KEY: MISC_FEATURE
<222> LOCATION: (12)..(12)
<223> OTHER INFORMATION: Xaa = Glu or Ala

<400> SEQUENCE: 160

Ser Val Pro Asn Lys Xaa Val Thr Val Asp Gly Xaa
1               5                   10

<210> SEQ ID NO 161
<211> LENGTH: 12
<212> TYPE: PRT
<213> ORGANISM: artificial sequence
<220> FEATURE:
<223> OTHER INFORMATION: Hair binding peptide

<400> SEQUENCE: 161

Thr Thr Lys Trp Arg His Arg Ala Pro Val Ser Pro
1               5                   10

<210> SEQ ID NO 162
<211> LENGTH: 12
<212> TYPE: PRT
<213> ORGANISM: artificial sequence
<220> FEATURE:
<223> OTHER INFORMATION: Hair binding peptide

<400> SEQUENCE: 162

Trp Leu Gly Lys Asn Arg Ile Lys Pro Arg Ala Ser
1               5                   10

<210> SEQ ID NO 163
<211> LENGTH: 12
<212> TYPE: PRT
<213> ORGANISM: artificial sequence
<220> FEATURE:
<223> OTHER INFORMATION: Hair binding peptide

<400> SEQUENCE: 163

Ser Asn Phe Lys Thr Pro Leu Pro Leu Thr Gln Ser
1               5                   10

<210> SEQ ID NO 164
<211> LENGTH: 12
<212> TYPE: PRT
<213> ORGANISM: artificial sequence
<220> FEATURE:
<223> OTHER INFORMATION: Hair binding peptide

<400> SEQUENCE: 164

```
Lys Glu Leu Gln Thr Arg Asn Val Val Gln Arg Glu
1               5                   10
```

<210> SEQ ID NO 165
<211> LENGTH: 12
<212> TYPE: PRT
<213> ORGANISM: artificial sequence
<220> FEATURE:
<223> OTHER INFORMATION: Hair binding peptide

<400> SEQUENCE: 165

```
Gly Met Pro Ala Met His Trp Ile His Pro Phe Ala
1               5                   10
```

<210> SEQ ID NO 166
<211> LENGTH: 12
<212> TYPE: PRT
<213> ORGANISM: artificial sequence
<220> FEATURE:
<223> OTHER INFORMATION: Hair binding peptide

<400> SEQUENCE: 166

```
Thr Pro Thr Ala Asn Gln Phe Thr Gln Ser Val Pro
1               5                   10
```

<210> SEQ ID NO 167
<211> LENGTH: 12
<212> TYPE: PRT
<213> ORGANISM: artificial sequence
<220> FEATURE:
<223> OTHER INFORMATION: Hair binding peptide

<400> SEQUENCE: 167

```
Ala Ala Gly Leu Ser Gln Lys His Glu Arg Asn Arg
1               5                   10
```

<210> SEQ ID NO 168
<211> LENGTH: 12
<212> TYPE: PRT
<213> ORGANISM: artificial sequence
<220> FEATURE:
<223> OTHER INFORMATION: Hair binding peptide

<400> SEQUENCE: 168

```
Glu Thr Val His Gln Thr Pro Leu Ser Asp Arg Pro
1               5                   10
```

<210> SEQ ID NO 169
<211> LENGTH: 12
<212> TYPE: PRT
<213> ORGANISM: artificial sequence
<220> FEATURE:
<223> OTHER INFORMATION: Hair binding peptide

<400> SEQUENCE: 169

```
Leu Pro Ala Leu His Ile Gln Arg His Pro Arg Met
1               5                   10
```

<210> SEQ ID NO 170
<211> LENGTH: 12
<212> TYPE: PRT
<213> ORGANISM: artificial sequence
<220> FEATURE:
<223> OTHER INFORMATION: Hair binding peptide

<400> SEQUENCE: 170

```
Gln Pro Ser His Ser Gln Ser His Asn Leu Arg Ser
1               5                   10
```

```
<210> SEQ ID NO 171
<211> LENGTH: 12
<212> TYPE: PRT
<213> ORGANISM: artificial sequence
<220> FEATURE:
<223> OTHER INFORMATION: Hair binding peptide

<400> SEQUENCE: 171

Arg Gly Ser Gln Lys Ser Lys Pro Pro Arg Pro Pro
1               5                   10
```

```
<210> SEQ ID NO 172
<211> LENGTH: 12
<212> TYPE: PRT
<213> ORGANISM: artificial sequence
<220> FEATURE:
<223> OTHER INFORMATION: Hair binding peptide

<400> SEQUENCE: 172

Thr His Thr Gln Lys Thr Pro Leu Leu Tyr Tyr His
1               5                   10
```

```
<210> SEQ ID NO 173
<211> LENGTH: 12
<212> TYPE: PRT
<213> ORGANISM: artificial sequence
<220> FEATURE:
<223> OTHER INFORMATION: Hair binding peptide

<400> SEQUENCE: 173

Thr Lys Gly Ser Ser Gln Ala Ile Leu Lys Ser Thr
1               5                   10
```

```
<210> SEQ ID NO 174
<211> LENGTH: 7
<212> TYPE: PRT
<213> ORGANISM: artificial sequence
<220> FEATURE:
<223> OTHER INFORMATION: Hair binding peptide

<400> SEQUENCE: 174

Asp Leu His Thr Val Tyr His
1               5
```

```
<210> SEQ ID NO 175
<211> LENGTH: 7
<212> TYPE: PRT
<213> ORGANISM: artificial sequence
<220> FEATURE:
<223> OTHER INFORMATION: Hair binding peptide

<400> SEQUENCE: 175

His Ile Lys Pro Pro Thr Arg
1               5
```

```
<210> SEQ ID NO 176
<211> LENGTH: 7
<212> TYPE: PRT
<213> ORGANISM: artificial sequence
<220> FEATURE:
<223> OTHER INFORMATION: Hair binding peptide

<400> SEQUENCE: 176

His Pro Val Trp Pro Ala Ile
```

<210> SEQ ID NO 177
<211> LENGTH: 7
<212> TYPE: PRT
<213> ORGANISM: artificial sequence
<220> FEATURE:
<223> OTHER INFORMATION: Hair binding peptide

<400> SEQUENCE: 177

Met Pro Leu Tyr Tyr Leu Gln
1               5

<210> SEQ ID NO 178
<211> LENGTH: 26
<212> TYPE: PRT
<213> ORGANISM: artificial sequence
<220> FEATURE:
<223> OTHER INFORMATION: Hair binding peptide

<400> SEQUENCE: 178

His Leu Thr Val Pro Trp Arg Gly Gly Gly Ser Ala Val Pro Phe Tyr
1               5                   10                  15

Ser His Ser Gln Ile Thr Leu Pro Asn His
            20                  25

<210> SEQ ID NO 179
<211> LENGTH: 41
<212> TYPE: PRT
<213> ORGANISM: artificial sequence
<220> FEATURE:
<223> OTHER INFORMATION: Hair binding peptide

<400> SEQUENCE: 179

Gly Pro His Asp Thr Ser Ser Gly Gly Val Arg Pro Asn Leu His His
1               5                   10                  15

Thr Ser Lys Lys Glu Lys Arg Glu Asn Arg Lys Val Pro Phe Tyr Ser
            20                  25                  30

His Ser Val Thr Ser Arg Gly Asn Val
        35                  40

<210> SEQ ID NO 180
<211> LENGTH: 7
<212> TYPE: PRT
<213> ORGANISM: artificial sequence
<220> FEATURE:
<223> OTHER INFORMATION: Hair binding peptide

<400> SEQUENCE: 180

Lys His Pro Thr Tyr Arg Gln
1               5

<210> SEQ ID NO 181
<211> LENGTH: 7
<212> TYPE: PRT
<213> ORGANISM: artificial sequence
<220> FEATURE:
<223> OTHER INFORMATION: Hair binding peptide

<400> SEQUENCE: 181

His Pro Met Ser Ala Pro Arg
1               5

<210> SEQ ID NO 182
<211> LENGTH: 7

```
<212> TYPE: PRT
<213> ORGANISM: artificial sequence
<220> FEATURE:
<223> OTHER INFORMATION: Hair binding peptide

<400> SEQUENCE: 182

Met Pro Lys Tyr Tyr Leu Gln
1               5

<210> SEQ ID NO 183
<211> LENGTH: 7
<212> TYPE: PRT
<213> ORGANISM: artificial sequence
<220> FEATURE:
<223> OTHER INFORMATION: Hair binding peptide

<400> SEQUENCE: 183

Met His Ala His Ser Ile Ala
1               5

<210> SEQ ID NO 184
<211> LENGTH: 7
<212> TYPE: PRT
<213> ORGANISM: artificial sequence
<220> FEATURE:
<223> OTHER INFORMATION: Hair binding peptide

<400> SEQUENCE: 184

Thr Ala Ala Thr Thr Ser Pro
1               5

<210> SEQ ID NO 185
<211> LENGTH: 7
<212> TYPE: PRT
<213> ORGANISM: artificial sequence
<220> FEATURE:
<223> OTHER INFORMATION: Hair binding peptide

<400> SEQUENCE: 185

Leu Gly Ile Pro Gln Asn Leu
1               5

<210> SEQ ID NO 186
<211> LENGTH: 12
<212> TYPE: PRT
<213> ORGANISM: artificial sequence
<220> FEATURE:
<223> OTHER INFORMATION: Hair binding peptide

<400> SEQUENCE: 186

Ala Lys Pro Ile Ser Gln His Leu Gln Arg Gly Ser
1               5                   10

<210> SEQ ID NO 187
<211> LENGTH: 12
<212> TYPE: PRT
<213> ORGANISM: artificial sequence
<220> FEATURE:
<223> OTHER INFORMATION: Hair binding peptide

<400> SEQUENCE: 187

Ala Pro Pro Thr Pro Ala Ala Ala Ser Ala Thr Thr
1               5                   10

<210> SEQ ID NO 188
<211> LENGTH: 12
<212> TYPE: PRT
```

```
<213> ORGANISM: artificial sequence
<220> FEATURE:
<223> OTHER INFORMATION: Hair binding peptide

<400> SEQUENCE: 188

Asp Pro Thr Glu Gly Ala Arg Arg Thr Ile Met Thr
1               5                   10

<210> SEQ ID NO 189
<211> LENGTH: 12
<212> TYPE: PRT
<213> ORGANISM: artificial sequence
<220> FEATURE:
<223> OTHER INFORMATION: Hair binding peptide

<400> SEQUENCE: 189

Glu Gln Ile Ser Gly Ser Leu Val Ala Ala Pro Trp
1               5                   10

<210> SEQ ID NO 190
<211> LENGTH: 12
<212> TYPE: PRT
<213> ORGANISM: artificial sequence
<220> FEATURE:
<223> OTHER INFORMATION: Hair binding peptide

<400> SEQUENCE: 190

Leu Asp Thr Ser Phe Pro Pro Val Pro Phe His Ala
1               5                   10

<210> SEQ ID NO 191
<211> LENGTH: 11
<212> TYPE: PRT
<213> ORGANISM: artificial sequence
<220> FEATURE:
<223> OTHER INFORMATION: Hair binding peptide

<400> SEQUENCE: 191

Leu Pro Arg Ile Ala Asn Thr Trp Ser Pro Ser
1               5                   10

<210> SEQ ID NO 192
<211> LENGTH: 12
<212> TYPE: PRT
<213> ORGANISM: artificial sequence
<220> FEATURE:
<223> OTHER INFORMATION: Hair binding peptide

<400> SEQUENCE: 192

Arg Thr Asn Ala Ala Asp His Pro Ala Ala Val Thr
1               5                   10

<210> SEQ ID NO 193
<211> LENGTH: 12
<212> TYPE: PRT
<213> ORGANISM: artificial sequence
<220> FEATURE:
<223> OTHER INFORMATION: Hair binding peptide

<400> SEQUENCE: 193

Ser Leu Asn Trp Val Thr Ile Pro Gly Pro Lys Ile
1               5                   10

<210> SEQ ID NO 194
<211> LENGTH: 12
<212> TYPE: PRT
<213> ORGANISM: artificial sequence
```

```
<220> FEATURE:
<223> OTHER INFORMATION: Hair binding peptide

<400> SEQUENCE: 194

Thr Asp Met Gln Ala Pro Thr Lys Ser Tyr Ser Asn
 1               5                  10

<210> SEQ ID NO 195
<211> LENGTH: 12
<212> TYPE: PRT
<213> ORGANISM: artificial sequence
<220> FEATURE:
<223> OTHER INFORMATION: Hair binding peptide

<400> SEQUENCE: 195

Thr Ile Met Thr Lys Ser Pro Ser Leu Ser Cys Gly
 1               5                  10

<210> SEQ ID NO 196
<211> LENGTH: 12
<212> TYPE: PRT
<213> ORGANISM: artificial sequence
<220> FEATURE:
<223> OTHER INFORMATION: Hair binding peptide

<400> SEQUENCE: 196

Thr Pro Ala Leu Asp Gly Leu Arg Gln Pro Leu Arg
 1               5                  10

<210> SEQ ID NO 197
<211> LENGTH: 12
<212> TYPE: PRT
<213> ORGANISM: artificial sequence
<220> FEATURE:
<223> OTHER INFORMATION: Hair binding peptide

<400> SEQUENCE: 197

Thr Tyr Pro Ala Ser Arg Leu Pro Leu Leu Ala Pro
 1               5                  10

<210> SEQ ID NO 198
<211> LENGTH: 12
<212> TYPE: PRT
<213> ORGANISM: artificial sequence
<220> FEATURE:
<223> OTHER INFORMATION: Hair binding peptide

<400> SEQUENCE: 198

Ala Lys Thr His Lys His Pro Ala Pro Ser Tyr Ser
 1               5                  10

<210> SEQ ID NO 199
<211> LENGTH: 12
<212> TYPE: PRT
<213> ORGANISM: artificial sequence
<220> FEATURE:
<223> OTHER INFORMATION: Hair binding peptide

<400> SEQUENCE: 199

Thr Asp Pro Thr Pro Phe Ser Ile Ser Pro Glu Arg
 1               5                  10

<210> SEQ ID NO 200
<211> LENGTH: 20
<212> TYPE: PRT
<213> ORGANISM: artificial sequence
<220> FEATURE:
```

<223> OTHER INFORMATION: Hair binding peptide

<400> SEQUENCE: 200

Cys Ala Ala Gly Cys Cys Thr Cys Ala Gly Cys Gly Ala Cys Cys Gly
1               5                   10                  15

Ala Ala Thr Ala
            20

<210> SEQ ID NO 201
<211> LENGTH: 12
<212> TYPE: PRT
<213> ORGANISM: artificial sequence
<220> FEATURE:
<223> OTHER INFORMATION: Hair binding peptide

<400> SEQUENCE: 201

Trp His Asp Lys Pro Gln Asn Ser Ser Lys Ser Thr
1               5                   10

<210> SEQ ID NO 202
<211> LENGTH: 12
<212> TYPE: PRT
<213> ORGANISM: artificial sequence
<220> FEATURE:
<223> OTHER INFORMATION: Hair binding peptide

<400> SEQUENCE: 202

Asn Glu Val Pro Ala Arg Asn Ala Pro Trp Leu Val
1               5                   10

<210> SEQ ID NO 203
<211> LENGTH: 13
<212> TYPE: PRT
<213> ORGANISM: artificial sequence
<220> FEATURE:
<223> OTHER INFORMATION: Hair binding peptide

<400> SEQUENCE: 203

Asn Ser Pro Gly Tyr Gln Ala Asp Ser Val Ala Ile Gly
1               5                   10

<210> SEQ ID NO 204
<211> LENGTH: 12
<212> TYPE: PRT
<213> ORGANISM: artificial sequence
<220> FEATURE:
<223> OTHER INFORMATION: Hair binding peptide

<400> SEQUENCE: 204

Thr Gln Asp Ser Ala Gln Lys Ser Pro Ser Pro Leu
1               5                   10

<210> SEQ ID NO 205
<211> LENGTH: 12
<212> TYPE: PRT
<213> ORGANISM: artificial sequence
<220> FEATURE:
<223> OTHER INFORMATION: Hair binding peptide

<400> SEQUENCE: 205

Thr Pro Pro Glu Leu Leu His Gly Asp Pro Arg Ser
1               5                   10

<210> SEQ ID NO 206
<211> LENGTH: 12
<212> TYPE: PRT

<213> ORGANISM: artificial sequence
<220> FEATURE:
<223> OTHER INFORMATION: Hair binding peptide

<400> SEQUENCE: 206

Thr Pro Pro Thr Asn Val Leu Met Leu Ala Thr Lys
1               5                   10

<210> SEQ ID NO 207
<211> LENGTH: 7
<212> TYPE: PRT
<213> ORGANISM: artificial sequence
<220> FEATURE:
<223> OTHER INFORMATION: Hair binding peptide

<400> SEQUENCE: 207

Asn Thr Ser Gln Leu Ser Thr
1               5

<210> SEQ ID NO 208
<211> LENGTH: 7
<212> TYPE: PRT
<213> ORGANISM: artificial sequence
<220> FEATURE:
<223> OTHER INFORMATION: Hair binding peptide

<400> SEQUENCE: 208

Asn Thr Pro Lys Glu Asn Trp
1               5

<210> SEQ ID NO 209
<211> LENGTH: 7
<212> TYPE: PRT
<213> ORGANISM: artificial sequence
<220> FEATURE:
<223> OTHER INFORMATION: Hair binding peptide

<400> SEQUENCE: 209

Asn Thr Pro Ala Ser Asn Arg
1               5

<210> SEQ ID NO 210
<211> LENGTH: 7
<212> TYPE: PRT
<213> ORGANISM: artificial sequence
<220> FEATURE:
<223> OTHER INFORMATION: Hair binding peptide

<400> SEQUENCE: 210

Pro Arg Gly Met Leu Ser Thr
1               5

<210> SEQ ID NO 211
<211> LENGTH: 7
<212> TYPE: PRT
<213> ORGANISM: artificial sequence
<220> FEATURE:
<223> OTHER INFORMATION: Hair binding peptide

<400> SEQUENCE: 211

Pro Pro Thr Tyr Leu Ser Thr
1               5

<210> SEQ ID NO 212
<211> LENGTH: 12
<212> TYPE: PRT
<213> ORGANISM: artificial sequence

```
<220> FEATURE:
<223> OTHER INFORMATION: Hair binding peptide

<400> SEQUENCE: 212

Thr Ile Pro Thr His Arg Gln His Asp Tyr Arg Ser
1               5                   10

<210> SEQ ID NO 213
<211> LENGTH: 7
<212> TYPE: PRT
<213> ORGANISM: artificial sequence
<220> FEATURE:
<223> OTHER INFORMATION: Hair binding peptide

<400> SEQUENCE: 213

Thr Pro Pro Thr His Arg Leu
1               5

<210> SEQ ID NO 214
<211> LENGTH: 7
<212> TYPE: PRT
<213> ORGANISM: artificial sequence
<220> FEATURE:
<223> OTHER INFORMATION: Hair binding peptide

<400> SEQUENCE: 214

Leu Pro Thr Met Ser Thr Pro
1               5

<210> SEQ ID NO 215
<211> LENGTH: 7
<212> TYPE: PRT
<213> ORGANISM: artificial sequence
<220> FEATURE:
<223> OTHER INFORMATION: Hair binding peptide

<400> SEQUENCE: 215

Leu Gly Thr Asn Ser Thr Pro
1               5

<210> SEQ ID NO 216
<211> LENGTH: 12
<212> TYPE: PRT
<213> ORGANISM: artificial sequence
<220> FEATURE:
<223> OTHER INFORMATION: Hair binding peptide

<400> SEQUENCE: 216

Thr Pro Leu Thr Gly Ser Thr Asn Leu Leu Ser Ser
1               5                   10

<210> SEQ ID NO 217
<211> LENGTH: 7
<212> TYPE: PRT
<213> ORGANISM: artificial sequence
<220> FEATURE:
<223> OTHER INFORMATION: Hair binding peptide

<400> SEQUENCE: 217

Thr Pro Leu Thr Lys Glu Thr
1               5

<210> SEQ ID NO 218
<211> LENGTH: 7
<212> TYPE: PRT
<213> ORGANISM: artificial sequence
<220> FEATURE:
```

```
<223> OTHER INFORMATION: Hair binding peptide

<400> SEQUENCE: 218

Gln Gln Ser His Asn Pro Pro
1               5

<210> SEQ ID NO 219
<211> LENGTH: 7
<212> TYPE: PRT
<213> ORGANISM: artificial sequence
<220> FEATURE:
<223> OTHER INFORMATION: Hair binding peptide

<400> SEQUENCE: 219

Thr Gln Pro His Asn Pro Pro
1               5

<210> SEQ ID NO 220
<211> LENGTH: 12
<212> TYPE: PRT
<213> ORGANISM: artificial sequence
<220> FEATURE:
<223> OTHER INFORMATION: Hair binding peptide

<400> SEQUENCE: 220

Ser Thr Asn Leu Leu Arg Thr Ser Thr Val His Pro
1               5                   10

<210> SEQ ID NO 221
<211> LENGTH: 12
<212> TYPE: PRT
<213> ORGANISM: artificial sequence
<220> FEATURE:
<223> OTHER INFORMATION: Hair binding peptide

<400> SEQUENCE: 221

His Thr Gln Pro Ser Tyr Ser Ser Thr Asn Leu Phe
1               5                   10

<210> SEQ ID NO 222
<211> LENGTH: 7
<212> TYPE: PRT
<213> ORGANISM: artificial sequence
<220> FEATURE:
<223> OTHER INFORMATION: Hair binding peptide

<400> SEQUENCE: 222

Ser Leu Leu Ser Ser His Ala
1               5

<210> SEQ ID NO 223
<211> LENGTH: 12
<212> TYPE: PRT
<213> ORGANISM: artificial sequence
<220> FEATURE:
<223> OTHER INFORMATION: Hair binding peptide

<400> SEQUENCE: 223

Gln Gln Ser Ser Ile Ser Leu Ser Ser His Ala Val
1               5                   10

<210> SEQ ID NO 224
<211> LENGTH: 7
<212> TYPE: PRT
<213> ORGANISM: artificial sequence
<220> FEATURE:
<223> OTHER INFORMATION: Hair binding peptide
```

```
<400> SEQUENCE: 224

Asn Ala Ser Pro Ser Ser Leu
1               5

<210> SEQ ID NO 225
<211> LENGTH: 7
<212> TYPE: PRT
<213> ORGANISM: artificial sequence
<220> FEATURE:
<223> OTHER INFORMATION: Hair binding peptide

<400> SEQUENCE: 225

His Ser Pro Ser Ser Leu Arg
1               5

<210> SEQ ID NO 226
<211> LENGTH: 7
<212> TYPE: PRT
<213> ORGANISM: artificial sequence
<220> FEATURE:
<223> OTHER INFORMATION: Hair binding peptide
<220> FEATURE:
<221> NAME/KEY: MISC_FEATURE
<222> LOCATION: (2)..(2)
<223> OTHER INFORMATION: Xaa = His, Arg, or Asn

<400> SEQUENCE: 226

Lys Xaa Ser His His Thr His
1               5

<210> SEQ ID NO 227
<211> LENGTH: 7
<212> TYPE: PRT
<213> ORGANISM: artificial sequence
<220> FEATURE:
<223> OTHER INFORMATION: Hair binding peptide
<220> FEATURE:
<221> NAME/KEY: MISC_FEATURE
<222> LOCATION: (2)..(2)
<223> OTHER INFORMATION: Xaa = His, Arg, or Asn

<400> SEQUENCE: 227

Glu Xaa Ser His His Thr His
1               5

<210> SEQ ID NO 228
<211> LENGTH: 7
<212> TYPE: PRT
<213> ORGANISM: artificial sequence
<220> FEATURE:
<223> OTHER INFORMATION: Hair binding peptide

<400> SEQUENCE: 228

Leu Glu Ser Thr Ser Leu Leu
1               5

<210> SEQ ID NO 229
<211> LENGTH: 7
<212> TYPE: PRT
<213> ORGANISM: artificial sequence
<220> FEATURE:
<223> OTHER INFORMATION: Hair binding peptide

<400> SEQUENCE: 229

Thr Pro Leu Thr Lys Glu Thr
1               5
```

```
<210> SEQ ID NO 230
<211> LENGTH: 7
<212> TYPE: PRT
<213> ORGANISM: artificial sequence
<220> FEATURE:
<223> OTHER INFORMATION: Hair binding peptide

<400> SEQUENCE: 230

Lys Gln Ser His Asn Pro Pro
1               5

<210> SEQ ID NO 231
<211> LENGTH: 9
<212> TYPE: PRT
<213> ORGANISM: artificial sequence
<220> FEATURE:
<223> OTHER INFORMATION: Hair binding peptide

<400> SEQUENCE: 231

Ser Thr Leu His Lys Tyr Lys Ser Gln
1               5

<210> SEQ ID NO 232
<211> LENGTH: 12
<212> TYPE: PRT
<213> ORGANISM: artificial sequence
<220> FEATURE:
<223> OTHER INFORMATION: Hair binding peptide

<400> SEQUENCE: 232

Tyr Pro Ser Phe Ser Pro Thr Tyr Arg Pro Ala Phe
1               5                   10

<210> SEQ ID NO 233
<211> LENGTH: 12
<212> TYPE: PRT
<213> ORGANISM: artificial sequence
<220> FEATURE:
<223> OTHER INFORMATION: Hair binding peptide

<400> SEQUENCE: 233

Ala Leu Pro Arg Ile Ala Asn Thr Trp Ser Pro Ser
1               5                   10

<210> SEQ ID NO 234
<211> LENGTH: 8
<212> TYPE: PRT
<213> ORGANISM: artificial sequence
<220> FEATURE:
<223> OTHER INFORMATION: Hair binding peptide

<400> SEQUENCE: 234

Leu Glu Ser Thr Pro Lys Met Lys
1               5

<210> SEQ ID NO 235
<211> LENGTH: 67
<212> TYPE: PRT
<213> ORGANISM: artificial sequence
<220> FEATURE:
<223> OTHER INFORMATION: Hair binding peptide

<400> SEQUENCE: 235

Pro Asn Thr Ser Gln Leu Ser Thr Gly Gly Gly Arg Thr Asn Ala Ala
1               5                   10                  15

Asp His Pro Lys Cys Gly Gly Gly Asn Thr Ser Gln Leu Ser Thr Gly
```

```
                    20                  25                  30

Gly Gly Arg Thr Asn Ala Ala Asp His Pro Lys Cys Gly Gly Asn
            35                  40                  45

Thr Ser Gln Leu Ser Thr Gly Gly Gly Arg Thr Asn Ala Ala Asp His
     50                  55                  60

Pro Lys Cys
 65

<210> SEQ ID NO 236
<211> LENGTH: 56
<212> TYPE: PRT
<213> ORGANISM: artificial sequence
<220> FEATURE:
<223> OTHER INFORMATION: Hair binding peptide

<400> SEQUENCE: 236

Asp Pro Arg Thr Asn Ala Ala Asp His Pro Ala Ala Val Thr Gly Gly
 1               5                  10                  15

Gly Cys Gly Gly Gly Arg Thr Asn Ala Ala Asp His Pro Ala Ala Val
            20                  25                  30

Thr Gly Gly Gly Cys Gly Gly Gly Arg Thr Asn Ala Ala Asp His Pro
         35                  40                  45

Ala Ala Val Thr Gly Gly Gly Cys
     50                  55

<210> SEQ ID NO 237
<211> LENGTH: 51
<212> TYPE: PRT
<213> ORGANISM: artificial sequence
<220> FEATURE:
<223> OTHER INFORMATION: Hair binding peptide

<400> SEQUENCE: 237

Asp Pro Arg Thr Asn Ala Ala Asp His Pro Ala Ala Val Thr Gly Gly
 1               5                  10                  15

Gly Cys Gly Gly Gly Ile Pro Trp Trp Asn Ile Arg Ala Pro Leu Asn
            20                  25                  30

Ala Gly Gly Gly Cys Gly Gly Gly Asp Leu Thr Leu Pro Phe His Gly
         35                  40                  45

Gly Gly Cys
     50

<210> SEQ ID NO 238
<211> LENGTH: 58
<212> TYPE: PRT
<213> ORGANISM: artificial sequence
<220> FEATURE:
<223> OTHER INFORMATION: Hair binding peptide

<400> SEQUENCE: 238

Arg Thr Asn Ala Ala Asp His Pro Ala Ala Val Thr Gly Gly Gly Cys
 1               5                  10                  15

Asp Pro Gly Gly Gly Arg Thr Asn Ala Ala Asp His Pro Ala Ala Val
            20                  25                  30

Thr Gly Gly Gly Cys Asp Pro Gly Gly Gly Arg Thr Asn Ala Ala Asp
         35                  40                  45

His Pro Ala Ala Val Thr Gly Gly Gly Cys
     50                  55

<210> SEQ ID NO 239
```

```
<211> LENGTH: 83
<212> TYPE: PRT
<213> ORGANISM: artificial sequence
<220> FEATURE:
<223> OTHER INFORMATION: Hair binding peptide

<400> SEQUENCE: 239

Asp Pro Thr Pro Pro Thr Asn Val Leu Met Leu Ala Thr Lys Gly Gly
1               5                   10                  15

Gly Arg Thr Asn Ala Ala Asp His Pro Lys Cys Gly Gly Gly Thr Pro
                20                  25                  30

Pro Thr Asn Val Leu Met Leu Ala Thr Lys Gly Gly Gly Arg Thr Asn
            35                  40                  45

Ala Ala Asp His Pro Lys Cys Gly Gly Gly Thr Pro Pro Thr Asn Val
        50                  55                  60

Leu Met Leu Ala Thr Lys Gly Gly Gly Arg Thr Asn Ala Ala Asp His
65                  70                  75                  80

Pro Lys Cys

<210> SEQ ID NO 240
<211> LENGTH: 83
<212> TYPE: PRT
<213> ORGANISM: artificial sequence
<220> FEATURE:
<223> OTHER INFORMATION: Hair binding peptide

<400> SEQUENCE: 240

Asp Pro Arg Thr Asn Ala Ala Asp His Pro Gly Gly Gly Thr Pro Pro
1               5                   10                  15

Thr Asn Val Leu Met Leu Ala Thr Lys Lys Cys Gly Gly Gly Arg Thr
                20                  25                  30

Asn Ala Ala Asp His Pro Gly Gly Gly Thr Pro Pro Thr Asn Val Leu
            35                  40                  45

Met Leu Ala Thr Lys Lys Cys Gly Gly Gly Arg Thr Asn Ala Ala Asp
        50                  55                  60

His Pro Gly Gly Gly Thr Pro Pro Thr Asn Val Leu Met Leu Ala Thr
65                  70                  75                  80

Lys Lys Cys

<210> SEQ ID NO 241
<211> LENGTH: 12
<212> TYPE: PRT
<213> ORGANISM: artificial sequence
<220> FEATURE:
<223> OTHER INFORMATION: Nail binding peptide

<400> SEQUENCE: 241

Ala Leu Pro Arg Ile Ala Asn Thr Trp Ser Pro Ser
1               5                   10

<210> SEQ ID NO 242
<211> LENGTH: 12
<212> TYPE: PRT
<213> ORGANISM: artificial sequence
<220> FEATURE:
<223> OTHER INFORMATION: Nail binding peptide

<400> SEQUENCE: 242

Tyr Pro Ser Phe Ser Pro Thr Tyr Arg Pro Ala Phe
1               5                   10
```

```
<210> SEQ ID NO 243
<211> LENGTH: 17
<212> TYPE: PRT
<213> ORGANISM: artificial sequence
<220> FEATURE:
<223> OTHER INFORMATION: Antimicrobial peptide

<400> SEQUENCE: 243

Pro Lys Gly Leu Lys Lys Leu Leu Lys Gly Leu Lys Lys Leu Leu Lys
1               5                   10                  15

Leu

<210> SEQ ID NO 244
<211> LENGTH: 16
<212> TYPE: PRT
<213> ORGANISM: artificial sequence
<220> FEATURE:
<223> OTHER INFORMATION: Antimicrobial peptide

<400> SEQUENCE: 244

Lys Gly Leu Lys Lys Leu Leu Lys Gly Leu Lys Lys Leu Leu Lys Leu
1               5                   10                  15

<210> SEQ ID NO 245
<211> LENGTH: 16
<212> TYPE: PRT
<213> ORGANISM: artificial sequence
<220> FEATURE:
<223> OTHER INFORMATION: Antimicrobial peptide

<400> SEQUENCE: 245

Lys Gly Leu Lys Lys Leu Leu Lys Leu Leu Lys Lys Leu Leu Lys Leu
1               5                   10                  15

<210> SEQ ID NO 246
<211> LENGTH: 14
<212> TYPE: PRT
<213> ORGANISM: artificial sequence
<220> FEATURE:
<223> OTHER INFORMATION: Antimicrobial peptide

<400> SEQUENCE: 246

Leu Lys Lys Leu Leu Lys Leu Leu Lys Lys Leu Leu Lys Leu
1               5                   10

<210> SEQ ID NO 247
<211> LENGTH: 12
<212> TYPE: PRT
<213> ORGANISM: artificial sequence
<220> FEATURE:
<223> OTHER INFORMATION: Antimicrobial peptide

<400> SEQUENCE: 247

Leu Lys Lys Leu Leu Lys Leu Leu Lys Lys Leu Leu
1               5                   10

<210> SEQ ID NO 248
<211> LENGTH: 17
<212> TYPE: PRT
<213> ORGANISM: artificial sequence
<220> FEATURE:
<223> OTHER INFORMATION: Antimicrobial peptide

<400> SEQUENCE: 248

Val Ala Lys Lys Leu Ala Lys Leu Ala Lys Lys Leu Ala Lys Leu Ala
1               5                   10                  15
```

Leu

<210> SEQ ID NO 249
<211> LENGTH: 13
<212> TYPE: PRT
<213> ORGANISM: artificial sequence
<220> FEATURE:
<223> OTHER INFORMATION: Antimicrobial peptide

<400> SEQUENCE: 249

Phe Ala Lys Leu Leu Ala Lys Ala Leu Lys Lys Leu Leu
1               5                   10

<210> SEQ ID NO 250
<211> LENGTH: 16
<212> TYPE: PRT
<213> ORGANISM: artificial sequence
<220> FEATURE:
<223> OTHER INFORMATION: Antimicrobial peptide

<400> SEQUENCE: 250

Lys Gly Leu Lys Lys Gly Leu Lys Leu Leu Lys Lys Leu Leu Lys Leu
1               5                   10                  15

<210> SEQ ID NO 251
<211> LENGTH: 16
<212> TYPE: PRT
<213> ORGANISM: artificial sequence
<220> FEATURE:
<223> OTHER INFORMATION: Antimicrobial peptide

<400> SEQUENCE: 251

Lys Gly Leu Lys Lys Leu Leu Lys Leu Gly Lys Lys Leu Leu Lys Leu
1               5                   10                  15

<210> SEQ ID NO 252
<211> LENGTH: 16
<212> TYPE: PRT
<213> ORGANISM: artificial sequence
<220> FEATURE:
<223> OTHER INFORMATION: Antimicrobial peptide

<400> SEQUENCE: 252

Lys Gly Leu Lys Lys Leu Gly Lys Leu Leu Lys Lys Leu Leu Lys Leu
1               5                   10                  15

<210> SEQ ID NO 253
<211> LENGTH: 16
<212> TYPE: PRT
<213> ORGANISM: artificial sequence
<220> FEATURE:
<223> OTHER INFORMATION: Antimicrobial peptide

<400> SEQUENCE: 253

Lys Gly Leu Lys Lys Leu Leu Lys Leu Leu Lys Gly Leu Leu Lys Leu
1               5                   10                  15

<210> SEQ ID NO 254
<211> LENGTH: 16
<212> TYPE: PRT
<213> ORGANISM: artificial sequence
<220> FEATURE:
<223> OTHER INFORMATION: Antimicrobial peptide

<400> SEQUENCE: 254

Lys Gly Leu Lys Lys Leu Leu Lys Leu Leu Lys Lys Leu Gly Lys Leu
1               5                   10                  15

<210> SEQ ID NO 255
<211> LENGTH: 19
<212> TYPE: PRT
<213> ORGANISM: artificial sequence
<220> FEATURE:
<223> OTHER INFORMATION: Antimicrobial peptide

<400> SEQUENCE: 255

Phe Ala Leu Ala Leu Lys Ala Leu Lys Lys Leu Lys Lys Ala Leu Lys
1               5                   10                  15

Lys Ala Leu

<210> SEQ ID NO 256
<211> LENGTH: 17
<212> TYPE: PRT
<213> ORGANISM: artificial sequence
<220> FEATURE:
<223> OTHER INFORMATION: Antimicrobial peptide

<400> SEQUENCE: 256

Phe Ala Lys Lys Leu Ala Lys Leu Ala Lys Lys Leu Ala Lys Leu Ala
1               5                   10                  15

Leu

<210> SEQ ID NO 257
<211> LENGTH: 13
<212> TYPE: PRT
<213> ORGANISM: artificial sequence
<220> FEATURE:
<223> OTHER INFORMATION: Antimicrobial peptide

<400> SEQUENCE: 257

Phe Ala Lys Leu Leu Ala Lys Leu Ala Lys Lys Leu Leu
1               5                   10

<210> SEQ ID NO 258
<211> LENGTH: 15
<212> TYPE: PRT
<213> ORGANISM: artificial sequence
<220> FEATURE:
<223> OTHER INFORMATION: Antimicrobial peptide

<400> SEQUENCE: 258

Phe Ala Lys Lys Leu Ala Lys Leu Ala Leu Lys Leu Ala Lys Leu
1               5                   10                  15

<210> SEQ ID NO 259
<211> LENGTH: 10
<212> TYPE: PRT
<213> ORGANISM: artificial sequence
<220> FEATURE:
<223> OTHER INFORMATION: Antimicrobial peptide

<400> SEQUENCE: 259

Phe Ala Lys Lys Leu Ala Lys Lys Leu Leu
1               5                   10

<210> SEQ ID NO 260
<211> LENGTH: 13
<212> TYPE: PRT
<213> ORGANISM: artificial sequence
<220> FEATURE:
<223> OTHER INFORMATION: Antimicrobial peptide

<400> SEQUENCE: 260

-continued

Phe Ala Lys Leu Leu Ala Lys Leu Ala Lys Lys Val Leu
1               5                   10

<210> SEQ ID NO 261
<211> LENGTH: 13
<212> TYPE: PRT
<213> ORGANISM: artificial sequence
<220> FEATURE:
<223> OTHER INFORMATION: Antimicrobial peptide

<400> SEQUENCE: 261

Lys Tyr Lys Lys Ala Leu Lys Lys Leu Ala Lys Leu Leu
1               5                   10

<210> SEQ ID NO 262
<211> LENGTH: 12
<212> TYPE: PRT
<213> ORGANISM: artificial sequence
<220> FEATURE:
<223> OTHER INFORMATION: Antimicrobial peptide

<400> SEQUENCE: 262

Phe Ala Leu Leu Lys Ala Leu Leu Lys Lys Ala Leu
1               5                   10

<210> SEQ ID NO 263
<211> LENGTH: 14
<212> TYPE: PRT
<213> ORGANISM: artificial sequence
<220> FEATURE:
<223> OTHER INFORMATION: Antimicrobial peptide

<400> SEQUENCE: 263

Lys Arg Leu Phe Lys Lys Leu Lys Phe Ser Leu Arg Lys Tyr
1               5                   10

<210> SEQ ID NO 264
<211> LENGTH: 14
<212> TYPE: PRT
<213> ORGANISM: artificial sequence
<220> FEATURE:
<223> OTHER INFORMATION: Antimicrobial peptide

<400> SEQUENCE: 264

Lys Arg Leu Phe Lys Lys Leu Leu Phe Ser Leu Arg Lys Tyr
1               5                   10

<210> SEQ ID NO 265
<211> LENGTH: 14
<212> TYPE: PRT
<213> ORGANISM: artificial sequence
<220> FEATURE:
<223> OTHER INFORMATION: Antimicrobial peptide

<400> SEQUENCE: 265

Leu Leu Leu Phe Leu Leu Lys Lys Arg Lys Lys Arg Lys Tyr
1               5                   10

<210> SEQ ID NO 266
<211> LENGTH: 36
<212> TYPE: PRT
<213> ORGANISM: Hyalophora cecropia

<400> SEQUENCE: 266

Lys Trp Lys Leu Phe Lys Lys Ile Glu Lys Val Gly Gln Asn Ile Arg
1               5                   10                  15

Asp Gly Ile Ile Lys Ala Gly Pro Ala Val Ala Trp Gly Gln Ala Thr
            20                  25                  30

Gln Ile Ala Lys
        35

<210> SEQ ID NO 267
<211> LENGTH: 23
<212> TYPE: PRT
<213> ORGANISM: Xenopus sp.

<400> SEQUENCE: 267

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 268
<211> LENGTH: 22
<212> TYPE: PRT
<213> ORGANISM: Xenopus sp.

<400> SEQUENCE: 268

Gly Ile Gly Lys Phe Leu Lys Lys Ala Lys Lys Phe Gly Lys Ala Phe
1               5                   10                  15

Val Lys Ile Leu Lys Lys
            20

<210> SEQ ID NO 269
<211> LENGTH: 12
<212> TYPE: PRT
<213> ORGANISM: Bos Taurus

<400> SEQUENCE: 269

Arg Leu Cys Arg Ile Val Val Ile Arg Val Cys Arg
1               5                   10

<210> SEQ ID NO 270
<211> LENGTH: 13
<212> TYPE: PRT
<213> ORGANISM: Bos sp.

<400> SEQUENCE: 270

Ile Leu Pro Trp Lys Trp Pro Trp Trp Pro Trp Arg Arg
1               5                   10

<210> SEQ ID NO 271
<211> LENGTH: 24
<212> TYPE: PRT
<213> ORGANISM: Homo sapiens

<400> SEQUENCE: 271

Asp Ser His Ala Lys Arg His His Gly Tyr Lys Arg Lys Phe His Glu
1               5                   10                  15

Lys His His Ser His Arg Gly Tyr
            20

<210> SEQ ID NO 272
<211> LENGTH: 7
<212> TYPE: PRT
<213> ORGANISM: artificial sequence
<220> FEATURE:
<223> OTHER INFORMATION: Carbon black binding peptide

```
<400> SEQUENCE: 272

Met Pro Pro Pro Leu Met Gln
1               5

<210> SEQ ID NO 273
<211> LENGTH: 7
<212> TYPE: PRT
<213> ORGANISM: artificial sequence
<220> FEATURE:
<223> OTHER INFORMATION: Carbon black binding peptide

<400> SEQUENCE: 273

Phe His Glu Asn Trp Pro Ser
1               5

<210> SEQ ID NO 274
<211> LENGTH: 12
<212> TYPE: PRT
<213> ORGANISM: artificial sequence
<220> FEATURE:
<223> OTHER INFORMATION: Carbon black binding peptide

<400> SEQUENCE: 274

Arg Thr Ala Pro Thr Thr Pro Leu Leu Leu Ser Leu
1               5                   10

<210> SEQ ID NO 275
<211> LENGTH: 12
<212> TYPE: PRT
<213> ORGANISM: artificial sequence
<220> FEATURE:
<223> OTHER INFORMATION: Carbon black binding peptide

<400> SEQUENCE: 275

Trp His Leu Ser Trp Ser Pro Val Pro Leu Pro Thr
1               5                   10

<210> SEQ ID NO 276
<211> LENGTH: 7
<212> TYPE: PRT
<213> ORGANISM: artificial sequence
<220> FEATURE:
<223> OTHER INFORMATION: Cromophtal Yellow binding peptide

<400> SEQUENCE: 276

Pro His Ala Arg Leu Val Gly
1               5

<210> SEQ ID NO 277
<211> LENGTH: 7
<212> TYPE: PRT
<213> ORGANISM: artificial sequence
<220> FEATURE:
<223> OTHER INFORMATION: Cromophtal Yellow binding peptide

<400> SEQUENCE: 277

Asn Ile Pro Tyr His His Pro
1               5

<210> SEQ ID NO 278
<211> LENGTH: 7
<212> TYPE: PRT
<213> ORGANISM: artificial sequence
<220> FEATURE:
<223> OTHER INFORMATION: Cromophtal Yellow binding peptide

<400> SEQUENCE: 278
```

Thr Thr Met Pro Ala Ile Pro
1               5

<210> SEQ ID NO 279
<211> LENGTH: 7
<212> TYPE: PRT
<213> ORGANISM: artificial sequence
<220> FEATURE:
<223> OTHER INFORMATION: Cromophtal Yellow binding peptide

<400> SEQUENCE: 279

His Asn Leu Pro Pro Arg Ser
1               5

<210> SEQ ID NO 280
<211> LENGTH: 12
<212> TYPE: PRT
<213> ORGANISM: artificial sequence
<220> FEATURE:
<223> OTHER INFORMATION: Cromophtal Yellow binding peptide

<400> SEQUENCE: 280

Ala His Lys Thr Gln Met Gly Val Arg Gln Pro Ala
1               5                   10

<210> SEQ ID NO 281
<211> LENGTH: 12
<212> TYPE: PRT
<213> ORGANISM: artificial sequence
<220> FEATURE:
<223> OTHER INFORMATION: Cromophtal Yellow binding peptide

<400> SEQUENCE: 281

Ala Asp Asn Val Gln Met Gly Val Ser His Thr Pro
1               5                   10

<210> SEQ ID NO 282
<211> LENGTH: 12
<212> TYPE: PRT
<213> ORGANISM: artificial sequence
<220> FEATURE:
<223> OTHER INFORMATION: Cromophtal Yellow binding peptide

<400> SEQUENCE: 282

Ala His Asn Ala Gln Met Gly Val Ser His Pro Pro
1               5                   10

<210> SEQ ID NO 283
<211> LENGTH: 12
<212> TYPE: PRT
<213> ORGANISM: artificial sequence
<220> FEATURE:
<223> OTHER INFORMATION: Cromophtal Yellow binding peptide

<400> SEQUENCE: 283

Ala Asp Tyr Val Gly Met Gly Val Ser His Arg Pro
1               5                   10

<210> SEQ ID NO 284
<211> LENGTH: 12
<212> TYPE: PRT
<213> ORGANISM: artificial sequence
<220> FEATURE:
<223> OTHER INFORMATION: Cromophtal Yellow binding peptide

<400> SEQUENCE: 284

-continued

```
Ser Val Ser Val Gly Met Lys Pro Ser Pro Arg Pro
1               5                   10

<210> SEQ ID NO 285
<211> LENGTH: 7
<212> TYPE: PRT
<213> ORGANISM: artificial sequence
<220> FEATURE:
<223> OTHER INFORMATION: Sunfast Magenta binding peptide

<400> SEQUENCE: 285

Tyr Pro Asn Thr Ala Leu Val
1               5

<210> SEQ ID NO 286
<211> LENGTH: 7
<212> TYPE: PRT
<213> ORGANISM: artificial sequence
<220> FEATURE:
<223> OTHER INFORMATION: Sunfast Magenta binding peptide

<400> SEQUENCE: 286

Val Ala Thr Arg Ile Val Ser
1               5

<210> SEQ ID NO 287
<211> LENGTH: 12
<212> TYPE: PRT
<213> ORGANISM: artificial sequence
<220> FEATURE:
<223> OTHER INFORMATION: Sunfast Magenta binding peptide

<400> SEQUENCE: 287

His Ser Leu Lys Asn Ser Met Leu Thr Val Met Ala
1               5                   10

<210> SEQ ID NO 288
<211> LENGTH: 7
<212> TYPE: PRT
<213> ORGANISM: artificial sequence
<220> FEATURE:
<223> OTHER INFORMATION: Sunfast Blue binding peptide

<400> SEQUENCE: 288

Asn Tyr Pro Thr Gln Ala Pro
1               5

<210> SEQ ID NO 289
<211> LENGTH: 7
<212> TYPE: PRT
<213> ORGANISM: artificial sequence
<220> FEATURE:
<223> OTHER INFORMATION: Sunfast Blue binding peptide

<400> SEQUENCE: 289

Lys Cys Cys Tyr Ser Val Gly
1               5

<210> SEQ ID NO 290
<211> LENGTH: 12
<212> TYPE: PRT
<213> ORGANISM: artificial sequence
<220> FEATURE:
<223> OTHER INFORMATION: Sunfast Blue binding peptide

<400> SEQUENCE: 290

Arg His Asp Leu Asn Thr Trp Leu Pro Pro Val Lys
```

-continued

<210> SEQ ID NO 291
<211> LENGTH: 12
<212> TYPE: PRT
<213> ORGANISM: artificial sequence
<220> FEATURE:
<223> OTHER INFORMATION: Sunfast Blue binding peptide

<400> SEQUENCE: 291

Glu Ile Ser Leu Pro Ala Lys Leu Pro Ser Ala Ser
1               5                   10

<210> SEQ ID NO 292
<211> LENGTH: 12
<212> TYPE: PRT
<213> ORGANISM: artificial sequence
<220> FEATURE:
<223> OTHER INFORMATION: Sunfast Blue binding peptide

<400> SEQUENCE: 292

Ser Val Ser Val Gly Met Lys Pro Ser Pro Arg Pro
1               5                   10

<210> SEQ ID NO 293
<211> LENGTH: 12
<212> TYPE: PRT
<213> ORGANISM: artificial sequence
<220> FEATURE:
<223> OTHER INFORMATION: Sunfast Blue binding peptide

<400> SEQUENCE: 293

Ser Asp Tyr Val Gly Met Arg Pro Ser Pro Arg His
1               5                   10

<210> SEQ ID NO 294
<211> LENGTH: 12
<212> TYPE: PRT
<213> ORGANISM: artificial sequence
<220> FEATURE:
<223> OTHER INFORMATION: Sunfast Blue binding peptide

<400> SEQUENCE: 294

Ser Asp Tyr Val Gly Met Arg Leu Ser Pro Ser Gln
1               5                   10

<210> SEQ ID NO 295
<211> LENGTH: 12
<212> TYPE: PRT
<213> ORGANISM: artificial sequence
<220> FEATURE:
<223> OTHER INFORMATION: Sunfast Blue binding peptide

<400> SEQUENCE: 295

Ser Val Ser Val Gly Ile Gln Pro Ser Pro Arg Pro
1               5                   10

<210> SEQ ID NO 296
<211> LENGTH: 12
<212> TYPE: PRT
<213> ORGANISM: artificial sequence
<220> FEATURE:
<223> OTHER INFORMATION: Sunfast Blue binding peptide

<400> SEQUENCE: 296

Tyr Val Ser Val Gly Ile Lys Pro Ser Pro Arg Pro
1               5                   10

```
<210> SEQ ID NO 297
<211> LENGTH: 12
<212> TYPE: PRT
<213> ORGANISM: artificial sequence
<220> FEATURE:
<223> OTHER INFORMATION: Sunfast Blue binding peptide

<400> SEQUENCE: 297

Tyr Val Cys Glu Gly Ile His Pro Cys Pro Arg Pro
1               5                   10

<210> SEQ ID NO 298
<211> LENGTH: 7
<212> TYPE: PRT
<213> ORGANISM: artificial sequence
<220> FEATURE:
<223> OTHER INFORMATION: Cellulose binding peptide

<400> SEQUENCE: 298

Val Pro Arg Val Thr Ser Ile
1               5

<210> SEQ ID NO 299
<211> LENGTH: 7
<212> TYPE: PRT
<213> ORGANISM: artificial sequence
<220> FEATURE:
<223> OTHER INFORMATION: Cellulose binding peptide

<400> SEQUENCE: 299

Met Ala Asn His Asn Leu Ser
1               5

<210> SEQ ID NO 300
<211> LENGTH: 7
<212> TYPE: PRT
<213> ORGANISM: artificial sequence
<220> FEATURE:
<223> OTHER INFORMATION: Cellulose binding peptide

<400> SEQUENCE: 300

Phe His Glu Asn Trp Pro Ser
1               5

<210> SEQ ID NO 301
<211> LENGTH: 12
<212> TYPE: PRT
<213> ORGANISM: artificial sequence
<220> FEATURE:
<223> OTHER INFORMATION: Cellulose binding peptide

<400> SEQUENCE: 301

Thr His Lys Thr Ser Thr Gln Arg Leu Leu Ala Ala
1               5                   10

<210> SEQ ID NO 302
<211> LENGTH: 12
<212> TYPE: PRT
<213> ORGANISM: artificial sequence
<220> FEATURE:
<223> OTHER INFORMATION: Cellulose binding peptide

<400> SEQUENCE: 302

Lys Cys Cys Tyr Val Asn Val Gly Ser Val Phe Ser
1               5                   10
```

```
<210> SEQ ID NO 303
<211> LENGTH: 12
<212> TYPE: PRT
<213> ORGANISM: artificial sequence
<220> FEATURE:
<223> OTHER INFORMATION: Cellulose binding peptide

<400> SEQUENCE: 303

Ala His Met Gln Phe Arg Thr Ser Leu Thr Pro His
1               5                   10

<210> SEQ ID NO 304
<211> LENGTH: 12
<212> TYPE: PRT
<213> ORGANISM: artificial sequence
<220> FEATURE:
<223> OTHER INFORMATION: Poly(ethylene terephthalate) binding peptide

<400> SEQUENCE: 304

Gly Thr Ser Asp His Met Ile Met Pro Phe Phe Asn
1               5                   10

<210> SEQ ID NO 305
<211> LENGTH: 12
<212> TYPE: PRT
<213> ORGANISM: artificial sequence
<220> FEATURE:
<223> OTHER INFORMATION: Poly(methyl methacrylate) binding peptide

<400> SEQUENCE: 305

Ile Pro Trp Trp Asn Ile Arg Ala Pro Leu Asn Ala
1               5                   10

<210> SEQ ID NO 306
<211> LENGTH: 12
<212> TYPE: PRT
<213> ORGANISM: artificial sequence
<220> FEATURE:
<223> OTHER INFORMATION: Poly(methyl methacrylate) binding peptide

<400> SEQUENCE: 306

Thr Ala Val Met Asn Val Val Asn Asn Gln Leu Ser
1               5                   10

<210> SEQ ID NO 307
<211> LENGTH: 12
<212> TYPE: PRT
<213> ORGANISM: artificial sequence
<220> FEATURE:
<223> OTHER INFORMATION: Poly(methyl methacrylate) binding peptide

<400> SEQUENCE: 307

Val Pro Trp Trp Ala Pro Ser Lys Leu Ser Met Gln
1               5                   10

<210> SEQ ID NO 308
<211> LENGTH: 12
<212> TYPE: PRT
<213> ORGANISM: artificial sequence
<220> FEATURE:
<223> OTHER INFORMATION: Poly(methyl methacrylate) binding peptide

<400> SEQUENCE: 308

Met Val Met Ala Pro His Thr Pro Arg Ala Arg Ser
1               5                   10
```

```
<210> SEQ ID NO 309
<211> LENGTH: 12
<212> TYPE: PRT
<213> ORGANISM: artificial sequence
<220> FEATURE:
<223> OTHER INFORMATION: Poly(methyl methacrylate) binding peptide

<400> SEQUENCE: 309

Thr Tyr Pro Asn Trp Ala His Leu Leu Ser His Tyr
1               5                   10

<210> SEQ ID NO 310
<211> LENGTH: 7
<212> TYPE: PRT
<213> ORGANISM: artificial sequence
<220> FEATURE:
<223> OTHER INFORMATION: Poly(methyl methacrylate) binding peptide

<400> SEQUENCE: 310

Thr Pro Trp Trp Arg Ile Thr
1               5

<210> SEQ ID NO 311
<211> LENGTH: 7
<212> TYPE: PRT
<213> ORGANISM: artificial sequence
<220> FEATURE:
<223> OTHER INFORMATION: Poly(methyl methacrylate) binding peptide

<400> SEQUENCE: 311

Asp Leu Thr Leu Pro Phe His
1               5

<210> SEQ ID NO 312
<211> LENGTH: 7
<212> TYPE: PRT
<213> ORGANISM: artificial sequence
<220> FEATURE:
<223> OTHER INFORMATION: Poly(methyl methacrylate) binding peptide

<400> SEQUENCE: 312

Gly Thr Ser Ile Pro Ala Met
1               5

<210> SEQ ID NO 313
<211> LENGTH: 7
<212> TYPE: PRT
<213> ORGANISM: artificial sequence
<220> FEATURE:
<223> OTHER INFORMATION: Poly(methyl methacrylate) binding peptide

<400> SEQUENCE: 313

His His Lys His Val Val Ala
1               5

<210> SEQ ID NO 314
<211> LENGTH: 7
<212> TYPE: PRT
<213> ORGANISM: artificial sequence
<220> FEATURE:
<223> OTHER INFORMATION: Poly(methyl methacrylate) binding peptide

<400> SEQUENCE: 314

His His His Lys His Phe Met
1               5

<210> SEQ ID NO 315
```

```
<211> LENGTH: 7
<212> TYPE: PRT
<213> ORGANISM: artificial sequence
<220> FEATURE:
<223> OTHER INFORMATION: Poly(methyl methacrylate) binding peptide

<400> SEQUENCE: 315

His His His Arg His Gln Gly
1               5

<210> SEQ ID NO 316
<211> LENGTH: 7
<212> TYPE: PRT
<213> ORGANISM: artificial sequence
<220> FEATURE:
<223> OTHER INFORMATION: Poly(methyl methacrylate) binding peptide

<400> SEQUENCE: 316

His His Trp His Ala Pro Arg
1               5

<210> SEQ ID NO 317
<211> LENGTH: 7
<212> TYPE: PRT
<213> ORGANISM: artificial sequence
<220> FEATURE:
<223> OTHER INFORMATION: Nylon binding peptide

<400> SEQUENCE: 317

Lys Thr Pro Pro Thr Arg Pro
1               5

<210> SEQ ID NO 318
<211> LENGTH: 7
<212> TYPE: PRT
<213> ORGANISM: artificial sequence
<220> FEATURE:
<223> OTHER INFORMATION: Nylon binding peptide

<400> SEQUENCE: 318

Val Ile Asn Pro Asn Leu Asp
1               5

<210> SEQ ID NO 319
<211> LENGTH: 7
<212> TYPE: PRT
<213> ORGANISM: artificial sequence
<220> FEATURE:
<223> OTHER INFORMATION: Nylon binding peptide

<400> SEQUENCE: 319

Lys Val Trp Ile Val Ser Thr
1               5

<210> SEQ ID NO 320
<211> LENGTH: 7
<212> TYPE: PRT
<213> ORGANISM: artificial sequence
<220> FEATURE:
<223> OTHER INFORMATION: Nylon binding peptide

<400> SEQUENCE: 320

Ala Glu Pro Val Ala Met Leu
1               5

<210> SEQ ID NO 321
<211> LENGTH: 7
```

```
<212> TYPE: PRT
<213> ORGANISM: artificial sequence
<220> FEATURE:
<223> OTHER INFORMATION: Nylon binding peptide

<400> SEQUENCE: 321

Ala Glu Leu Val Ala Met Leu
1               5

<210> SEQ ID NO 322
<211> LENGTH: 7
<212> TYPE: PRT
<213> ORGANISM: artificial sequence
<220> FEATURE:
<223> OTHER INFORMATION: Nylon binding peptide

<400> SEQUENCE: 322

His Ser Leu Arg Leu Asp Trp
1               5

<210> SEQ ID NO 323
<211> LENGTH: 12
<212> TYPE: PRT
<213> ORGANISM: artificial sequence
<220> FEATURE:
<223> OTHER INFORMATION: Poly(tetrafluoroethylene) binding peptide

<400> SEQUENCE: 323

Glu Ser Ser Tyr Ser Trp Ser Pro Ala Arg Leu Ser
1               5                   10

<210> SEQ ID NO 324
<211> LENGTH: 12
<212> TYPE: PRT
<213> ORGANISM: artificial sequence
<220> FEATURE:
<223> OTHER INFORMATION: Poly(tetrafluoroethylene) binding peptide

<400> SEQUENCE: 324

Gly Pro Leu Lys Leu Leu His Ala Trp Trp Gln Pro
1               5                   10

<210> SEQ ID NO 325
<211> LENGTH: 7
<212> TYPE: PRT
<213> ORGANISM: artificial sequence
<220> FEATURE:
<223> OTHER INFORMATION: Poly(tetrafluoroethylene) binding peptide

<400> SEQUENCE: 325

Asn Ala Leu Thr Arg Pro Val
1               5

<210> SEQ ID NO 326
<211> LENGTH: 7
<212> TYPE: PRT
<213> ORGANISM: artificial sequence
<220> FEATURE:
<223> OTHER INFORMATION: Poly(tetrafluoroethylene) binding peptide

<400> SEQUENCE: 326

Ser Ala Pro Ser Ser Lys Asn
1               5

<210> SEQ ID NO 327
<211> LENGTH: 12
<212> TYPE: PRT
```

```
<213> ORGANISM: artificial sequence
<220> FEATURE:
<223> OTHER INFORMATION: Poly(tetrafluoroethylene) binding peptide

<400> SEQUENCE: 327

Ser Val Ser Val Gly Met Lys Pro Ser Pro Arg Pro
1               5                   10

<210> SEQ ID NO 328
<211> LENGTH: 12
<212> TYPE: PRT
<213> ORGANISM: artificial sequence
<220> FEATURE:
<223> OTHER INFORMATION: Poly(tetrafluoroethylene) binding peptide

<400> SEQUENCE: 328

Ser Tyr Tyr Ser Leu Pro Pro Ile Phe His Ile Pro
1               5                   10

<210> SEQ ID NO 329
<211> LENGTH: 12
<212> TYPE: PRT
<213> ORGANISM: artificial sequence
<220> FEATURE:
<223> OTHER INFORMATION: Poly(tetrafluoroethylene) binding peptide

<400> SEQUENCE: 329

Thr Phe Thr Pro Tyr Ser Ile Thr His Ala Leu Leu
1               5                   10

<210> SEQ ID NO 330
<211> LENGTH: 12
<212> TYPE: PRT
<213> ORGANISM: artificial sequence
<220> FEATURE:
<223> OTHER INFORMATION: Poly(tetrafluoroethylene) binding peptide

<400> SEQUENCE: 330

Thr Met Gly Phe Thr Ala Pro Arg Phe Pro His Tyr
1               5                   10

<210> SEQ ID NO 331
<211> LENGTH: 12
<212> TYPE: PRT
<213> ORGANISM: artificial sequence
<220> FEATURE:
<223> OTHER INFORMATION: Poly(tetrafluoroethylene) binding peptide

<400> SEQUENCE: 331

Thr Asn Pro Phe Pro Pro Pro Ser Ser Pro Ala
1               5                   10

<210> SEQ ID NO 332
<211> LENGTH: 5
<212> TYPE: PRT
<213> ORGANISM: artificial sequence
<220> FEATURE:
<223> OTHER INFORMATION: chemically synthesized
<220> FEATURE:
<221> NAME/KEY: MISC_FEATURE
<222> LOCATION: (5)..(5)
<223> OTHER INFORMATION: Xaa = any amino acid but Pro, Glu, Asp, Gln,
      Lys, and Arg

<400> SEQUENCE: 332

Asp Met Gln Asp Xaa
1               5
```

PEPTIDE TAGS FOR THE EXPRESSION AND PURIFICATION OF BIOACTIVE PEPTIDES

This application claims the benefit of U.S. Provisional Application No. 60/721,329 filed Sep. 28, 2005.

FIELD OF THE INVENTION

The invention relates to the field of protein expression and purification from microbial cells. More specifically, a family of peptide tags has been discovered that are useful in the generation of insoluble fusion proteins.

BACKGROUND OF THE INVENTION

The efficient production of bioactive proteins and peptides has become a hallmark of the biomedical and industrial biochemical industry. Bioactive peptides and proteins are used as curative agents in a variety of diseases such as diabetes (insulin), viral infections and leukemia (interferon), diseases of the immune system (interleukins), and red blood cell deficiencies (erythropoietin) to name a few. Additionally, large quantities of proteins and peptides are needed for various industrial applications including, for example, the pulp and paper and pulp industries, textiles, food industries, sugar refining, wastewater treatment, production of alcoholic beverages and as catalysts for the generation of new pharmaceuticals.

With the advent of the discovery and implementation of combinatorial peptide screening technologies such as bacterial display (Kemp, D. J.; *Proc. Natl. Acad. Sci. USA* 78(7): 4520-4524 (1981); yeast display (Chien et al., *Proc Natl Acad Sci USA* 88(21): 9578-82 (1991)), combinatorial solid phase peptide synthesis (U.S. Pat. No. 5,449,754, U.S. Pat. No. 5,480,971, U.S. Pat. No. 5,585,275, U.S. Pat. No. 5,639,603), and phage display technology (U.S. Pat. No. 5,223,409, U.S. Pat. No. 5,403,484, U.S. Pat. No. 5,571,698, U.S. Pat. No. 5,837,500) new applications for peptides having specific binding affinities have been developed. In particular, peptides are being looked to as linkers in biomedical fields for the attachment of diagnostic and pharmaceutical agents to surfaces (see Grinstaff et al, U.S. Patent Application Publication No. 2003/0185870 and Linter in U.S. Pat. No. 6,620,419), as well as in the personal care industry for the attachment of benefit agents to body surfaces such as hair and skin (see commonly owned U.S. patent application Ser. No. 10/935,642, and Janssen et al. U.S. Patent Application Publication No. 2003/0152976), and in the printing industry for the attachment of pigments to print media (see commonly owned U.S. patent application Ser. No. 10/935,254).

In some cases commercially useful proteins and peptides may be synthetically generated or isolated from natural sources. However, these methods are often expensive, time consuming and characterized by limited production capacity. The preferred method of protein and peptide production is through the fermentation of recombinantly constructed organisms, engineered to over-express the protein or peptide of interest. Although preferable to synthesis or isolation, recombinant expression of peptides has a number of obstacles to be overcome in order to be a cost-effective means of production. For example, peptides (and in particular short peptides) produced in a cellular environment are susceptible to degradation from the action of native cellular proteases. Additionally, purification can be difficult, resulting in poor yields depending on the nature of the protein or peptide of interest.

One means to mitigate the above difficulties is the use the genetic chimera for protein and peptide expression. A chimeric protein or "fusion protein" is a polypeptide comprising at least one portion of the desired protein product fused to at least one portion comprising a peptide tag. The peptide tag may be used to assist protein folding, assist post expression purification, protect the protein from the action of degradative enzymes, and/or assist the protein in passing through the cell membrane.

In many cases it is useful to express a protein or peptide in insoluble form, particularly when the peptide of interest is rather short, normally soluble, and subject to proteolytic degradation within the host cell. Production of the peptide in insoluble form both facilitates simple recovery and protects the peptide from the undesirable proteolytic degradation. One means to produce the peptide in insoluble form is to recombinantly produce the peptide as part of an insoluble fusion protein by including in the fusion construct at least one peptide tag (i.e., an inclusion body tag) that induces inclusion body formation. Typically, the fusion protein is designed to include at least one cleavable peptide linker so that the peptide of interest can be subsequently recovered from the fusion protein. The fusion protein may be designed to include a plurality of inclusion body tags, cleavable peptide linkers, and regions encoding the peptide of interest.

Fusion proteins comprising a peptide tag that facilitate the expression of insoluble proteins are well known in the art. Typically, the tag portion of the chimeric or fusion protein is large, increasing the likelihood that the fusion protein will be insoluble. Example of large peptide tides typically used include, but are not limited to chloramphenicol acetyltransferase (Dykes et al., *Eur. J. Biochem.*, 174:411 (1988), β-galactosidase (Schellenberger et al., *Int. J. Peptide Protein Res.*, 41:326 (1993); Shen et al., *Proc. Nat. Acad. Sci. USA* 281: 4627 (1984); and Kempe et al., *Gene*, 39:239 (1985)), glutathione-5-transferase (Ray et al., Bio/Technology, 11: 64 (1993) and Hancock et al. (WO94/04688)), the N-terminus of L-ribulokinase (U.S. Pat. No. 5,206,154 and Lai et al., *Antimicrob. Agents & Chemo.*, 37:1614 (1993), bacteriophage T4 gp55 protein (Gramm et al., *Bio/Technology*, 12: 1017 (1994), bacterial ketosteroid isomerase protein (Kuliopulos et al., *J. Am. Chem. Soc.* 116:4599 (1994), ubiquitin (Pilon et al., *Biotechnol. Prog.*, 13:374-79 (1997), bovine prochymosin (Haught et al., *Biotechnol. Bioengineer.* 57:55-61 (1998), and bactericidal/permeability-increasing protein ("BPI"; Better, M. D. and Gavit, P D., U.S. Pat. No. 6,242,219). The art is replete with specific examples of this technology, see for example U.S. Pat. No. 6,613,548, describing fusion protein of proteinaceous tag and a soluble protein and subsequent purification from cell lysate; U.S. Pat. No. 6,037,145, teaching a tag that protects the expressed chimeric protein from a specific protease; U.S. Pat. No. 5,648,244, teaching the synthesis of a fusion protein having a tag and a cleavable linker for facile purification of the desired protein; and U.S. Pat. No. 5,215,896; U.S. Pat. No. 5,302,526; U.S. Pat. No. 5,330,902; and US 2005221444, describing fusion tags containing amino acid compositions specifically designed to increase insolubility of the chimeric protein or peptide.

Although the above methods are useful for the expression of fusion proteins, they often incorporate large fusion tags that decrease the potential yield of desired peptide of interest. This is particularly problematic in situations where the desired protein or peptide is small. In such situations it is advantageous to use a small fusion tag to maximized yield.

There remains a need therefore for peptide fusion tags that facilitate the insolubility of fusion proteins where the peptide of interest is small and appreciably soluble in the host cell.

SUMMARY OF THE INVENTION

The stated problem has been solved though the discovery of a set of short inclusion body tags (IBTs) that are useful for synthesizing fusion proteins for increased expression and simple purification of short peptides ("peptides of interest"), especially short peptides useful in affinity applications.

The invention relates to a set of peptide inclusion body tags that may be linked to a peptide of interest to be expressed to facilitate insolubility and subsequent recovery of the expressed peptide. The inclusion body tags are generally short and may be cleaved from the fusion protein after recovery.

Accordingly the invention provides an inclusion body tag having the formula:

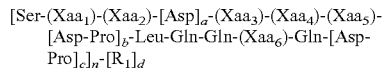

[Ser-(Xaa$_1$)-(Xaa$_2$)-[Asp]$_a$-(Xaa$_3$)-(Xaa$_4$)-(Xaa$_5$)-[Asp-Pro]$_b$-Leu-Gln-Gln-(Xaa$_6$)-Gln-[Asp-Pro]$_c$]$_n$-[R$_1$]$_d$ wherein a=0 or 1, b=0 or 1, c=0 or 1, d=0 or 1, and n=1-20
and wherein
(Xaa$_1$)=Arg or Glu;
(Xaa$_2$)=Arg or Glu;
(Xaa$_3$)=Pro or Gln;
(Xaa$_4$)=Arg, Glu, or Asp
(Xaa$_5$)=Gln or Pro;
(Xaa$_6$)=Arg or Glu;
and wherein when d=1 then n=1 or 2 and R$_1$ is selected from the group consisting of
a) His-His-Gln-Gln-Gln-Gln-Glu;
b) Ser-Leu-Gly-Tyr-Gly-Gly-Leu-Tyr-Gly-Tyr;
c) Glu-Glu;
d) Glu-Glu-Glu;
e) Glu-Glu-Glu-Glu; and
f) Glu-Glu-Glu-Glu-Glu.

wherein the inclusion body tag does not have the amino acid sequence as set forth in SEQ ID NO:139.

In an alternate embodiment the invention provides 2. An inclusion body tag comprising the structure:

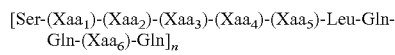

[Ser-(Xaa$_1$)-(Xaa$_2$)-(Xaa$_3$)-(Xaa$_4$)-(Xaa$_5$)-Leu-Gln-Gln-(Xaa$_6$)-Gln]$_n$ wherein n=1-20,
and wherein
(Xaa$_1$)=Arg or Glu;
(Xaa$_2$)=Arg or Glu;
(Xaa$_3$)=Pro or Gln;
(Xaa$_4$)=Arg, Glu, or Asp
(Xaa$_5$)=Gln or Pro;
(Xaa$_6$)=Arg or Glu;
wherein the inclusion body tag does not have the amino acid sequence as set forth in SEQ ID NO:139.

In another embodiment, the invention provides a fusion peptide comprising at least one of the present inclusion body tags operably linked to a peptide of interest. The inclusion body tag can be a leader or trailer sequence within the fusion protein. In a preferred aspect, the fusion peptide is engineered to include at least one cleavable peptide linker that separates the inclusion body tag and the peptide of interest. In a preferred aspect, the cleavable peptide linker comprises at least one acid cleavable aspartic acid—proline (DP) moiety.

In a further embodiment, the invention provides a method for expressing a peptide of interest in insoluble form comprising:

a) synthesizing a genetic construct encoding a fusion peptide comprising a first portion encoding the inclusion body tag of the invention operably linked to a second portion encoding a peptide of interest;
b) transforming an expression host cell with the genetic construct of (a);
c) growing the transformed host cell of (b) under conditions wherein the genetic construct is expressed and the encoded fusion peptide is in insoluble form; and
d) recovering said fusion peptide in insoluble form.

In another embodiment, a method for the production of a peptide of interest is provided comprising:

a) synthesizing a genetic construct encoding a fusion peptide comprising a first portion encoding the inclusion body tag of the invention operably linked to a second portion encoding a peptide of interest; wherein said first portion and said second portion are separated by at least one cleavable peptide linker;
b) transforming an expression host cell with the genetic construct of (a);
c) growing the transformed host cell of (b) under conditions wherein the genetic construct is expressed and the encoded fusion peptide is in insoluble form;
d) recovering the fusion peptide in insoluble form;
e) cleaving said at least one cleavable peptide linker whereby said first portion of the fusion peptide is no longer fused to the peptide of interest; and
f) recovering said peptide of interest.

In another embodiment, the invention provides a chimeric genetic construct encoding a fusion protein comprising at least one of the present inclusion body tags and at least one peptide of interest.

In yet another embodiment, the invention provides expression vectors and microbial host cells comprising the present chimeric genetic constructs.

BRIEF DESCRIPTION OF THE BIOLOGICAL SEQUENCES

The following sequences comply with 37 C.F.R. 1.821-1.825 ("Requirements for patent applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPC and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

A Sequence Listing is provided herewith on Compact Disk. The contents of the Compact Disk containing the Sequence Listing are hereby incorporated by reference in compliance with 37 CFR 1.52(e). The Compact Disks are submitted in triplicate and are identical to one another. The disks are labeled "Copy 1—Sequence Listing", "Copy 2—Sequence listing", and CRF. The disks contain the following file: CL2736 US NA.ST25 having the following size: 150,000 bytes and which was created Aug. 31, 2006.

SEQ ID NO: 1 is the nucleotide sequence of the TBP1 coding sequence encoding the TBP101 peptide.

SEQ ID NO: 2 is the amino acid sequence of the TBP101 peptide.

SEQ ID NOs: 3-7 are the nucleotide sequences of oligonucleotides used to synthesize TBP1.

SEQ ID NO: 8 and 9 are the nucleotide sequences of the primers used to PCR amplify TBP1.

SEQ ID NO: 10 is the nucleotide sequence of pENTR™/D-TOPO® plasmid (Invitrogen, Carlsbad, Calif.).

SEQ ID NO: 11 is the nucleotide sequence of the pDEST plasmid (Invitrogen).

SEQ ID NO: 12 is the nucleotide sequence of the coding region encoding the INK101 fusion peptide.

SEQ ID NO: 13 is the amino acid sequence of the INK101 fusion peptide.

SEQ ID NO: 14 is the nucleotide sequence of plasmid pLX121.

SEQ ID NOs: 15 and 16 are the nucleotide sequences of primers used to introduce an acid cleavable aspartic acid-proline dipeptide linker into TBP101.

SEQ ID NO: 17 is the nucleotide sequence of the coding region encoding the INK101DP peptide.

SEQ ID NO: 18 is the amino acid sequence of the INK101 DP peptide (also referred to herein as "TBP101DP").

SEQ ID NOs: 19-66 are the nucleotide sequences of oligonucleotides used to prepare the present inclusion body tags.

SEQ ID NOs: 67-90 are the amino acid sequences of the present inclusion body tags.

SEQ ID NOs: 91-136 are the nucleotide and corresponding amino acid sequences of the fusion proteins created by fusing the present inclusion body tags to the TBP101 peptide.

SEQ ID NO: 137 is the amino acid sequence of the core sequence found within many of the present inclusion body tags.

SEQ ID NO: 138 is the nucleic acid sequence of a hypothetical protein from *Caenorhabditis elegans* having GenBanke accession number MK68556.

SEQ ID NO: 139 is the amino acid sequence a hypothetical protein from *Caenorhabditis elegans* having GenBank® accession number AAK68556.

SEQ ID NOs: 140-246 are examples of amino acid sequences of body surface binding peptides, SEQ ID NOs 140-147 are skin binding peptides, SEQ ID NOs 148-240 are hair binding peptides, and SEQ ID NOs: 241-242 are nail binding peptides.

SEQ ID NOs: 243-271 are examples of antimicrobial peptide sequences.

SEQ ID NOs: 272-297 are examples of pigment binding peptides,

SEQ ID NOs: 272-275 bind carbon black, SEQ ID NOs: 276-284 are Cromophtal® yellow (Ciba Specialty Chemicals, Basel, Switzerland) binding peptides, SEQ ID NOs: 285-287 are Sunfast® magenta (Sun Chemical Corp., Parsippany, N.J.) binding peptides, and SEQ ID NOs: 288-297 are Sunfast® blue binding peptides.

SEQ ID NOs: 298-331 are examples of polymer binding peptides, SEQ ID NOs: 298-303 are cellulose binding peptides, SEQ ID NO: 304 is a poly(ethylene terephthalate) (PET) binding peptide, SEQ ID NOs: 305-316 are poly(methyl methacrylate) (PMMA) binding peptides, SEQ ID NOs: 317-322 Nylon binding peptides, and SEQ ID NOs: 323-331 are poly(tetrafluoro ethylene) (PTFE) binding peptides.

SEQ ID NO: 332 is the amino acid sequence of the Caspase-3 cleavage site that may be used as a cleavable peptide linker domain.

DETAILED DESCRIPTION OF THE INVENTION

The present invention describes a set of peptide tags (inclusion body tags) that may be coupled with a peptide of interest to form a fusion protein. The fusion protein, so assembled, is expressed in insoluble form and accumulated in inclusion bodies in the expressing host cell. The inclusion bodies may then be recovered and the desired protein cleaved from the inclusion body tag. In a preferred embodiment, the fusion protein comprises at least one cleavable peptide linker separating the inclusion body tag from the peptide of interest. In another preferred embodiment, the cleavable peptide linker comprises at least one acid cleavable aspartic acid—proline moiety.

The invention is useful for the expression and recovery of any bioactive peptides and proteins that are recombinantly expressed. Such proteins typically have high value in any number of applications including, but not limited to medical, biomedical, diagnostic, personal care, and affinity applications where the peptides of interest are used as linkers to various surfaces.

Applicants specifically incorporate the entire contents of all cited references in this disclosure. Further, when an amount, concentration, or other value or parameter is given either as a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The following definitions are used herein and should be referred to for interpretation of the claims and the specification. Unless otherwise noted, all U.S. patents and U.S. patent applications referenced herein are incorporated by reference in their entirety.

As used herein, the term "comprising" means the presence of the stated features, integers, steps, or components as referred to in the claims, but that it does not preclude the presence or addition of one or more other features, integers, steps, components or groups thereof.

The term "invention" or "present invention" as used herein is a non-limiting term and is not intended to refer to any single embodiment of the particular invention but encompasses all possible embodiments as described in the specification and the claims.

"Open reading frame" is abbreviated ORF.

"Polymerase chain reaction" is abbreviated PCR.

As used herein, the term "isolated nucleic acid molecule" is a polymer of RNA or DNA that is single- or double-stranded, optionally containing synthetic, non-natural or altered nucleotide bases. An isolated nucleic acid molecule in the form of a polymer of DNA may be comprised of one or more segments of cDNA, genomic DNA or synthetic DNA.

As used herein, the term "hair" as used herein refers to human hair, eyebrows, and eyelashes.

As used herein, the term "skin" as used herein refers to human skin, or substitutes for human skin, such as pig skin, Vitro-Skin® and EpiDerm™. Skin, as used herein, will refer to a body surface generally comprising a layer of epithelial cells and may additionally comprise a layer of endothelial cells.

As used herein, the term "nails" as used herein refers to human fingernails and toenails.

As used herein, the term "pigment" refers to an insoluble, organic or inorganic colorant.

As used herein, "HBP" means hair-binding peptide. Examples of hair binding peptides have been reported (U.S. patent application Ser. No. 11/074,473 to Huang et al.; WO 0179479; U.S. Patent Application Publication No. 2002/0098524 to Murray et al.; Janssen et al., U.S. Patent Application Publication No. 2003/0152976 to Janssen et al.; WO 04048399; U.S. Provisional Patent Application No. 60/721, 329; and U.S. Provisional Patent Application No. 60/790, 149).

As used herein, "SBP" means skin-binding peptide. Examples of skin binding peptides have also been reported (U.S. patent application Ser. No. 11/069,858 to Buseman-Williams; Rothe et. al., WO 2004/000257; and U.S. Provisional Patent Application No. 60/790,149).

As used herein, "NBP" means nail-binding peptide. Examples of nail binding peptides have been reported (U.S. Provisional Patent Application No. 60/790,149).

As used herein, an "antimicrobial peptide" is a peptide having the ability to kill microbial cell populations (U.S. Provisional Patent Application No. 60/790,149).

As used herein, the term "inclusion body tag" will be abbreviated "IBT" and will refer a polypeptide that facilitates formation of inclusion bodies when fused to a peptide of interest. The peptide of interest is typically soluble within the host cell and/or host cell lysate when not fused to an inclusion body tag. Fusion of the peptide of interest to the inclusion body tag produces a fusion protein that agglomerates into intracellular bodies (inclusion bodies) within the host cell. In one embodiment, the fusion protein comprises at least one portion comprising an inclusion body tag and at least one portion comprising the polypeptide of interest. In one embodiment, the protein/polypeptides of interest are separated from the inclusion body tags using cleavable peptide linker elements. As used herein, "cleavable linker elements", "peptide linkers", and "cleavable peptide linkers" will be used interchangeably and refer to cleavable peptide segments typically found between inclusion body tags and the peptide of interest. After the inclusion bodies are separated and/or partially-purified or purified from the cell lysate, the cleavable linker elements can be cleaved chemically and/or enzymatically to separate the inclusion body tag from the peptide of interest. The fusion peptide may also include a plurality of regions encoding one or more peptides of interest separated by one or more cleavable peptide linkers. The peptide of interest can then be isolated from the inclusion body tag, if necessary. In one embodiment, the inclusion body tag(s) and the peptide of interest exhibit different solubilities in a defined medium (typically an aqueous medium), facilitating separation of the inclusion body tag from the polypeptide of interest. In a preferred embodiment, the inclusion body tag is insoluble in an aqueous solution while the protein/polypeptide of interest is appreciably soluble in an aqueous solution. The pH, temperature, and/or ionic strength of the aqueous solution can be adjusted to facilitate recovery of the peptide of interest. In a preferred embodiment, the differential solubility between the inclusion body tag and the peptide of interest occurs in an aqueous solution having a pH of 5 to 10 and a temperature range of 15 to 50° C. The cleavable peptide linker may be from 1 to about 50 amino acids, preferably from 1 to about 20 amino acids in length. An example of an enzymatically cleavable peptide linker is provided by SEQ ID NO: 332 (Caspase-3 cleavage sequence). In a preferred embodiment, the cleavable linker is an acid cleavable aspartic acid—proline dipeptide (D-P) moiety (see INK101DP; SEQ ID NO: 18). The cleavable peptide linkers may be incorporated into the fusion proteins using any number of techniques well known in the art.

As used herein, the term "dispersant" as used herein refers to a substance that stabilizes the formation of a colloidal solution of solid pigment particles in a liquid medium. As used herein, the term "triblock dispersant" to a pigment dispersant that consists of three different units or blocks, each serving a specific function. In the present examples, a synthetic peptide encoding a peptide-based triblock dispersant was used as the "peptide of interest" to evaluate the performance of the present inclusion body tags (U.S. Ser. No. 10/935,254).

As used herein, the term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). In a further embodiment, the definition of "operably linked" may also be extended to describe the products of chimeric genes, such as fusion proteins. As such, "operably linked" will also refer to the linking of an inclusion body tag to a peptide of interest to be produced and recovered. The inclusion body tag is "operably linked" to the peptide of interest if upon expression the fusion protein is insoluble and accumulates it inclusion bodies in the expressing host cell. In a preferred embodiment, the fusion peptide will include at least on cleavable peptide linker useful in separating the inclusion body tag from the peptide of interest. In a preferred embodiment, the cleavable linker is an acid cleavable aspartic acid—proline dipeptide (D-P) moiety (see INK101DP; SEQ ID NO: 18). The cleavable peptide linkers may be incorporated into the fusion proteins using any number of techniques well known in the art.

As used herein, the terms "fusion protein", "fusion peptide", "chimeric protein", and "chimeric peptide" will be used interchangeably and will refer to a polymer of amino acids (peptide, oligopeptide, polypeptide, or protein) comprising at least two portions, each portion comprising a distinct function. At least one first portion of the fusion peptide comprises at least one of the present inclusion body tags. At least one second portion of the fusion peptide comprises at least one peptide of interest. In a preferred embodiment, the fusion protein additionally includes at least one cleavable peptide linker that facilitates cleavage (chemical and/or enzymatic) and separation of the inclusion body tag(s) and the peptide(s) of interest.

Means to prepare the present peptides (inclusion body tags, cleavable peptide linkers, peptides of interest, and fusion peptides) are well known in the art and in preferred embodiments the entire peptide reagent may be prepared using the recombinant DNA and molecular cloning techniques.

As used herein, the terms "polypeptide" and "peptide" will be used interchangeably to refer to a polymer of two or more amino acids joined together by a peptide bond, wherein the peptide is of unspecified length, thus, peptides, oligopeptides, polypeptides, and proteins are included within the present definition. In one aspect, this term also includes post expression modifications of the polypeptide, for example, glycosylations, acetylations, phosphorylations and the like. Included within the definition are, for example, peptides containing one or more analogues of an amino acid or labeled amino acids and peptidomimetics.

As used herein, the terms "protein of interest", "polypeptide of interest", "peptide of interest", "targeted protein", "targeted polypeptide", "targeted peptide", "expressible protein", and "expressible polypeptide" will be used interchangeably and refer to a protein, polypeptide, or peptide that is bioactive and may be expressed by the genetic machinery of a host cell.

As used herein, the term "bioactive" or "peptide of interest activity" refers to the activity or characteristic associated with the peptide and/or protein of interest. The bioactive peptides may be used in a variety of applications including, but not limited to curative agents for diseases (e.g., insulin, interferon, interleukins, anti-angiogenic peptides (U.S. Pat. No. 6,815,426), and polypeptides that bind to defined cellular targets such as receptors, channels, lipids, cytosolic proteins, and membrane proteins, to name a few), peptides having antimicrobial activity, peptides having an affinity for a particular material (e.g., hair binding polypeptides, skin binding polypeptides, nail binding polypeptides, cellulose binding polypeptides, polymer binding polypeptides, clay binding polypeptides, silicon binding polypeptides, carbon nanotube binding polypeptides, and peptides that have an affinity for particular animal or plant tissues) for targeted delivery of benefit agents.

As used herein, the "benefit agent" refers to a molecule that imparts a desired functionality to the complex for a defined application. The benefit agent may be peptide of interest itself or may be one or more molecules bound to (covalently or non-covalently), or associated with, the peptide of interest wherein the binding affinity of the targeted polypeptide is used to selectively target the benefit agent to the targeted material. In another embodiment, the targeted polypeptide comprises at least one region having an affinity for at least one target material (e.g., biological molecules, polymers, hair, skin, nail, other peptides, etc.) and at least one region having an affinity for the benefit agent (e.g., pharmaceutical agents, pigments, conditioners, dyes, fragrances, etc.). In another embodiment, the peptide of interest comprises a plurality of regions having an affinity for the target material and a plurality of regions having an affinity for the benefit agent. In yet another embodiment, the peptide of interest comprises at least one region having an affinity for a targeted material and a plurality of regions having an affinity for a variety of benefit agents wherein the benefit agents may be the same of different. Examples of benefits agents may include, but are not limited to conditioners for personal care products, pigments, dye, fragrances, pharmaceutical agents (e.g., targeted delivery of cancer treatment agents), diagnostic/labeling agents, ultraviolet light blocking agents (i.e., active agents in sunscreen protectants), and antimicrobial agents (e.g., antimicrobial peptides), to name a few.

As used herein, an "inclusion body" is an intracellular amorphous deposit comprising aggregated protein found in the cytoplasm of a cell. Peptides of interest that are typically soluble with the host cell and/or cell lysates can be fused to one or more of the present inclusion body tags to facilitate formation of an insoluble fusion protein. In an alternative embodiment, the peptide of interest may be partially insoluble in the host cell, but produced at relatively lows levels where significant inclusion body formation does not occur. As such, the formation of inclusion bodies will increase protein. In a further embodiment, fusion of the peptide of interest to one or more inclusion body tags (IBTs) increases the amount of protein produced in the host cell. Formation of the inclusion body facilitates simple and efficient purification of the fusion peptide from the cell lysate using techniques well known in the art such as centrifugation and filtration. The fusion protein typically includes one or more cleavable peptide linkers used to separate the protein/polypeptide of interest from the inclusion body tag(s). The cleavable peptide linker is designed so that the inclusion body tag(s) and the protein/polypeptide(s) of interest can be easily separated by cleaving the linker element. The peptide linker can be cleaved chemically (e.g., acid hydrolysis) or enzymatically (i.e., use of a protease/peptidase that preferentially recognizes an amino acid cleavage site and/or sequence within the cleavable peptide linker).

"Codon degeneracy" refers to the nature in the genetic code permitting variation of the nucleotide sequence without affecting the amino acid sequence of an encoded polypeptide. Accordingly, the instant invention relates to any nucleic acid fragment that encodes the present amino acid sequences. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

As used herein, the term "solubility" refers to the amount of a substance that can be dissolved in a unit volume of a liquid under specified conditions. In the present application, the term "solubility" is used to describe the ability of a peptide (inclusion body tag, peptide of interest, or fusion peptides) to be resuspended in a volume of solvent, such as a biological buffer. In one embodiment, the peptides targeted for production ("peptides of interest") are normally soluble in the cell and/or cell lysate under normal physiological conditions. Fusion of one or more inclusion body tags (IBTs) to the target peptide results in the formation of a fusion peptide that is insoluble under normal physiological conditions, resulting in the formation of inclusion bodies. In one embodiment, the peptide of interest is insoluble in an aqueous matrix having a pH range of 5-12, preferably 6-10; and a temperature range of 5° C. to 50° C., preferably 10° C. to 40° C. Fusion of the peptide of interest to at least one of the present inclusion body tags results in the formation of an insoluble fusion protein that agglomerates into at least one inclusion body under normal physiological conditions.

The term "amino acid" refers to the basic chemical structural unit of a protein or polypeptide. The following abbreviations are used herein to identify specific amino acids:

| Amino Acid | Three-Letter Abbreviation | One-Letter Abbreviation |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Miscellaneous (or as defined by the present formulas) | Xaa | X |

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences "Chimeric gene" refers to any gene that is not a native gene, comprising regulatory and coding sequences (including coding regions engineered to encode fusion peptides) that are not found together in nature. Accordingly, a chimeric gene may comprise regulatory sequences and coding sequences that are derived from different sources, or regulatory sequences and coding sequences derived from the same source, but arranged in a manner different than that found in nature. A "foreign" gene refers to a gene not normally found in the host organism, but that is introduced into the host organism by gene transfer. Foreign genes can comprise native genes inserted into a non-native organism, or chimeric genes.

As used herein, the term "coding sequence" refers to a DNA sequence that encodes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, enhancers, ribosomal binding sites, translation leader sequences, introns, polyadenylation recognition sequences, RNA processing site, effector binding sites, and stem-loop structures. One of skill in the art recognizes that selection of suitable regulatory sequences will depend upon host cell and/or expression system used.

As used herein, the term "genetic construct" refers to a series of contiguous nucleic acids useful for modulating the genotype or phenotype of an organism. Non-limiting examples of genetic constructs include but are not limited to a nucleic acid molecule, and open reading frame, a gene, a plasmid and the like.

As used herein, the term "expression ranking" means the relative yield of insoluble fusion protein estimated visually and scored on a relative scale of 0 (no insoluble fusion peptide) to 3 (highest yield of insoluble fusion peptide). As described in the present examples, the relative yield of insoluble fusion protein was estimated visually from stained polyacrylamide gels.

As used herein, the term "transformation" refers to the transfer of a nucleic acid fragment into the genome of a host organism, resulting in genetically stable inheritance. As used herein, the host cell's genome is comprised of chromosomal and extrachromosomal (e.g., plasmid) genes. Host organisms containing the transformed nucleic acid fragments are referred to as "transgenic" or "recombinant" or "transformed" organisms. As used herein, the term "host cell" refers to cell which has been transformed or transfected, or is capable of transformation or transfection by an exogenous polynucleotide sequence.

As used herein, the terms "plasmid", "vector" and "cassette" refer to an extrachromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitates transformation of a particular host cell. "Expression cassette" refers to a specific vector containing a foreign gene and having elements in addition to the foreign gene that allow for enhanced expression of that gene in a foreign host.

Standard recombinant DNA and molecular cloning techniques used herein are well known in the art and are described by Sambrook, J., Fritsch, E. F. and Maniatis, T., *Molecular Cloning: A Laboratory Manual*, Third Edition, Cold Spring Harbor Laboratory Press, Cold Spring Harbor, N.Y. (2001) (hereinafter "Maniatis"); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et al., *Current Protocols in Molecular Biology*, published by Greene Publishing Assoc. and Wiley-Interscience (1987).

Inclusion Body Tags

Amyloid-type proteins, typically rich in the amino acids glutamine, asparagine, and proline are naturally-occurring proteins known to readily precipitate under physiological conditions. A search of the publicly available databases for glutamine rich proteins was conducted and a hypothetical protein from *Caenorhabditis elegans* was identified (GenBank® accession number MK68556; Basham, V. M., Science, 282 (5389), 2012-2018 (1998); SEQ ID NOs: 138 and 139). This protein was selected as the starting material for preparation of the present inclusion body tags. Short regions (~10 amino acids) of the *C. elegans* protein were evaluated for their ability to act as a suitable inclusion body tag. From this protein, inclusion body tag #24 (IBT-24; SEQ ID NO: 70) was prepared.

A series of IBT-24 analogues were prepared and evaluated. Several approaches were taken including varying copy number (e.g., IBT-3), altering the charge of the tag (e.g., IBT-26 or IBT-35), and adding different amino acid units (e.g., IBT-95). The present inclusion body tags are provided in Table 3.

One set of analogues examined the effects of exchanging the positively charged arginine (R) residues (of which there are eight in IBT-3) for negatively charged glutamic acid (E) residues. Increasing the number or R→E substitutions decreased the isoelectric point of the tag. A second set of IBT-3 analogues added varying lengths of negatively charged glutamic acid to the C-terminus of IBT-3. This modification added a significant amount of localized negative charge to the fusion tag, neutralizing the positive charge supplied by the arginine residues. Each of the present fusion tags was fused to a standard peptide of interest derived from TBP101 (SEQ ID NO: 2). The peptide of interest (when not linked to an inclusion body tag) is soluble under physiological conditions. Each fusion peptide was recombinantly expressed in an appropriate host cell and evaluated for insoluble fusion peptide formation.

Several inclusion body tags were identified that were effective in creating insoluble fusion peptides. The amino acid sequence of the present inclusion body tags can be defined by Formula 1:

[Ser-(Xaa$_1$)-(Xaa$_2$)-[Asp]$_a$-(Xaa$_3$)-(Xaa$_4$)-(Xaa$_5$)-[Asp-Pro]$_b$-Leu-Gln-Gln-(Xaa$_6$)-Gln-[Asp-Pro]$_c$]$_n$-[R$_1$]$_d$     Formula 1.

wherein a=0 or 1, b=0 or 1, c=0 or 1, d=0 or 1, and n=1-20 and wherein (Xaa$_1$)=Arg or Glu;

(Xaa$_2$)=Arg or Glu;

(Xaa$_3$)=Pro or Gln;

(Xaa$_4$)=Arg, Glu, or Asp (Xaa$_5$)=Gln or Pro;

(Xaa$_6$)=Arg or Glu;

and wherein when d=1 then n=1 or 2 and R$_1$ is selected from the group consisting of
  a) His-His-Gln-Gln-Gln-Gln-Glu;
  b) Ser-Leu-Gly-Tyr-Gly-Gly-Leu-Tyr-Gly-Tyr;
  c) Glu-Glu;
  d) Glu-Glu-Glu;
  e) Glu-Glu-Glu-Glu; and
  f) Glu-Glu-Glu-Glu-Glu.

In one embodiment, n=1 to 20, preferably 1 to 10, more preferably 1 to 5, and most preferably 1 to 2.

In another embodiment, the present inclusion body tags comprise Formula 1 with the proviso that the inclusion body tag is not equal to SEQ ID NO: 139.

The present fusion tags were developed from IBT-24 (SEQ ID NO: 70). As such, and in another embodiment, the present inclusion body tags typically comprise a core amino sequence defined by Formula 2 (SEQ ID NO: 137):

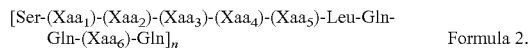

Formula 2.

wherein the amino acids for $Xaa_1$, $Xaa_2$, $Xaa_3$, $Xaa_4$, $Xaa_5$, $Xaa_6$, and value range of "n" are as defined above. In yet another embodiment, the present inclusion body tags comprise Formula 2 wherein the inclusion body tag does not include the entire amino acid sequence of the *C. elegans* hypothetical protein (SEQ ID NO: 139).

In another embodiment, the core amino acid sequence may include at least one Asp residue and/or an Asp-Pro residue pair inserted internally or added to the amino or carboxyl terminal of the core amino acid sequence (SEQ ID NO: 137).

The present inclusion body tags are less than 200 amino acids in length, preferably less than 125 amino acid residues in length, more preferably less than 75 amino acid residues, even more preferably less than 50 amino acid residues, and yet even more preferably less than 30 amino acid residues in length, and most preferably about 15 amino acid residues in length.

In one embodiment, the present inclusion body tags are selected from the group consisting of SEQ ID NOs: 67, 68, 69, 70, 71, 72, 73, 74, 75, 76, 77, 81, 82, 83, 84, 87, 88, 89, 90, and 137. Preferred for use herein are inclusion body tags comprising the core sequence as defined by SEQ ID NO: 137, with the proviso that the inclusion body tag sequence is not identical to SEQ ID NO: 139.

Examples of inclusion bodies defined by Formula 1 were evaluated in terms of expression ranking as shown in Table 4. An amino acid sequence alignment of the present inclusion body tag sequences is provided in Table 5.

Expressible Peptides of Interest

The peptide of interest ("expressible peptide") targeted for production using the present method is one that is appreciably soluble in the host cell and/or host cell liquid lysate under normal physiological conditions. In a preferred aspect, the peptides of interest are generally short (<50 amino acids in length) and difficult to produce in sufficient amounts due to proteolytic degradation. Fusion of the peptide of interest to at least one of the present inclusion body forming tags creates a fusion peptide that is insoluble in the host cell and/or host cell lysate under normal physiological conditions. Production of the peptide of interest is typically increased when expressed and accumulated in the form of an insoluble inclusion body as the peptide is generally more protected from proteolytic degradation. Furthermore, the insoluble fusion protein can be easily separated from the host cell lysate using centrifugation or filtration.

In general, the present inclusion body tags can be used in a process to produce any peptide of interest that is (1) typically soluble in the cell and/or cell lysate under typical physiological conditions and/or (2) those that can be produced at significantly higher levels when expressed in the form of an inclusion body. In a preferred embodiment, the peptide of interest is appreciably soluble in the host cell and/or corresponding cell lysate under normal physiological and/or process conditions.

The length of the peptide of interest may vary as long as (1) the peptide is appreciably soluble in the host cell and/or cell lysate, and/or (2) the amount of the targeted peptide produced is significantly increased when expressed in the form of an insoluble fusion peptide/inclusion body (i.e. expression in the form of a fusion protein protect the peptide of interest from proteolytic degradation). Typically the peptide of interest is less than 200 amino acids in length, preferably less than 100 amino acids in length, more preferably less than 75 amino acids in length, even more preferably less than 50 amino acids in length, and most preferably less than 25 amino acids in length.

The function of the peptide of interest is not limited by the present method and may include, but is not limited to bioactive molecules such as curative agents for diseases (e.g., insulin, interferon, interleukins, peptide hormones, anti-angiogenic peptides, and peptides that bind to and affect defined cellular targets such as receptors, channels, lipids, cytosolic proteins, and membrane proteins; see U.S. Pat. No. 6,696,089,), peptides having an affinity for a particular material (e.g., biological tissues, biological molecules, hair binding peptides (U.S. patent application Ser. No. 11/074,473; WO 0179479; U.S. Patent Application Publication No. 2002/0098524; U.S. Patent Application Publication No. 2003/0152976; WO 04048399; U.S. Provisional Patent Application No. 60/721,329; and U.S. Provisional Patent Application No. 60/790,149)., skin binding peptides (U.S. patent application Ser. No. 11/069,858; WO 2004/000257; and U.S. Provisional Patent Application No. 60/790,149), nail binding peptides (U.S. Provisional Patent Application No. 60/790,149), cellulose binding peptides, polymer binding peptides (U.S. Provision Patent Application Nos. 60/750,598, 60/750,599, 60/750,726, 60/750,748, and 60/750,850), clay binding peptides, silicon binding peptides, and carbon nanotube binding peptides) for targeted delivery of at least one benefit agent (see U.S. patent application Ser. No. 10/935,642; U.S. patent application Ser. No. 11/074,473; and U.S. Provisional Patent Application No. 60/790,149).

In a preferred aspect, the peptide of interest is selected from the group of hair binding peptides, skin binding peptides, nail binding peptides, antimicrobial peptides, pigment binding peptides and polymer binding peptides. In another preferred aspect, the peptide of interest is selected from the group consisting of a hair binding peptide comprising an amino acid sequence selected from the group consisting of SEQ ID NOs 148 to 240, a skin binding peptide comprising an amino acid sequence selected from the group consisting of SEQ ID NOs: 140 to 147, a nail binding peptide comprising an amino acid sequence selected from the group consisting of SEQ ID NOs: 241 and 242 and a pigment binding peptide selected from the group consisting of SEQ ID NO: 272-297.

As used herein, the "benefit agent" refers to a molecule that imparts a desired functionality to a target material (e.g., hair, skin, etc.) for a defined application (U.S. patent application Ser. No. 10/935,642; U.S. patent application Ser. No. 11/074, 473; and U.S. Patent Application 60/790,149 for a list of typical benefit agents such as conditioners, pigments/colorants, fragrances, etc.). The benefit agent may be peptide of interest itself or may be one or more molecules bound to (covalently or non-covalently), or associated with, the peptide of interest wherein the binding affinity of the peptide of interest is used to selectively target the benefit agent to the targeted material. In another embodiment, the peptide of interest comprises at least one region having an affinity for at least one target material (e.g., biological molecules, polymers, hair, skin, nail, other peptides, etc.) and at least one region having an affinity for the benefit agent (e.g., pharmaceutical agents, antimicrobial agents, pigments, conditioners, dyes, fragrances, etc.). In another embodiment, the peptide of interest comprises a plurality of regions having an affinity for the target material and a plurality of regions having an affinity for one or more benefit agents. In yet another embodiment, the peptide of interest comprises at least one region having an affinity for a targeted material and a plurality of regions having an affinity for a variety of benefit agents wherein the benefit agents may be the same of different. Examples of benefits agents may include, but are not limited to conditioners for personal care products, pigments, dye, fragrances, pharmaceutical agents (e.g., targeted delivery of cancer treatment agents), diagnostic/labeling agents, ultraviolet light blocking agents (i.e., active agents in sunscreen protectants), and antimicrobial agents (e.g., antimicrobial peptides), to name a few.

Cleavable Peptide Linkers

The use of cleavable peptide linkers is well known in the art. Fusion peptides comprising the present inclusion body tags will typically include at least one cleavable sequence separating the inclusion body tag from the polypeptide of interest. The cleavable sequence facilitates separation of the inclusion body tag(s) from the peptide(s) of interest. In one embodiment, the cleavable sequence may be provided by a portion of the inclusion body tag and/or the peptide of interest (e.g., inclusion of a acid cleavable aspartic acid—proline moiety). In a preferred embodiment, the cleavable sequence is provided by including (in the fusion peptide) at least one cleavable peptide linker between the inclusion body tag and the peptide of interest.

Means to cleave the peptide linkers are well known in the art and may include chemical hydrolysis, enzymatic cleavage agents, and combinations thereof. In one embodiment, one or more chemically cleavable peptide linkers are included in the fusion construct to facilitate recovery of the peptide of interest from the inclusion body fusion protein. Examples of chemical cleavage reagents include cyanogen bromide (cleaves methionine residues), N-chloro succinimide, iodobenzoic acid or BNPS-skatole [2-(2-nitrophenylsulfenyl)-3-methylindole] (cleaves tryptophan residues), dilute acids (cleaves at aspartyl-prolyl bonds), and hydroxylamine (cleaves at asparagine-glycine bonds at pH 9.0); see Gavit, P. and Better, M., *J. Biotechnol.*, 79:127-136 (2000); Szoka et al., DNA, 5(1):11-20 (1986); and Walker, J. M., *The Proteomics Protocols Handbook*, 2005, Humana Press, Totowa, N.J.)). In a preferred embodiment, one or more aspartic acid—proline acid cleavable recognition sites (i.e., a cleavable peptide linker comprising one or more D-P dipeptide moieties) are included in the fusion protein construct to facilitate separation of the inclusion body tag(s) form the peptide of interest. In another embodiment, the fusion peptide may include multiple regions encoding peptides of interest separated by one or more cleavable peptide linkers.

In another embodiment, one or more enzymatic cleavage sequences are included in the fusion protein construct to facilitate recovery of the peptide of interest. Proteolytic enzymes and their respective cleavage site specificities are well known in the art. In a preferred embodiment, the proteolytic enzyme is selected to specifically cleave only the peptide linker separating the inclusion body tag and the peptide of interest. Examples of enzymes useful for cleaving the peptide linker include, but are not limited to Arg-C proteinase, Asp-N endopeptidase, chymotrypsin, clostripain, enterokinase, Factor Xa, glutamyl endopeptidase, Granzyme B, *Achromobacter* proteinase I, pepsin, proline endopeptidase, proteinase K, Staphylococcal peptidase I, thermolysin, thrombin, trypsin, and members of the Caspase family of proteolytic enzymes (e.g. Caspases 1-10) (Walker, J. M., supra). An example of a cleavage site sequence is provided by SEQ ID NO: 332 (Caspase-3 cleavage site; Thornberry et al. *J. Biol. Chem.*, 272:17907-17911 (1997) and Tyas et al., EMBO Reports, 1 (3):266-270 (2000)). Typically, the cleavage step occurs after the insoluble inclusion bodies and/or insoluble fusion peptides are isolated from the cell lysate. The cells can be lysed using any number of means well known in the art (e.g. mechanical and/or chemical lysis). Methods to isolate the insoluble inclusion bodies/fusion peptides from the cell lysate are well known in the art (e.g., centrifugation, filtration, and combinations thereof). Once recovered from the cell lysate, the insoluble inclusion bodies and/or fusion peptides can be treated with a cleavage agent (chemical or enzymatic) to cleavage the inclusion body tag from the peptide of interest. In one embodiment, the fusion protein and/or inclusion body is diluted and/or dissolved in a suitable solvent prior to treatment with the cleavage agent. In a further embodiment, the cleavage step may be omitted if the inclusion body tag does not interfere with the activity of the peptide of interest. After the cleavage step, and in a preferred embodiment, the peptide of interest can be separated and/or isolated from the fusion protein and the inclusion body tags based on a differential solubility of the components. Parameters such as pH, salt concentration, and temperature may be adjusted to facilitate separation of the inclusion body tag from the peptide of interest. In one embodiment, the peptide of interest is soluble while the inclusion body tag and/or fusion protein is insoluble in the defined process matrix (typically an aqueous matrix). In another embodiment, the peptide of interest is insoluble while the inclusion body tag is soluble in the defined process matrix.

In another embodiment, the peptide of interest may be further purified using any number of well known purification techniques in the art such as ion exchange, gel purification techniques, and column chromatography (see U.S. Pat. No. 5,648,244), to name a few.

Fusion Peptides

The present inclusion body tags are used to create chimeric polypeptides ("fusion peptides" or "fusion proteins") that are insoluble within the host cell, forming inclusion bodies. Synthesis and expression of expressible genetic constructs encoding the present fusion peptides is well known to one of skill in the art given the present inclusion body tags.

The present fusion peptides will include at least one of the present inclusion body tags (IBTs) operably linked to at least one peptide of interest. Typically, the fusion peptides will also include at least one cleavable peptide linker having a cleavage site between the inclusion body tag and the peptide of interest. In one embodiment, the inclusion body tag may include a cleavage site whereby inclusion of a separate cleavable peptide linker may not be necessary. In a preferred embodiment, the cleavage method is chosen to ensure that the peptide of interest is not adversely affected by the cleavage agent(s) employed. In a further embodiment, the peptide of interest may be modified to eliminate possible cleavage sites with the peptide so long as the desired activity of the peptide is not adversely affected.

One of skill in the art will recognize that the elements of the fusion protein can be structured in a variety of ways. Typically, the fusion protein will include at least one IBT, at least one peptide of interest (POI), and at least one cleavable linker (CL) located between the IBT and the POI. The inclusion body tag may be organized as a leader sequence or a terminator sequence relative to the position of the peptide of interest within the fusion peptide. In another embodiment, a plurality of IBTs, POIs, and CLs are used when engineering the fusion peptide. In a further embodiment, the fusion peptide may include a plurality of IBTs (as defined herein), POIs, and CLs that are the same or different.

The fusion peptide should be insoluble in an aqueous matrix at a temperature of 10° C. to 50° C., preferably 10° C. to 40° C. The aqueous matrix typically comprises a pH range of 5 to 12, preferably 6 to 10, and most preferably 6 to 8. The temperature, pH, and/or ionic strength of the aqueous matrix can be adjusted to obtain the desired solubility characteristics of the fusion peptide/inclusion body.

Method to Make a Peptide of Interest Using Insoluble Fusion Peptides

The present inclusion body tags are used to make fusion peptides that form inclusion bodies within the production host. This method is particularly attractive for producing significant amounts of soluble peptide of interest that (1) are difficult to isolation from other soluble components of the cell lysate and/or (2) are difficult to product in significant amounts within the target production host.

In the present methods, a peptide of interest is fused to at least one of the present inclusion body tags, forming an insoluble fusion protein. Expression of the genetic construct encoding the fusion protein produces an insoluble form of the peptide of interest that accumulates in the form of inclusion bodies within the host cell. The host cell is grown for a period of time sufficient for the insoluble fusion peptide to accumulate within the cell.

The host cell is subsequently lysed using any number of techniques well known in the art. The insoluble fusion peptide/inclusion bodies are then separated from the soluble components of the cell lysate using a simple and economical technique such as centrifugation and/or membrane filtration. The insoluble fusion peptide/inclusion body can then be further processed in order to isolate the peptide of interest. Typically, this will include re-suspension of the fusion peptide/inclusion body in a liquid matrix suitable for cleaving the fusion peptide, separating the inclusion body tag from the peptide of interest. The fusion protein is typically designed to include a cleavable peptide linker separating the inclusion body tag from the peptide of interest. The cleavage step can be conducted using any number of techniques well known in the art (chemical cleavage, enzymatic cleavage, and combinations thereof). The peptide of interest can then be separated from the inclusion body tag(s) and/or fusion peptides using any number of techniques well known in the art (centrifugation, filtration, precipitation, column chromatography, etc.). Preferably, the peptide of interest (once cleaved from fusion peptide) has a solubility that is significantly different than that of the inclusion body tag and/or remaining fusion peptide.

Transformation and Expression

Once the inclusion body tag has been identified and paired with the appropriate peptide of interest, construction of cassettes and vectors that may be transformed in to an appropriate expression host is common and well known in the art. Typically, the vector or cassette contains sequences directing transcription and translation of the relevant chimeric gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Transcription initiation control regions or promoters, which are useful to drive expression of the genetic constructs encoding the fusion peptides in the desired host cell, are numerous and familiar to those skilled in the art. Virtually any promoter capable of driving these constructs is suitable for the present invention including but not limited to CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, ara (pBAD), tet, trp, $IP_L$, $IP_R$, T7, tac, and trc (useful for expression in *Escherichia coli*) as well as the amy, apr, npr promoters and various phage promoters useful for expression in *Bacillus*.

Termination control regions may also be derived from various genes native to the preferred hosts. Optionally, a termination site may be unnecessary, however, it is most preferred if included.

Preferred host cells for expression of the present fusion peptides are microbial hosts that can be found broadly within the fungal or bacterial families and which grow over a wide range of temperature, pH values, and solvent tolerances. For example, it is contemplated that any of bacteria, yeast, and filamentous fungi will be suitable hosts for expression of the present nucleic acid molecules encoding the fusion peptides. Because of transcription, translation, and the protein biosynthetic apparatus is the same irrespective of the cellular feedstock, genes are expressed irrespective of the carbon feedstock used to generate the cellular biomass. Large-scale microbial growth and functional gene expression may utilize a wide range of simple or complex carbohydrates, organic acids and alcohols (i.e. methanol), saturated hydrocarbons such as methane or carbon dioxide in the case of photosynthetic or chemoautotrophic hosts. However, the functional genes may be regulated, repressed or depressed by specific growth conditions, which may include the form and amount of nitrogen, phosphorous, sulfur, oxygen, carbon or any trace micronutrient including small inorganic ions. In addition, the regulation of functional genes may be achieved by the presence or absence of specific regulatory molecules that are added to the culture and are not typically considered nutrient or energy sources. Growth rate may also be an important regulatory factor in gene expression. Examples of host strains include, but are not limited to fungal or yeast species such as *Aspergillus, Trichoderma, Saccharomyces, Pichia; Candida, Hansenula*, or bacterial species such as *Salmonella, Bacillus, Acinetobacter, Zymomonas, Agrobacterium, Erythrobacter, Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella*, and *Myxococcus*. Preferred bacterial host strains include *Escherichia* and *Bacillus*. In a highly preferred aspect, the host strain is *Escherichia coli*.

Fermentation Media

Fermentation media in the present invention must contain suitable carbon substrates. Suitable substrates may include but are not limited to monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Additionally the carbon substrate may also be one-carbon substrates such as carbon dioxide, or methanol for which metabolic conversion into key biochemical intermediates has been demonstrated. In addition to one and two carbon substrates methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., *Microb. Growth C1 Compd.*, [Int. Symp.], 7th (1993), 415-32. Editor(s): Murrell, J. Collin; Kelly, Don P. Publisher: Intercept, Andover, UK). Similarly, various species of *Candida* will metabolize alanine or oleic acid (Sulter et al., *Arch. Microbiol.* 153:485-489 (1990)). Hence it is contemplated that the source of carbon utilized in the present invention may encompass a wide variety of carbon containing substrates and will only be limited by the choice of organism.

Although it is contemplated that all of the above mentioned carbon substrates and mixtures thereof are suitable in the present invention, preferred carbon substrates are glucose, fructose, and sucrose.

In addition to an appropriate carbon source, fermentation media must contain suitable minerals, salts, cofactors, buffers and other components, known to those skilled in the art, suitable for the growth of the cultures and promotion of the expression of the present fusion peptides.

Culture Conditions

Suitable culture conditions can be selected dependent upon the chosen production host. Typically, cells are grown at a temperature in the range of about 25° C. to about 40° C. in an appropriate medium. Suitable growth media in the present invention are common commercially prepared media such as Luria Bertani (LB) broth, Sabouraud Dextrose (SD) broth or Yeast medium (YM) broth. Other defined or synthetic growth media may also be used and the appropriate medium for growth of the particular microorganism will be known by one skilled in the art of microbiology or fermentation science. The use of agents known to modulate catabolite repression directly or indirectly, e.g., cyclic adenosine 2':3'-monophosphate, may also be incorporated into the fermentation medium.

Suitable pH ranges for the fermentation are typically between pH 5.0 to pH 9.0, where pH 6.0 to pH 8.0 is preferred.

Fermentations may be performed under aerobic or anaerobic conditions where aerobic conditions are generally preferred.

Industrial Batch and Continuous Fermentations

A classical batch fermentation is a closed system where the composition of the medium is set at the beginning of the fermentation and not subject to artificial alterations during the fermentation. Thus, at the beginning of the fermentation the medium is inoculated with the desired organism or organisms, and fermentation is permitted to occur without adding anything to the system. Typically, a "batch" fermentation is batch with respect to the addition of carbon source and attempts are often made at controlling factors such as pH and oxygen concentration. In batch systems the metabolite and biomass compositions of the system change constantly up to the time the fermentation is stopped. Within batch cultures cells moderate through a static lag phase to a high growth log phase and finally to a stationary phase where growth rate is diminished or halted. If untreated, cells in the stationary phase will eventually die. Cells in log phase generally are responsible for the bulk of production of end product or intermediate.

A variation on the standard batch system is the Fed-Batch system. Fed-Batch fermentation processes are also suitable in the present invention and comprise a typical batch system with the exception that the substrate is added in increments as the fermentation progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch fermentations are common and well known in the art and examples may be found in Thomas D. Brock in *Biotechnology: A Textbook of Industrial Microbiology*, Second Edition (1989) Sinauer Associates, Inc., Sunderland, Mass. (hereinafter "Brock"), or Deshpande, Mukund V., *Appl. Biochem. Biotechnol.*, 36:227, (1992).

Although the present invention is performed in batch mode it is contemplated that the method would be adaptable to continuous fermentation methods. Continuous fermentation is an open system where a defined fermentation medium is added continuously to a bioreactor and an equal amount of conditioned media is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to the medium being drawn off must be balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, supra.

It is contemplated that the present invention may be practiced using either batch, fed-batch or continuous processes and that any known mode of fermentation would be suitable.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations used is as follows: "min" means minute(s), "h" means hour(s), "μL" means microliter(s), "mL" means milliliter(s), "L" means liter(s), "nm" means nanometer(s), "mm" means millimeter(s), "cm" means centimeter(s), "μm" means micrometer(s), "mM" means millimolar, "M" means molar, "mmol" means millimole(s), "μmol" means micromole(s), "pmol" means picomole(s), "g" means gram(s), "μg" means microgram(s), "mg"

means milligram(s), "g" means the gravitation constant, "rpm" means revolutions per minute, "DTT" means dithiothreitol, and "cat#" means catalog number.

General Methods

Standard recombinant DNA and molecular cloning techniques used in the Examples are well known in the art and are described by Maniatis, (supra); Silhavy et al., (supra); and Ausubel et al., (supra).

Materials and methods suitable for the maintenance and growth of bacterial cultures are also well known in the art. Techniques suitable for use in the following Examples may be found in *Manual of Methods for General Bacteriology*, Phillipp Gerhardt, R. G. E. Murray, Ralph N. Costilow, Eugene W. Nester, Willis A. Wood, Noel R. Krieg and G. Briggs Phillips, eds., American Society for Microbiology, Washington, D.C., 1994, or in Brock (supra). All reagents, restriction enzymes and materials used for the growth and maintenance of bacterial cells were obtained from BD Diagnostic Systems (Sparks, Md.), Invitrogen (Carlsbad, Calif.), Life Technologies (Rockville, Md.), QIAGEN (Valencia, Calif.) or Sigma-Aldrich Chemical Company (St. Louis, Mo.), unless otherwise specified.

Example 1

Preparation of Plasmid pLX121 for Evaluating Inclusion Body Tag Performance

A genetic construct was prepared for evaluating the performance of the present inclusion body tags when fused to a soluble peptide of interest. The peptide of interest used in the present examples was prepared from a previously reported peptide-based triblock dispersant (U.S. Ser. No. 10/935,254).

Cloning of the TBP1 Gene

The TBP1 gene, encoding the TBP1 peptide, was selected for evaluation of the present inclusion body tags. The synthetic TBP1 peptide is peptide-based triblock dispersant comprising a carbon-black binding domain, a hydrophilic peptide linker, and a cellulose binding domain (see Example 15 of U.S. patent application Ser. No. 10/935,254, herein incorporated by reference).

The TBP1 gene (SEQ ID NO: 1) encoding the 68 amino acid peptide TBP101 (SEQ ID NO: 2) was assembled from synthetic oligonucleotides (Sigma-Genosys, Woodlands, Tex.; Table 1).

TABLE 1

Oligonucleotides Used to Prepare the TBP1

| Oligonucleotide Name | Nucleotide Sequence (5'-3') | SEQ ID NO: |
|---|---|---|
| TBP1 (+)1 | GGATCCATCGAAGGTCGTTTCCACGA AAACTGGCCGTCTGGTGGCGGTACCTC TACTTCCAAAGCTTCCACCACTACGAC TTCTAGCAAAACCACCACTACAT | 3 |
| TBP1 (+)2 | CCTCTAAGACTACCACGACTACCTCCA AAACCTCTACTACCTCTAGCTCCTCTA CGGGCGGTGGCACTCACAAGACCTCT ACTCAGCGTCTGCTGGCTGCATAA | 4 |
| TBP1 (-)1 | TTATGCAGCCAGCAGACGCTGAGTAG AGGTCTTGTGAGTGCCACCGCCCGTA GAGGAGCTAGAGGTAGT | 5 |

TABLE 1-continued

Oligonucleotides Used to Prepare the TBP1

| Oligonucleotide Name | Nucleotide Sequence (5'-3') | SEQ ID NO: |
|---|---|---|
| TBP1 (-)2 | AGAGGTTTTGGAGGTAGTCGTGGTAG TCTTAGAGGATGTAGTGGTGGTTTTG CTAGAAGTCGTAGTGGT | 6 |
| TBP1 (-)3 | GGAAGCTTTGGAAGTAGAGGTACCGC CACCAGACGGCCAGTTTTCGTGGAAA CGACCTTCGATGGATCC | 7 |

Each oligonucleotide was phosphorylated with ATP using T4 polynucleotide kinase. The resulting oligonucleotides were mixed, boiled for 5 min, and then cooled to room temperature slowly. Finally, the annealed oligonucleotides were ligated with T4 DNA ligase to give synthetic DNA fragment TBP1, given as SEQ ID NO: 1, which encodes the TBP101 peptide.

Construction of pINK101 Expression Plasmid:

Lambda phage site-specific recombination was used for preparation and expression of the present fusion proteins (Gateway™ System; Invitrogen, Carlsbad, Calif.). TBP1 was integrated into the Gateway™ system for protein over-expression. In the first step, 2 µL of the TBP1 ligation mixture was used in a 50-µL PCR reaction. Reactions were catalyzed by Pfu DNA polymerase (Stratagene, La Jolla, Calif.), following the standard PCR protocol. Primer 5'TBP1 (5'-CAC-CGGATCCATCGAAGGTCGT-3'; SEQ ID NO: 8) and 3'TBP1 (5'-TCATTATGCAGCCAGCAGCGC-3'; SEQ ID NO: 9) were used for amplification of the TBP1 fragment. Due to the design of these primers, an additional sequence of CACC and another stop codon TGA were added to the 5' and 3' ends of the amplified fragments.

The amplified TBP1 was directly cloned into pENTR™/D-TOPO® vector (SEQ ID NO: 10) using Invitrogen's pENTR™ directional TOPO® cloning kit (Invitrogen; Catalog K2400-20), resulting in the Gateway™ entry plasmid pENTR-TBP1. This entry plasmid was propagated in One Shots TOP10 *E. coli* cells (Invitrogen). The accuracy of the PCR amplification and cloning procedures were confirmed by DNA sequencing analysis. The entry plasmid was mixed with pDEST17 (Invitrogen, SEQ ID NO: 11). LR recombination reactions were catalyzed by LR Clonase™ (Invitrogen). The destination plasmid, pINK101 was constructed and propagated in the DH5α *E. coli* strain. The accuracy of the recombination reaction was determined by DNA sequencing. All reagents for LR recombination reactions (i.e., lambda phage site-specific recombination) were provided in Invitrogen's *E. coli* expression system with the Gateway™ Technology kit. The site-specific recombination process followed the manufacturer's instructions (Invitrogen).

The resulting plasmid, named pINK101, contains the coding regions for recombinant protein 6H-TBP1, named INK101 (SEQ ID NOs 12 and 13), which is an 11.6 kDa protein. The protein sequence includes a 6×His tag and a 24 amino acid linker that includes a Factor Xa protease recognition site before the sequence of the TBP101 peptide.

The amino acid coding region for the 6×His tag and the following linker comprising the Factor Xa protease recognition site were excised from pINK101 by digestion with the NdeI and BamHI restriction enzymes.

The TBP1 gene (SEQ ID NO: 1) encodes a polypeptide (SEQ ID NO: 2) having a ST linker flanked by Gly-Gly-Gly amino acids. The system was made more modular by further mutagenesis to change the upstream amino acid sequence from Gly-Gly-Gly to Ala-Gly-Gly (codon GGT changed to GCC) and the downstream Gly-Gly-Gly to Gly-Gly-Ala (codon GGT GGC changed to GGC GCC). These changes provided a NgoMl restriction site and a Kasl restriction site flanking the ST linker, thus facilitating replacement of any element in TBP1.

Further modifications were made to TBP101 including the addition of an acid cleavable site to facilitate the removal of any tag sequence encoded by the region between the NdeI and BamHI sites of the expression plasmid. The resulting plasmid was called pLX121 (also referred to as "pINKO11DP"; SEQ ID NO: 14). These modifications changed the amino acids E-G to D-P (acid cleavable aspartic acid—proline linkage) using the Stratagene QuikChange® II Site-Directed Mutagenesis Kit Cat# 200523 (La Jolla, Calif.) as per the manufacturer's protocol using the primers INK101+(5'-CCCCTTCACCGGATCCATCGATC-CACGTTTCCACGAAAACTGGCC-3'; SEQ ID 15) and INK101-(5'-GGCCAGTTTTCGTGGAAACGTGGATC-GATGGATCCGGTGAAGGGG-3'; SEQ ID NO 16). The sequences were confirmed by DNA sequence analysis. The coding region and the corresponding amino acid sequence of the modified protein, INK101DP, is provided as SEQ ID NOs 17 and 18, respectively. INK101 DP (also referred to herein as "TBP101 DP") was used to evaluate the present inclusion body tags.

INK101DP Peptide (SEQ ID NO: 18)

MSYYHHHHHHLESTSLYKKAGSAAAPFTGSIDPRFH
ENWPSAGGTSTSKASTTTTSSKTTTTSSKTTTTTSKT
STTSSSSTGGATHKTSTQRLLAA

The aspartic acid—proline acid cleavable linker is bolded. The DP moiety replaced the EG moiety found in the unmodified TBP101 peptide. The modified TBP101 peptide (i.e., peptide of interest) is underlined.

Example 2

Construction Inclusion Body Tag 3 (IBT-3)

The test system expression vector pLX121 has two unique restriction endonuclease sites (NdeI and BamHI) facilitating inclusion body fusion partner replacement in-frame with the INK101DP peptide. The amino tag of the INK101 DP peptide is also easily replaced by any peptide with BamHI and Ascl restriction sites, facilitating testing of any peptide-tag combination easily. The overall scheme to test fusion partner sequences was to design DNA oligonucleotides that when annealed generate the stick-ends required for directional cloning of the fusion partner in-frame with the test expression peptide.

An example of the methodology used to generate, test and score putative fusion partners follows. A nucleic acid molecule encoding an 11 amino acid sequence (SR-RPRQLQQRQ; SEQ ID NO: 70) from a glutamine rich, amyloid-like protein from *C. elegans* was initially tested as a dimer (Inclusion Body Tag 3 (IBT-3);

SRRPRQLQQRQSRRPRQLQQRQ; SEQ ID NO: 67). IBT-3: was assembled from two complementary synthetic *E. coli* codon biased oligonucleotides (Sigma-Genosys).

IBT3+oligo: 5'-TATGAGCCGTCGTCCGCGTCAGT-TGCAGCAGCGTCAGAGCCGTCGT CCGCGTCAGT-TGCAGCAGCGTCAGG-3' (SEQ ID NO: 19)

IBT3-oligo: 5'-GATCCCTGACGCTGCTGCAACT-GACGCGGACGACGGCTCTGACGCT GCTGCAACT-GACGCGGACGACGGCTCA-3' (SEQ ID NO: 20)

Overhangs were included in each oligonucleotide as to generate cohesive end compatible with the restriction sites NdeI and BamHI.

The IBT3+ and IBT3- oligonucleotides were annealed by combining 100 pmol of each oligonucleotide in deionized water into one tube and heated in a water bath set at 99° C. for 10 minutes after which the water bath was turned off. The oligonucleotides were allowed to anneal slowly until the water bath reached room temperature (20-25° C.). The annealed oligonucleotides were diluted in 100 µL water prior to ligation into the test vector. The pLX121 vector was digested in Buffer 2 (New England Biolabs, Beverly Mass.) comprising 10 mM Tris-HCl, 10 mM $MgCl_2$, 50 mM NaCl, 1 mM dithiothreitol (DTT); pH ~7.9) with the NdeI and BamHI restriction enzymes to release a 90 bp fragment corresponding to the original His6 containing inclusion body fusion partner and the linker from the parental pDEST17 plasmid that includes the att site of the Gateway™ Cloning System. The NdeI-BamHI fragments from the digested plasmid were separated by agarose gel electrophoresis and the vector was purified from the gel by using Qiagen QIAquick® Gel Extraction Kit (QIAGEN Valencia, Calif.; cat# 28704).

The diluted and annealed oligonucleotide (approximately 0.2 pmol) was ligated with T4 DNA Ligase (New England Biolabs Beverly, Mass.; catalog #M0202) to NdeI-BamHI digested, gel purified, plasmid pLX121 (approximately 50 ng) at 12° C. for 18 hours. DNA sequence analysis confirmed the expected plasmid sequence. The resulting plasmid (plasmid pLX147) comprised a chimeric gene (SEQ ID NO: 101) encoding the fusion peptide IBT 3-TBP101 (SEQ ID NO: 102).

The expression plasmid pLX147 was transformed into the arabinose inducible expression strain *E. coli* BL21-AI (Invitrogen; cat# C6070-03).

The expression vector was transferred into BL21-AI chemically competent *E. coli* cells for expression analysis. To produce the recombinant protein, 3 mL of LB-ampicillin broth (10 g/L bacto-tryptone, 5 g/L bacto-yeast extract, 10 g/L NaCl, 100 mg/L ampicillin; pH 7.0) was inoculated with one colony of the transformed bacteria and the culture was shaken at 37° C. until the $OD_{600}$ reached 0.6. Expression was induced by adding 0.03 mL of 20% L-arabinose (final concentration 0.2%, Sigma-Aldrich, St. Louis, Mo.) to the culture and shaking was continued for another 3 hours. For whole cell analysis, 0.1 $OD_{600}$ mL of cells were collected, pelleted, and 0.06 mL SDS PAGE sample buffer (1×LDS Sample Buffer (Invitrogen cat# NP0007), 6 M urea, 100 mM DTT) was added directly to the whole cells. The samples were heated at 99° C. for 10 minutes to solubilize the proteins. The solubilized proteins were then loaded onto 4-12% gradient MES NuPAGE® gels (NuPAGE® gels cat #NPO322, MES Buffer cat# NP0002; Invitrogen) and visualized with a Coomassie® G-250 stain (SimplyBlue™ SafeStain; Invitrogen; cat# LC6060).

Example 3

Verification of IBT-3 Induced Inclusion Body Formation

To verify that the fusion partner (IBT-3) drove expression into insoluble inclusion bodies, it was necessary to lyse the collected cells (0.1 $OD_{600}$ mL of cells) and fractionate the insoluble from the soluble fraction by centrifugation. Cells were lysed using CelLytic™ Express (Sigma, St. Louis, Mo. cat# C-1990) according to the manufacturer's instructions. Cells that do not produce inclusion bodies undergo complete lysis and yielded a clear solution. Cells expressing inclusion bodies appeared turbid even after complete lysis.

The method used to rank the inclusion body tag was a subjective visual inspection of SimplyBlue™ SafeStain stained PAGE gels. The scoring system was 0, 1, 2 or 3. If no band is detected then a zero score is given. A score of three is given to very heavily stained wide expressed bands. Bands that are weak are scored a one and moderate bands are scored a two. Any score above zero indicated the presence of inclusion bodies.

Soluble and insoluble fractions were separated by centrifugation and analyzed by polyacrylamide gel electrophoresis and visualized with SimplyBlue™ SafeStain. Analysis of the cell protein by polyacrylamide gel electrophoresis shows the production of the IBT-3 fusion with TBP101 peptide was expressed insolubly since the appropriate MW band (17 kDa) was present in the whole cell and insoluble fraction but not in the soluble cell fraction (Expression ranking for IBT-3=2). This result suggested that it was possible to have very small fusion partners (10-30 amino acids) to facilitate production of peptides in inclusion bodies.

Example 4

Synthesis and Evaluation of Addition Inclusion Body Tags

A series of additional fusion proteins were prepared by fusing each of the following inclusion body tags (IBTs) to soluble peptide of interest using the methods described in Example 2. The sequence identification numbers of the oligos used to prepare the various IBTs are provided in Table 2. Expression ranking evaluation was conducted as described in Example 3. The results of the expression ranking experiments are provided in Table 4

TABLE 2

Oligonucleotide Sequences Used to Prepare the Various Inclusion Body Tags

| Inclusion Body Tag | DNA strand | Oligonucleotide (SEQ ID NO) | IBT Amino Acid Sequence (SEQ ID NO) |
|---|---|---|---|
| IBT-3 | + | 19 | 67 |
| IBT-3 | − | 20 | |
| IBT-4 | + | 21 | 68 |
| IBT-4 | − | 22 | |
| IBT-23 | + | 23 | 69 |
| IBT-23 | − | 24 | |
| IBT-24 | + | 25 | 70 |
| IBT-24 | − | 26 | |
| IBT-25 | + | 27 | 71 |
| IBT-25 | − | 28 | |
| IBT-26 | + | 29 | 72 |
| IBT-26 | − | 30 | |
| IBT-27 | + | 31 | 73 |
| IBT-27 | − | 32 | |
| IBT-28 | + | 33 | 74 |
| IBT-28 | − | 34 | |
| IBT-29 | + | 35 | 75 |
| IBT-29 | − | 36 | |
| IBT-30 | + | 37 | 76 |
| IBT-30 | − | 38 | |

TABLE 2-continued

Oligonucleotide Sequences Used to Prepare the Various Inclusion Body Tags

| Inclusion Body Tag | DNA strand | Oligonucleotide (SEQ ID NO) | IBT Amino Acid Sequence (SEQ ID NO) |
|---|---|---|---|
| IBT-31 | + | 39 | 77 |
| IBT-31 | − | 40 | |
| IBT-32 | + | 41 | 78 |
| IBT-32 | − | 42 | |
| IBT-33 | + | 43 | 79 |
| IBT-33 | − | 44 | |
| IBT-34 | + | 45 | 80 |
| IBT-34 | − | 46 | |
| IBT-35 | + | 47 | 81 |
| IBT-35 | − | 48 | |
| IBT-36 | + | 49 | 82 |
| IBT-36 | − | 50 | |
| IBT-37 | + | 51 | 83 |
| IBT-37 | − | 52 | |
| IBT-38 | + | 53 | 84 |
| IBT-38 | − | 54 | |
| IBT-39 | + | 55 | 85 |
| IBT-39 | − | 56 | |
| IBT-40 | + | 57 | 86 |
| IBT-40 | − | 58 | |
| IBT-54 | + | 59 | 87 |
| IBT-54 | − | 60 | |
| IBT-89 | + | 61 | 88 |
| IBT-89 | − | 62 | |
| IBT-90 | + | 63 | 89 |
| IBT-90 | − | 64 | |
| IBT-95 | + | 65 | 90 |
| IBT-95 | − | 66 | |

The nucleotide and amino acid sequences associated with each of the fusion proteins is provided in Table 3. An alignment of the present inclusion body tags is provided in Table 5.

TABLE 3

Fusion Protein Sequences

| Fusion Protein | Expression Plasmid Designation | Fusion Protein Nucleic acid Sequence (SEQ ID NO.) | Fusion Protein Amino Acid Sequence (SEQ ID NO.) |
|---|---|---|---|
| IBT 24-TBP101 | pLX170 | 91 | 92 |
| IBT 54-TBP101 | pLX213 | 93 | 94 |
| IBT 25-TBP101 | pLX171 | 95 | 96 |
| IBT 29-TBP101 | pLX327 | 97 | 98 |
| IBT 95-TBP101 | pLX294 | 99 | 100 |
| IBT 3-TBP101 | pLX147 | 101 | 102 |
| IBT 4-TBP101 | pLX148 | 103 | 104 |
| IBT 23-TBP101 | pLX183 | 105 | 106 |
| IBT 27-TBP101 | pLX175 | 107 | 108 |
| IBT 28-TBP101 | pLX199 | 109 | 110 |
| IBT 37-TBP101 | pLX243 | 101 | 112 |
| IBT 26-TBP101 | pLX326 | 113 | 114 |
| IBT 30-TBP101 | pLX172 | 115 | 116 |
| IBT 31-TBP101 | pLX193 | 117 | 118 |
| IBT 35-TBP101 | pLX314 | 119 | 120 |
| IBT 36-TBP101 | pLX315 | 121 | 122 |
| IBT 38-TBP101 | pLX316 | 123 | 124 |
| IBT 89-TBP101 | pLX288 | 125 | 126 |
| IBT 90-TBP101 | pLX289 | 127 | 128 |
| IBT 32-TBP101 | pLX173 | 129 | 130 |
| IBT 33-TBP101 | pLX174 | 131 | 132 |
| IBT 34-TBP101 | pLX313 | 133 | 134 |
| IBT 40-TBP101 | pLX195 | 135 | 136 |

TABLE 4

Inclusion Body Tag Expression Ranking

| IBT Designation | Inclusion Body Tag Amino Acid Sequence (SEQ ID NO.) | Epression Ranking |
|---|---|---|
| IBT 24 | SRRPRQLQQRQ (SEQ ID NO:70) | 3 |
| IBT 54 | SRRDPRQLQQRQ (SEQ ID NO:87) | 3 |
| IBT 25 | SRRPRQLQQRQDPSRRPRQLQQRQDPSRRPRQLQQRQ (SEQ ID NO:71) | 3 |
| IBT 29 | SEEPEQLQQEQSRRPRQLQQRQ (SEQ ID NO:75) | 3 |
| IBT 95 | SRRPRQLQQRQSLGYGGLYGY (SEQ ID NO:90) | 3 |
| IBT 3 | SRRPRQLQQRQSRRPRQLQQRQ (SEQ ID NO:67) | 2 |
| IBT 4 | SRRPRQLQQRQHHQQQQE (SEQ ID NO:68) | 2 |
| IBT 23 | SRRPRQLQQRQSRRPRQLQQRQSRRPRQLQQRQ (SEQ ID NO:69) | 2 |
| IBT 27 | SREPEQLQQRQSRRPEQLQQRQ (SEQ ID NO:73) | 2 |
| IBT 28 | SREPEQLQQRQSREPEQLQQRQ (SEQ ID NO:74) | 2 |
| IBT 37 | SRRPRQLQQRQSRRPRQLQQRQEEEE (SEQ ID NO:83) | 2 |
| IBT 26 | SRRPEQLQQRQSRRPEQLQQRQ (SEQ ID NO:72) | 1 |
| IBT 30 | SREPEQLQQEQSREPEQLQQRQ (SEQ ID NO:76) | 1 |
| IBT 31 | SREPEQLQQEQSREPEQLQQEQ (SEQ ID NO:77) | 1 |
| IBT 35 | SRRPRQLQQRQSRRPRQLQQRQEE (SEQ ID NO:81) | 1 |
| IBT 36 | SRRPRQLQQRQSRRPRQLQQRQEEE (SEQ ID NO:82) | 1 |
| IBT 38 | SRRPRQLQQRQSRRPRQLQQRQEEEEEE (SEQ ID NO:84) | 1 |
| IBT 89 | SRRPRQDPLQQRQDPSRRPRQLQQRQ (SEQ ID NO:88) | 1 |
| IBT 90 | SRRPRQDPLQQRQDPSRRPRQDPLQQRQ (SEQ ID NO:89) | 1 |
| IBT 32 | SREPEQLQQEQSEEPEQLQQEQ (SEQ ID NO:78) | 0 |
| IBT 33 | SEEPEQLQQEQSEEPEQLQQEQ (SEQ ID NO:79) | 0 |
| IBT 34 | SRRPRQLQQRQSRRPRQLQQRQE (SEQ ID NO:80) | 0 |
| IBT 40 | SRRPRQLQQRQSRRPRQLQQRQEEEEEEEEEE (SEQ ID NO:86) | 0 |

TABLE 5

| Inclusion Body Tag Sequence Alignment | |
|---|---|
| IBT 24 | --SRRPRQLQQRQ------------------------ |
| IBT 3 | --SRRPRQLQQRQ--SRRPRQLQQRQ------------- |
| IBT 34 | --SRRPRQLQQRQ--SRRPRQLQQRQE----------- |
| IBT 35 | --SRRPRQLQQRQ--SRRPRQLQQRQEE---------- |
| IBT 36 | --SRRPRQLQQRQ--SRRPRQLQQRQEEE--------- |
| IBT 37 | --SRRPRQLQQRQ--SRRPRQLQQRQEEEE-------- |
| IBT 38 | --SRRPRQLQQRQ--SRRPRQLQQRQEEEEEE------ |
| IBT 40 | --SRRPRQLQQRQ--SRRPRQLQQRQEEEEEEEEEE--- |
| IBT 25 | --SRRPRQLQQRQDPSRRPRQLQQRQDPSRRPRQLQQRQ |
| IBT 26 | --SRRPEQLQQRQ--SRRPEQLQQRQ------------ |
| IBT 27 | --SREPEQLQQRQ--SRRPEQLQQRQ------------ |
| IBT 28 | --SREPEQLQQRQ--SREPEQLQQRQ------------ |

TABLE 5-continued

| Inclusion Body Tag Sequence Alignment | |
|---|---|
| IBT 29 | --SEEPEQLQQEQ--SRRPRQLQQRQ------------ |
| IBT 30 | --SREPEQLQQEQ--SREPEQLQQRQ------------ |
| IBT 31 | --SREPEQLQQEQ--SREPEQLQQEQ------------ |
| IBT 32 | --SREPEQLQQEQ--SEEPEQLQQEQ------------ |
| IBT 33 | --SEEPEQLQQEQ--SEEPEQLQQEQ------------ |
| IBT 54 | ---------------SRRDPRQLQQRQ------------ |
| IBT 23 | --SRRPRQLQQRQ--SRRPRQLQQRQSRRPRQLQQRQ-- |
| IBT 89 | SRRPRQDPLQQRQDPSRRPRQLQQRQ------------- |
| IBT 90 | SRRPRQDPLQQRQDPSRRPRQDPLQQRQ----------- |
| IBT 4 | ---------------SRRPRQLQQRQHHQQQQE------ |
| IBT 95 | ---------------SRRPRQLQQRQSLGYGGLYGY--- |

What is claimed is:

1. An inclusion body tag comprising the structure:

[Ser-(Xaa$_1$)-(Xaa$_2$)-(Xaa$_3$)-(Xaa$_4$)-(Xaa$_5$)-Leu-Gln-Gln-(Xaa$_6$)-Gln]$_n$ wherein n=1-20,
and wherein
(Xaa$_1$)=Arg or Glu;
(Xaa$_2$)=Arg or Glu;
(Xaa$_3$)=Pro or Gln;
(Xaa$_4$)=Arg, Glu, or Asp
(Xaa$_5$)=Gln or Pro;
(Xaa$_6$)=Arg or Glu;
wherein the inclusion body tag does not have the amino acid sequence as set forth in SEQ ID NO:139.

2. The inclusion body tag of claim 1 having the amino acid sequence selected from the group consisting of SEQ ID NOS: 67, 68, 69, 70, 71, 72, 73, 74, 75, 76, 77, 81, 82, 83, 84, 85, 88, 90, and 137.

3. A fusion peptide comprising the inclusion body tag of claim 1 operably linked to at least one peptide of interest.

4. The fusion peptide of claim 3, further comprising at least one cleavable peptide linker having at least one cleavage site.

5. The fusion peptide according to claim 3 wherein the peptide of interest is a hair binding peptide selected from the group consisting of SEQ ID NOS: 148 to 240.

6. The fusion peptide according to claim 3 wherein the peptide of interest is a skin binding peptide selected from the group consisting of SEQ ID NOS: 140 to 147.

7. The fusion peptide according to claim 3 wherein the peptide of interest is a nail binding peptide selected from the group consisting of SEQ ID NOS: 241 to 242.

8. The fusion peptide according to claim 3 wherein the peptide of interest is a polymer binding peptide selected from the group consisting of SEQ ID NOS: 298 to 331.

9. The fusion peptide according to claim 3 wherein the peptide of interest is an antimicrobial peptide selected from the group consisting of SEQ ID NOS: 243 to 271.

10. The fusion peptide according to claim 3 wherein the peptide of interest is a pigment binding peptide selected from the group consisting of SEQ ID NOS: 272-297.

* * * * *